(12) United States Patent
Murakami

(10) Patent No.: US 9,173,550 B2
(45) Date of Patent: Nov. 3, 2015

(54) MEDICAL APPARATUS

(75) Inventor: Kazushi Murakami, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1006 days.

(21) Appl. No.: 12/057,990

(22) Filed: Mar. 28, 2008

(65) Prior Publication Data

US 2009/0030273 A1 Jan. 29, 2009

Related U.S. Application Data

(63) Continuation-in-part of application No. 12/035,535, filed on Feb. 22, 2008, which is a continuation-in-part of application No. 11/809,488, filed on Jun. 1, 2007, now Pat. No. 8,021,293, which is a continuation-in-part of application No. 11/652,880, filed on Jan. 12, 2007, now Pat. No. 8,444,547, which is a continuation-in-part of application No. 11/435,183, filed on May 16, 2006, now Pat. No. 8,617,054, which is a continuation-in-part of application No. 11/331,963, filed on Jan. 13, 2006, now Pat. No. 8,092,371.

(51) Int. Cl.
*A61B 17/00* (2006.01)
*A61B 1/00* (2006.01)
(Continued)

(52) U.S. Cl.
CPC ............. *A61B 1/0052* (2013.01); *A61B 1/0055* (2013.01); *A61B 1/018* (2013.01); *A61B 17/29* (2013.01); *A61B 19/081* (2013.01); *A61B 19/22* (2013.01); *A61B 17/00234* (2013.01); *A61B 2017/00278* (2013.01); *A61B 2017/2905* (2013.01); *A61B 2017/2906* (2013.01); *A61B 2017/2908* (2013.01); *A61B 2017/2927* (2013.01); *A61B 2019/2219* (2013.01); *A61B 2019/2242* (2013.01); *A61B 2019/2269* (2013.01); *A61B 2019/4868* (2013.01)

(58) Field of Classification Search
USPC ........ 600/104, 106, 107, 123, 131, 114, 115, 600/139–154, 127, 129; 604/528; 606/1, 606/205–209
See application file for complete search history.

(56) References Cited

U.S. PATENT DOCUMENTS 4,245,624 A 1/1981 Komiya
4,577,621 A 3/1986 Patel
(Continued)

FOREIGN PATENT DOCUMENTS

CN 1602166 A 3/2005
CN 1886087 A 12/2006
(Continued)

OTHER PUBLICATIONS

U.S. Office Action dated Feb. 1, 2011 received in related U.S. Appl. No. 11/809,488.
(Continued)

*Primary Examiner* — Ryan Henderson
(74) *Attorney, Agent, or Firm* — Scully, Scott, Murphy & Presser, P.C.

(57) ABSTRACT

A medical apparatus according to the present invention includes: a flexible sheath; an arm section having a bending part capable of bending operation and a first channel capable of inserting a procedure instrument therethrough, the arm section being disposed to protrude from a tip of the sheath; and an operation stick having a second channel connected to the first channel and a bending operating part connected to the arm section by an operation-transmission member, wherein the operation stick has: a regulation section for regulating movement of the bending operating part; and a falloff-preventive section for engaging with the procedure instrument inserted in the second channel to prevent the procedure instrument from falling from the operation stick.

18 Claims, 52 Drawing Sheets

(51) Int. Cl.

| | |
|---|---|
| A61B 1/04 | (2006.01) |
| A61M 25/00 | (2006.01) |
| A61B 1/005 | (2006.01) |
| A61B 1/018 | (2006.01) |
| A61B 17/29 | (2006.01) |
| A61B 19/08 | (2006.01) |
| A61B 19/00 | (2006.01) |

(56) References Cited

U.S. PATENT DOCUMENTS

| | | | |
|---|---|---|---|
| 4,873,965 A | 10/1989 | Danieli | |
| 5,173,716 A | 12/1992 | Tetsuka | 43/903 |
| 5,217,114 A | 6/1993 | Gadberry et al. | |
| 5,299,559 A | 4/1994 | Bruce et al. | 600/141 |
| 5,318,013 A | 6/1994 | Wilk | |
| 5,395,367 A | 3/1995 | Wilk | |
| 5,448,989 A | 9/1995 | Heckele | |
| 5,683,349 A | 11/1997 | Makower et al. | |
| 5,855,569 A | 1/1999 | Komi | 604/526 |
| 5,916,147 A | 6/1999 | Boury | |
| 5,976,075 A | 11/1999 | Beane et al. | |
| 6,013,024 A | 1/2000 | Mitsuda et al. | |
| 6,352,503 B1 | 3/2002 | Matsui et al. | |
| 6,780,151 B2 | 8/2004 | Grabover et al. | |
| 7,833,156 B2 | 11/2010 | Williams et al. | |
| 2002/0087048 A1 | 7/2002 | Brock et al. | |
| 2004/0044270 A1 | 3/2004 | Barry | |
| 2004/0117032 A1 | 6/2004 | Roth | |
| 2004/0138525 A1 | 7/2004 | Saadat et al. | |
| 2004/0138529 A1 | 7/2004 | Wiltshire et al. | |
| 2004/0193212 A1 | 9/2004 | Taniguchi et al. | |
| 2005/0065397 A1 | 3/2005 | Saadat et al. | |
| 2005/0075538 A1 | 4/2005 | Banik et al. | |
| 2005/0090709 A1 | 4/2005 | Okada et al. | 6/104 |
| 2005/0119522 A1 | 6/2005 | Okada | |
| 2005/0222495 A1 | 10/2005 | Okada et al. | |
| 2005/0228224 A1 | 10/2005 | Okada et al. | |
| 2005/0234294 A1 | 10/2005 | Saadat et al. | |
| 2005/0234296 A1 | 10/2005 | Saadat et al. | |
| 2005/0250989 A1 | 11/2005 | Suzuki | |
| 2005/0273085 A1 | 12/2005 | Hinman et al. | 606/1 |
| 2006/0111615 A1 | 5/2006 | Danitz et al. | |
| 2006/0189845 A1 | 8/2006 | Maahs et al. | 600/146 |
| 2007/0004967 A1 | 1/2007 | Ueno et al. | |
| 2007/0043338 A1 | 2/2007 | Moll et al. | 606/1 |
| 2007/0156019 A1 | 7/2007 | Larkin et al. | |
| 2007/0167679 A1 | 7/2007 | Miyamoto et al. | |
| 2007/0167680 A1 | 7/2007 | Miyamoto et al. | |
| 2007/0232856 A1 | 10/2007 | Ueno et al. | |
| 2007/0270640 A1* | 11/2007 | Dimitriou et al. | 600/106 |
| 2007/0299387 A1 | 12/2007 | Williams et al. | |
| 2008/0051631 A1 | 2/2008 | Dejima et al. | |
| 2008/0065109 A1 | 3/2008 | Larkin | 606/130 |
| 2008/0221391 A1* | 9/2008 | Weitzner et al. | 600/118 |
| 2008/0262294 A1 | 10/2008 | Ewers et al. | |

FOREIGN PATENT DOCUMENTS

| | | |
|---|---|---|
| EP | 1 872 709 A | 1/2008 |
| EP | 1 967 123 A1 | 9/2008 |
| JP | 55-45436 | 3/1980 |
| JP | 56-104501 | 8/1981 |
| JP | 63-102401 | 7/1988 |
| JP | S63-242217 | 10/1988 |
| JP | 5-5105 U | 1/1993 |
| JP | 5-49594 | 3/1993 |
| JP | 8-131441 | 5/1996 |
| JP | 08322787 A | 12/1996 |
| JP | 10-258022 | 9/1998 |
| JP | 11-318815 A | 11/1999 |
| JP | 2001-46393 A | 2/2001 |
| JP | 2002-253563 A | 9/2002 |
| JP | 2004-180781 | 7/2004 |
| JP | 2004-290569 | 10/2004 |
| JP | 2005-287963 | 10/2005 |
| JP | 2005-296412 | 10/2005 |
| JP | 2006-141624 | 6/2006 |
| JP | 2006-516910 A | 7/2006 |
| JP | 516910 | 7/2006 |
| JP | 2007-151595 | 6/2007 |
| JP | 2007-175070 | 7/2007 |
| JP | 2007-275624 A | 10/2007 |
| JP | 2005261688 A | 9/2009 |
| WO | WO 2004/064600 A2 | 8/2004 |
| WO | 2005/009227 A1 | 2/2005 |
| WO | WO 2007/057880 A2 | 5/2007 |
| WO | WO 2007/074571 A1 | 7/2007 |
| WO | WO 2007/080974 A1 | 7/2007 |
| WO | WO 2007/127199 A1 | 11/2007 |

OTHER PUBLICATIONS

U.S. Office Action dated Mar. 24, 2010, received in related U.S. Appl. No. 11/435,183.
U.S. Office Action dated Mar. 2, 2011 received in related U.S. Appl. No. 11/652,880.
U.S. Office Action dated Mar. 16, 2011 received in related U.S. Appl. No. 11/435,183.
U.S. Office Action dated Jul. 9, 2010.
Office Action dated Oct. 5, 2011 from corresponding U.S. Appl. No. 11/652,880.
Office Action dated May 15, 2012 received in related U.S. Appl. No. 11/652,880.
U.S. Office Action dated Mar. 28, 2012 of related U.S. Appl. No. 13/212,610.
Japanese Notice of Allowance dated Jun. 4, 2013 issued in corresponding Application No. 2009-013615 together with an English Language Translation.
Extended Supplementary European Search Report dated Jul. 18, 2014 from related European Application No. 07 70 6679.3.
Notice of Allowance dated Jan. 22, 2013 issued in corresponding U.S. Appl. No. 11/652,880.
U.S. Office Action mailed May 31, 2012 in related U.S. Appl. No. 12/024,704.
U.S. Office Action mailed Jun. 6, 2012 in related U.S. Appl. No. 12/127,449.
U.S. Office Action mailed Jun. 26, 2012 in related U.S. Appl. No. 12/058,029.
U.S. Office Action mailed Jul. 3, 2012 in related U.S. Appl. No. 12/035,535.
Chinese Office Action dated Jul. 3, 2012 from related Chinese Patent Application Publication No. 2007-80008372.7, together with an English language translation.
Japanese Notice of Allowance dated Aug. 20, 2013 issued in corresponding Application No. 2009-058066 with an English language Translation.
U.S. Office Action dated Mar. 19, 2013 issued in corresponding U.S. Appl. No. 12/058,029.
Japanese Office Action (Notice of Reasons for Rejection) dated Dec. 18, 2012 from corresponding Japanese Patent Application Publication No. JP 2009-013615, together with an English language translation.
Japanese Office Action (Notice of Reasons for Rejection) dated Dec. 18, 2012 from corresponding Japanese Patent Application Publication No. JP 2009-027835, together with an English language translation.
Japanese Office Action (Notice of Reasons for Rejection) dated Dec. 18, 2012 from corresponding Japanese Patent Application Publication No. JP 2009-033278, together with an English language translation.
Japanese Office Action dated Feb. 19, 2013 together with an English Translation issued in corresponding Japanese Application No. 2009058066.
Office Action dated Dec. 16, 2014 received in related U.S. Patent Application, namely U.S. Appl. No. 12/035,535.

* cited by examiner

MEDICAL APPARATUS

CROSS REFERENCE TO RELATED APPLICATIONS

This is a Continuation In-part Application (CIP) based on U.S. patent application Ser. No. 12/035,535, titled "MEDICAL TREATMENT ENDOSCOPE", filed Feb. 22, 2008, which is a CIP based on U.S. patent application Ser. No. 11/809,488, titled "MEDICAL TREATMENT ENDOSCOPE", filed Jun. 1, 2007, which is a CIP based on U.S. patent application Ser. No. 11/652,880, titled "MEDICAL TREATMENT ENDOSCOPE", filed Jan. 12, 2007, which is a CIP based on U.S. patent application Ser. No. 11/435,183, titled "MEDICAL TREATMENT ENDOSCOPE", filed May 16, 2006, which is a CIP based on U.S. patent application Ser. No. 11/331,963, titled "MEDICAL TREATMENT ENDOSCOPE", filed Jan. 13, 2006, the content of which is incorporated herein by reference.

BACKGROUND OF THE INVENTION

1. Field of the Invention

The present invention relates to a medical apparatus used to be inserted in to a body cavity.

2. Background Art

Laparoscopic surgery is a conventionally known technique that has been employed when performing a medical procedure such as observation or treatment of the internal organs of the human body. Rather than making a large abdominal incision, laparoscopic surgery allows for the procedure to be carried out by making several openings in the abdominal wall, and inserting a laparoscope and surgical instruments such as forceps into these openings. This type of surgery offers the benefit of being less invasive on the patient, since only small openings are made in the abdominal wall.

As a method of even further reducing stress on the patient, it has been proposed in recent years to carry out medical procedures by inserting a flexible endoscope into the patient via a natural opening such as the mouth, nostrils or anus. An example of a medical treatment endoscope used in such procedures is disclosed in U.S. Patent Application Publication No. 2005/0065397.

In the medical treatment endoscope disclosed in this reference, arm members that have a bendable end are respectively inserted into a plurality of lumens disposed within a flexible inserted part that is inserted into the body via the mouth of the patient. By inserting respective instruments through these arm members, the procedure site of interest can be approached from different directions with the various instruments. Accordingly, a plurality of procedures can be carried out in continuum by means of a single endoscope inserted into the body.

SUMMARY OF THE INVENTION

A medical apparatus according to the present invention includes: a flexible sheath; an arm section having a bending part capable of a bending operation and a first channel capable of inserting a procedure instrument therethrough, the arm section being disposed to protrude from a tip of the sheath; and an operation stick having a second channel connected to the first channel and a bending operating part connected to the arm section by an operation-transmission member, wherein the operation stick has: a regulation section for regulating movement of the bending operating part; and a falloff-preventive section for engaging with the procedure instrument inserted in the second channel to prevent the procedure instrument from falling from the operation stick.

DETAILED DESCRIPTION OF THE INVENTION

Embodiments of the present embodiment will be described as follows. The basic structure of a medical treatment endoscope as an example of a medical apparatus of the present invention is disclosed by the corresponding U.S. patent application Ser. Nos. 11/331,963, 11/435,183, and 11/652,880 of the present patent application. Disclosure by these applications is incorporated into the following explanation.

First Embodiment

A medical treatment endoscope according to the present embodiment is functionally divided into an operation section for conducting necessary treatments by means of arm sections and procedure instruments; and an endoscope operation section for operating an endoscope. The present embodiment features operation sections that are operable in separate locations from the endoscope. An operation section built in an endoscope operation section necessitates an operator conducting all the operations alone, i.e., inevitably complex operations. The present embodiment enables two operators to share operations, i.e., operating an endoscope and conducting a treatment; thus, facilitating the operations.

Figure 1:
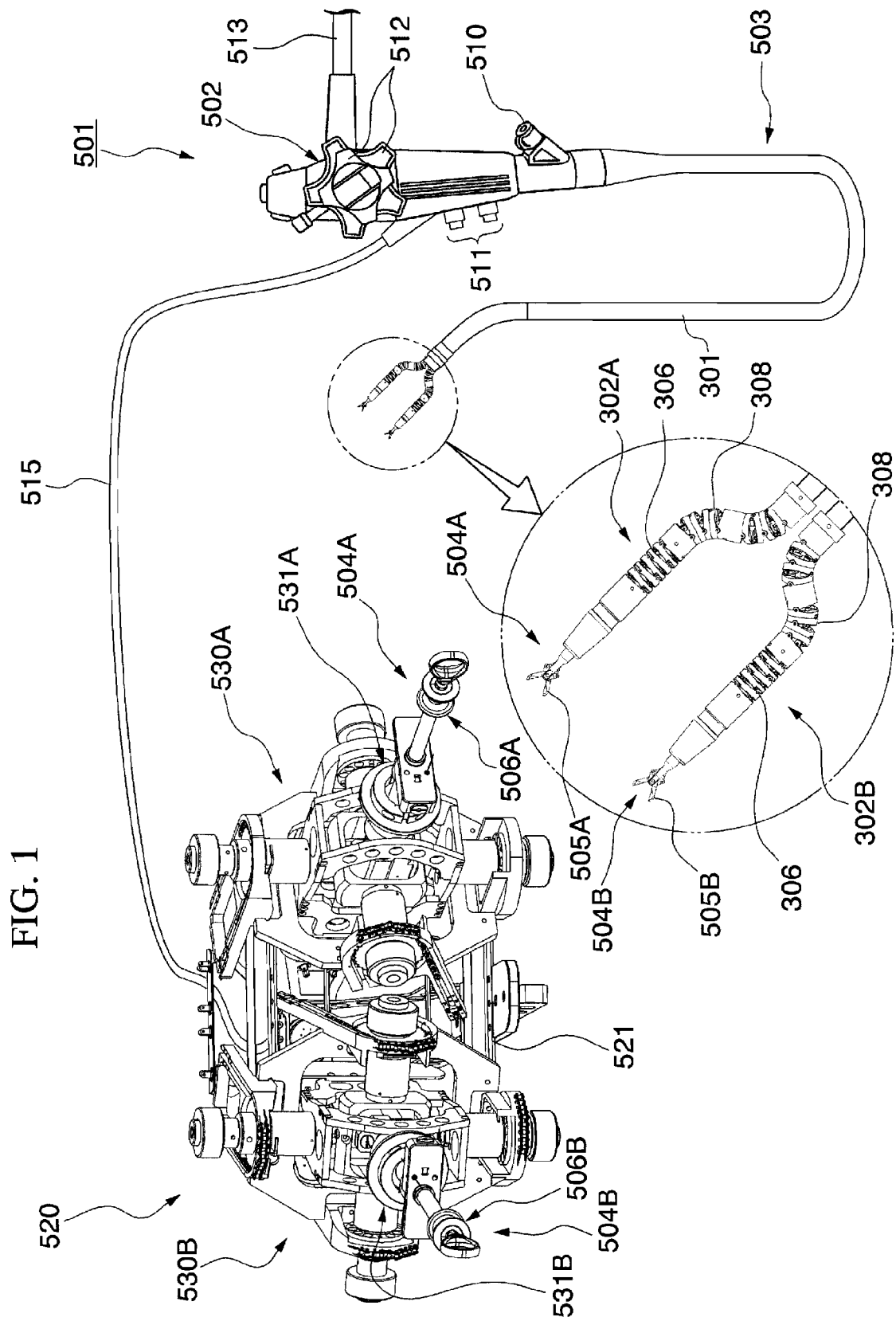
FIG. 1 is a perspective view showing a medical treatment endoscope according to a first embodiment.

As illustrated in FIG. 1, an endoscope insertion section 503 fully integrated with a medical treatment endoscope 501 extends from an end of an endoscope insertion section 502. An elongated and flexible endoscope insertion section 503 has the same structure as those of the U.S. patent application Ser. Nos. 11/435,183 and 11/652,880. That is, the endoscope insertion section 503 has a first sheath 301 having a first arm section 302A and a second arm section 302B on the tip of the first sheath 301. Treatment sections 505A and 505B of procedure instruments 504A and 504B each protrude from the tips of the arm sections 302A and 302B. A first bending part 306 and a second bending part 308, in this order from the tips of the arm sections 302A and 302B, are formed to each arm section 302A and 302B. Combined use with a third bending section 203B formed in the first sheath 301 enables a bending operation in a human body. The first and second arm members 302A and 302B may be inserted into another sheath protruding from the tip of the sheath 301 as disclosed by the U.S. patent application Ser. No. 11/652,880. Meanwhile, an operation section 520 is enlarged in FIG. 1 to help better understanding.

A forceps cap 510 is provided to a side of the endoscope insertion section 502 near an end that continues to the endoscope insertion section 503. The forceps cap 510 communicates to an operation channel formed in the first sheath 301. Inserting another procedure instrument, which is not shown in the drawing, from here enables the procedure instrument to protrude from the tip of the endoscope insertion section 503. In addition, disposed to the endoscope insertion section 502 are a switch 511, an angle knob 512, and a universal cable 513 that is connected to a control apparatus that is not shown in the drawing. For example, operating the switch 511 provides air-supply, water-supply, and suction through a channel formed in the first sheath 301. Operating the angle knob 512 bends the third bending section 203B into four direction with respect to an axial line.

In addition, an elongated flexible connection sheath 515 extends from the other end of the endoscope insertion section 502. An operation section 520 is disposed at an end of a connection sheath 515.

The operation section 520 has a base 521 that fixes the connection sheath 515. Attached to the base 521 are a first operation unit 530A and a second operation unit 530B. The first operation unit 530A has an operation stick 531A into which an operation section 506A of the procedure instrument 504A is inserted. The procedure instrument 504A is passed through the first arm member 302A. The operation section 506A is supported by the operation stick 531A so as to be capable of extending and retracting in the axial line and bending in four directions with respect to the axial line. The second operation unit 530B has an operation stick 531B into which an operation section 506B of the procedure instrument 504B is inserted. The procedure instrument 504B is passed through the second arm member 302B. The operation section 506B is supported by the operation stick 531B so as to be capable of extending and retracting in the axial line and bending in four directions with respect to the axial line. Furthermore, the operation section 520 fixed to an operation bed enables operation of the first second operation unit 530A and the second operation unit 530B.

Figure 2:
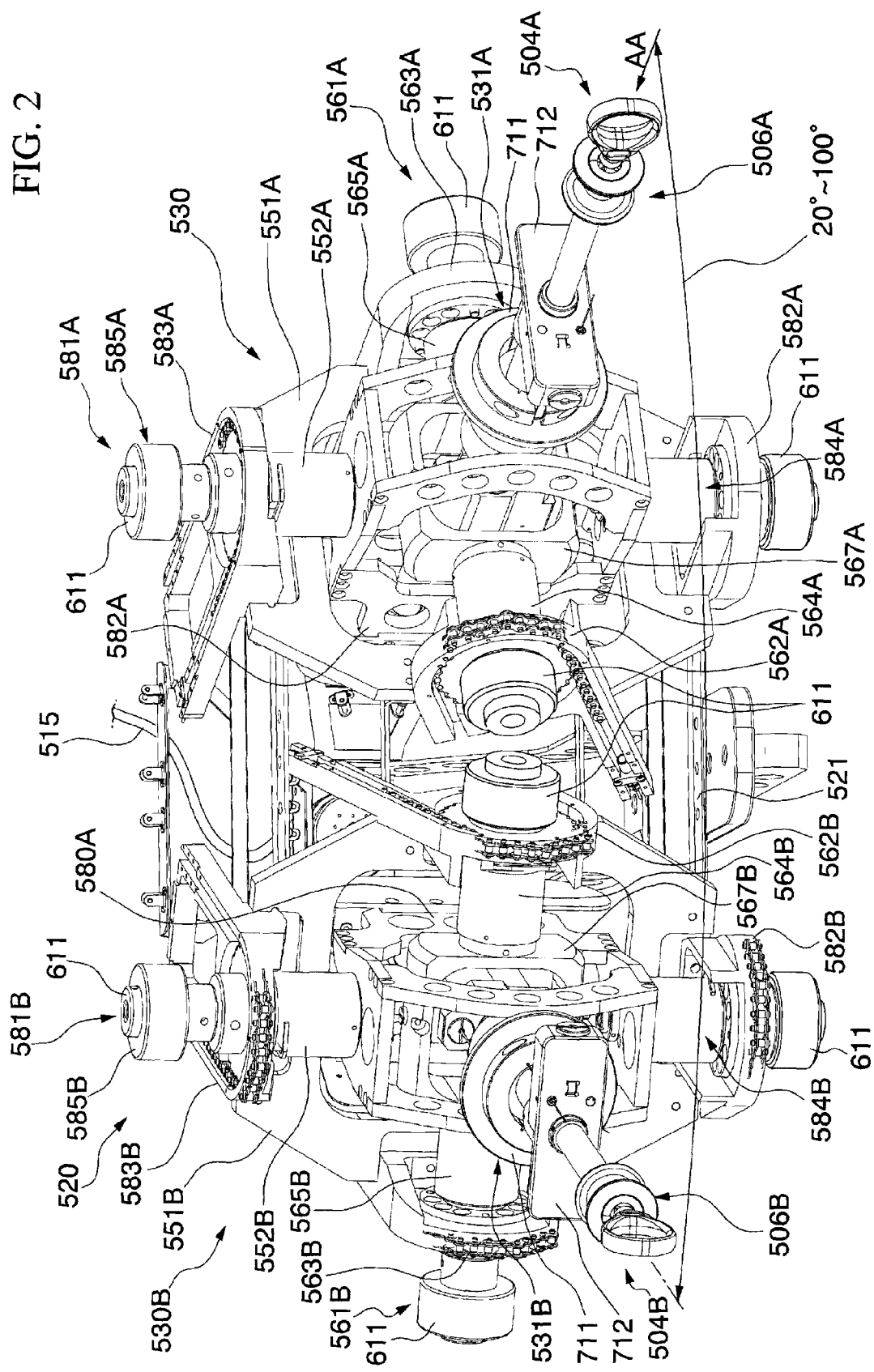
FIG. 2 is an enlarged view of an operation section.

As illustrated in FIG. 2 in an enlarged view, the operation units 530A and 530B are disposed diagonally so that portions closer to the connection sheath 515 are placed closer to each other. Two operation sections 506A and 506B (or two operation sticks 531A and 531B) are disposed at angles between 20° and 100°. Disposing the operation sections 506A and 506B with the opening angle relative to an operator facilitates the operator's operation, thus improving operability. In addition, the width of the operation section 520 closer to the connection sheath 515 can be reduced. Also, as disclosed by U.S. patent application Ser. No. 11/652,880, disposition (in horizontal direction) of arm sections 302A and 302B in an endoscope image obtained through an object lens of a viewing device (viewing unit) attached to the first sheath 301 can be coincided with the disposition (in horizontal direction) of the two operation units 530A and 530B. This improves correlation of an operator's perception and actual inner-body movement, thereby facilitating manipulation. Furthermore, less force is required for an operator to operate only the operation sticks 531A and 531B and the operation sections 506A and 506B of the procedure instruments 504A and 504B. Dispositions having reverse correlation with respect to horizontal or vertical direction provide similar operational perception obtained by laparoscopic instruments.

The configuration of the first operation unit 530A is explained.

Figure 3:
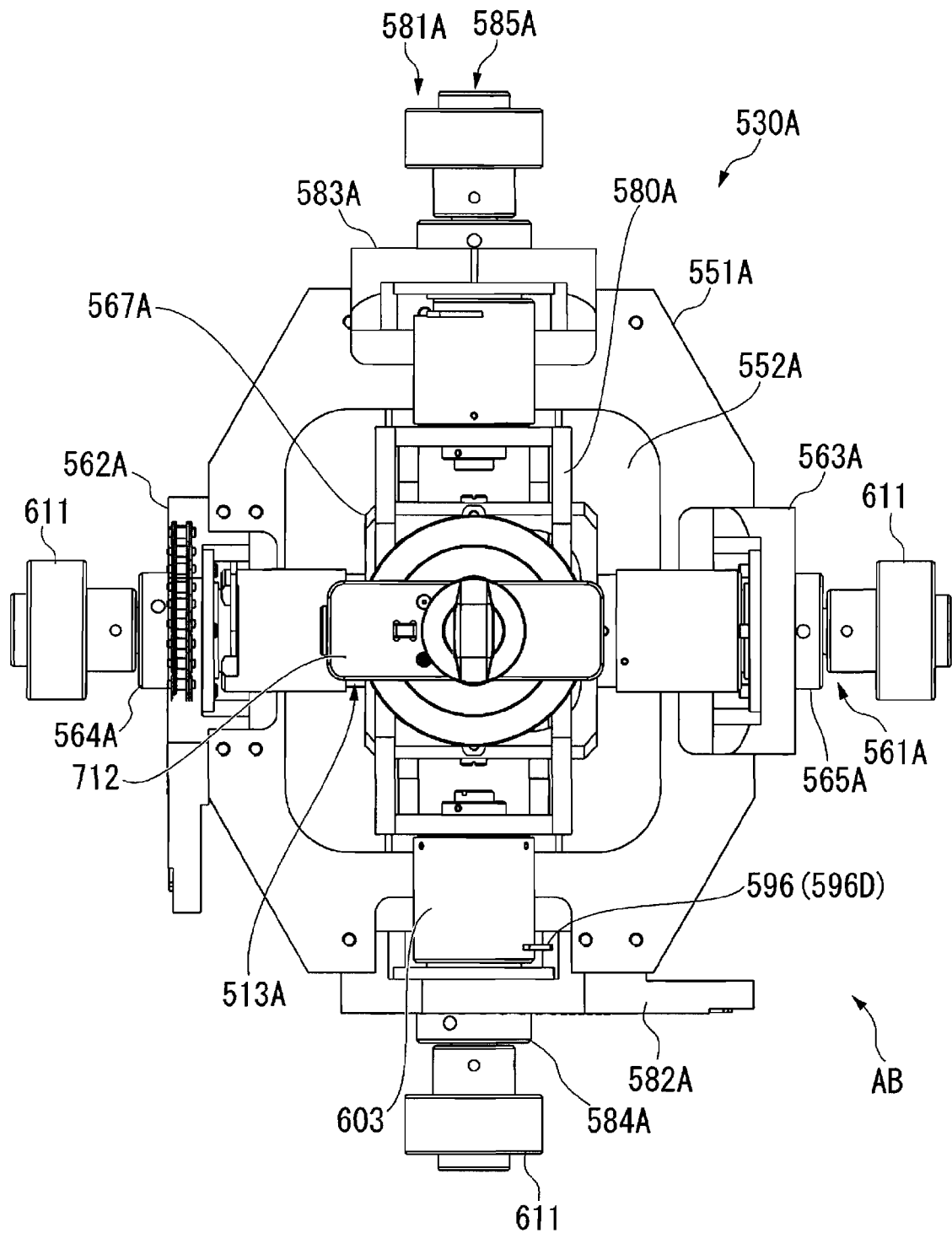
FIG. 3 is a view taken along the line A-A in FIG. 2 in parallel with an axial direction of a first operation section.
Figure 4:
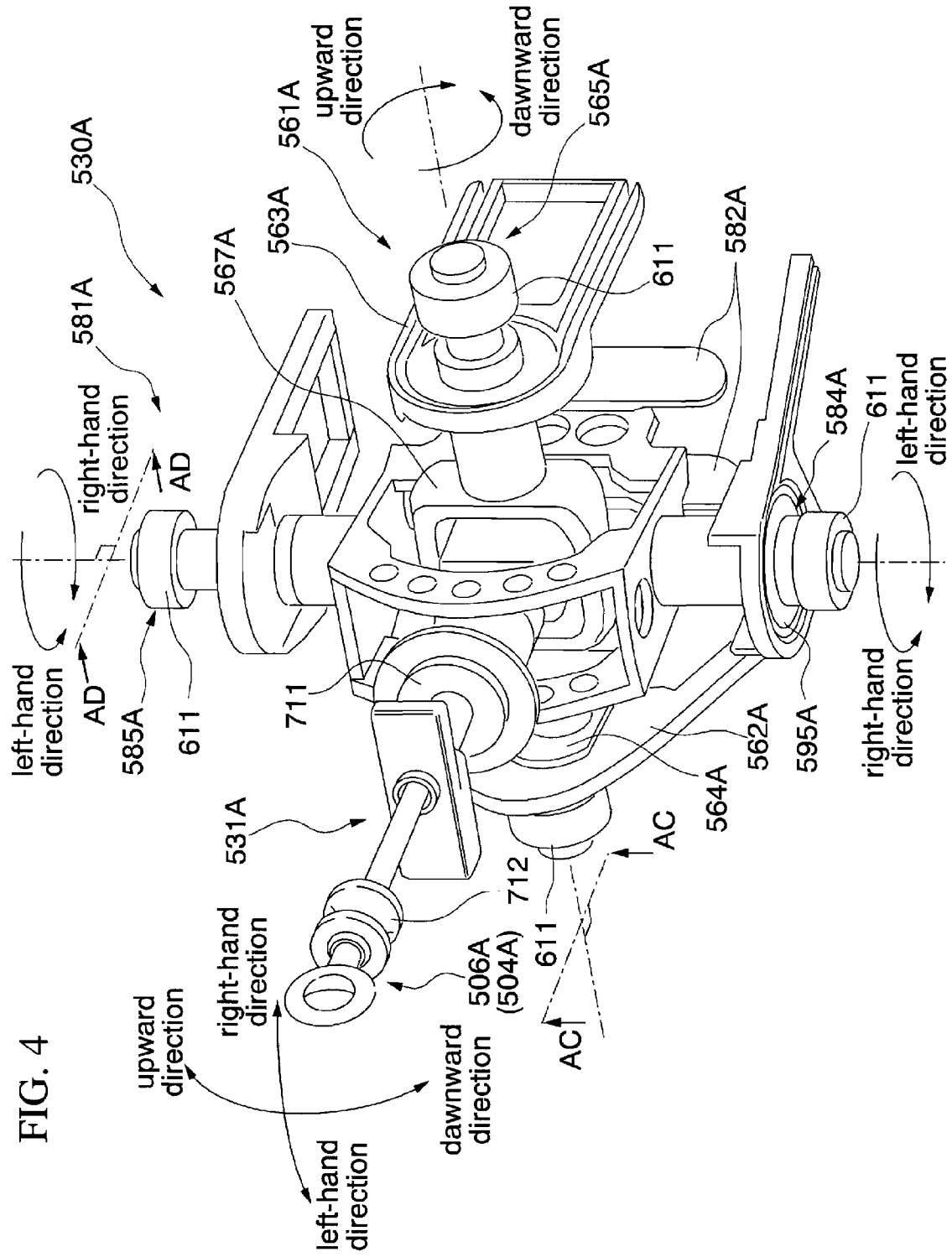
FIG. 4 is a view on arrow AB in FIG. 3.

As illustrated in FIGS. 2 to 4, the first operation unit 530A has a bracket 551A fixed to the base 521. The bracket 551A is fixed so that an opening 552A is substantially orthogonal to the center line of the first operation unit 530A. A first rotation mechanism 561A is attached to horizontal side surfaces of the bracket 551A. The first rotation mechanism 561A has a pair of support chips 562A and 563A that are fixed to place the opening 552A of the bracket 551A therebetween. A rotation shaft 564A is disposed to the support chip 562A. A rotation shaft 565A is disposed to the support chip 563A. The rotation shafts 564A and 565a are disposed coaxially. A frame 567A is supported by this pair of rotation shafts 564A and 565a so as to be freely capable of rotating with respect to the bracket 551. An opening of a rectangular frame 567A is disposed orthogonal to the center line of the first operation unit 530A. The operation stick 531A is inserted through the frame 567A. The operation stick 531A engaging with the frame 567A in rotating angles of the rotation shafts 564A and 565a is inserted so as to be independently capable of tilting in the axial lines of the rotation shafts 564A and 565A.

Figure 5:
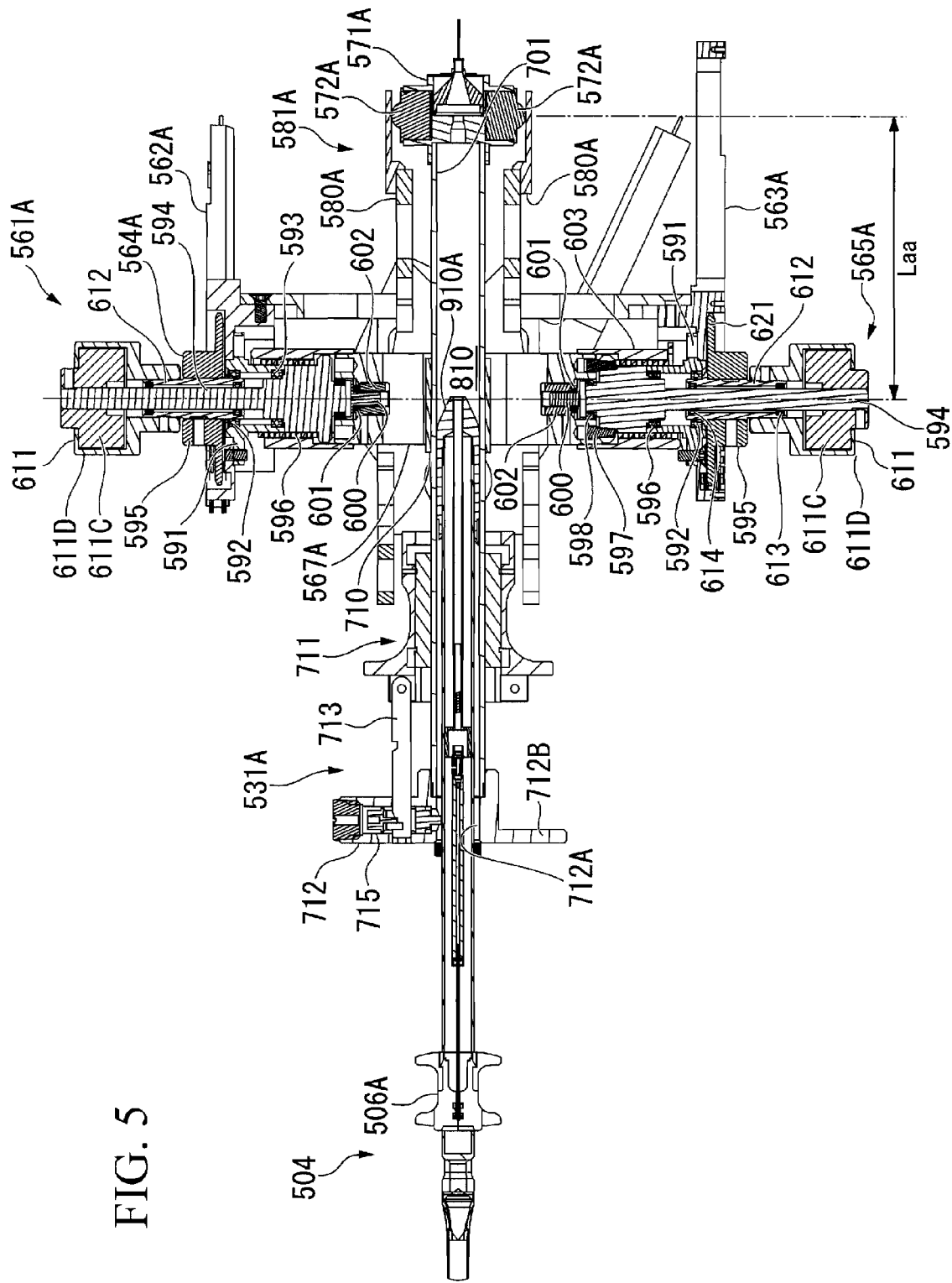
FIG. 5 is a cross-sectional view along the line AC-AC in FIG. 4.

As illustrated in FIG. 5, the tip section 571A of the operation stick 531A extends beyond the frame 567A. Ball rollers 572A are provided to the tip section 571A. The ball rollers 572A are disposed to place the center line of the operation stick 531A therebetween. The line passing through the centers of two ball rollers 572A is parallel with the axial lines of the rotation shafts 564A and 565A of the first rotation mechanism 561A as illustrated, i.e., where the operation stick 531A is not tilted. Distances Laa between the rotation shaft 564A and 565A and the ball rollers 572A are, for example, 50 to 200 mm.

Frames 580A of the second rotation mechanism 581A are farther disposed so as to place the ball rollers 572A therebetween and slide on the ball rollers 572A. The frames 580A are supported rotatively by the pair of rotation shafts 584A and 585A. The pair of the rotation shafts 584A and 585A are disposed coaxially so that the axial lines are orthogonal to a pair of rotation shafts 564A and 565A and also orthogonal to the center line of the first operation unit 530A. The rotation shafts 584A and 585A are supported by support chips 582A and 583A each fixed on a vertical side surface of the bracket 551A.

The configuration of the rotation shafts 584A and 585A of the second rotation mechanism 581A will be explained here. Since the rotation shafts 584A and 585A have the same configuration, the rotation shaft 584A will be explained herein for reference.

Figure 6:
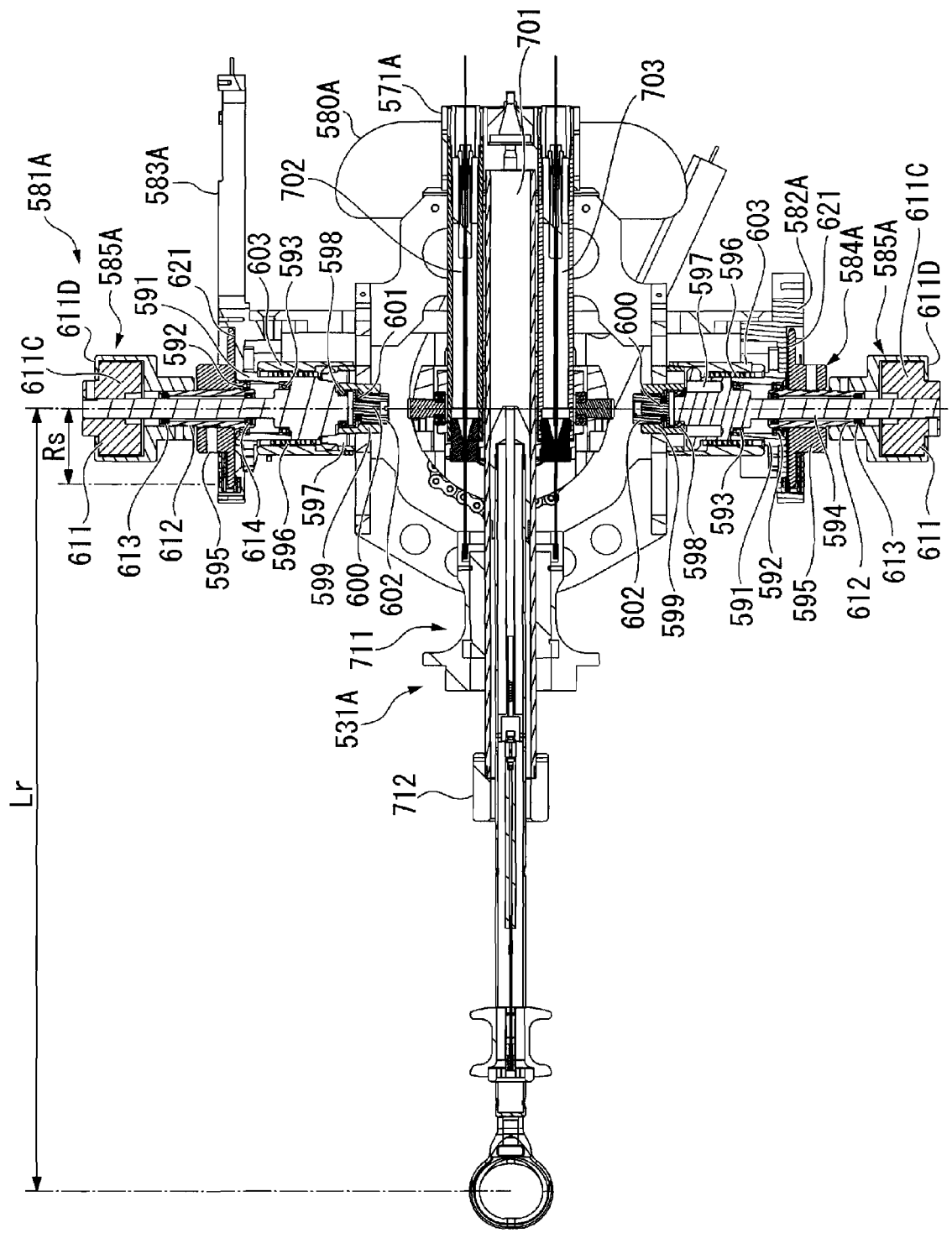
FIG. 6 is a cross-sectional view along the line AD-AD in FIG. 4.
Figure 7:
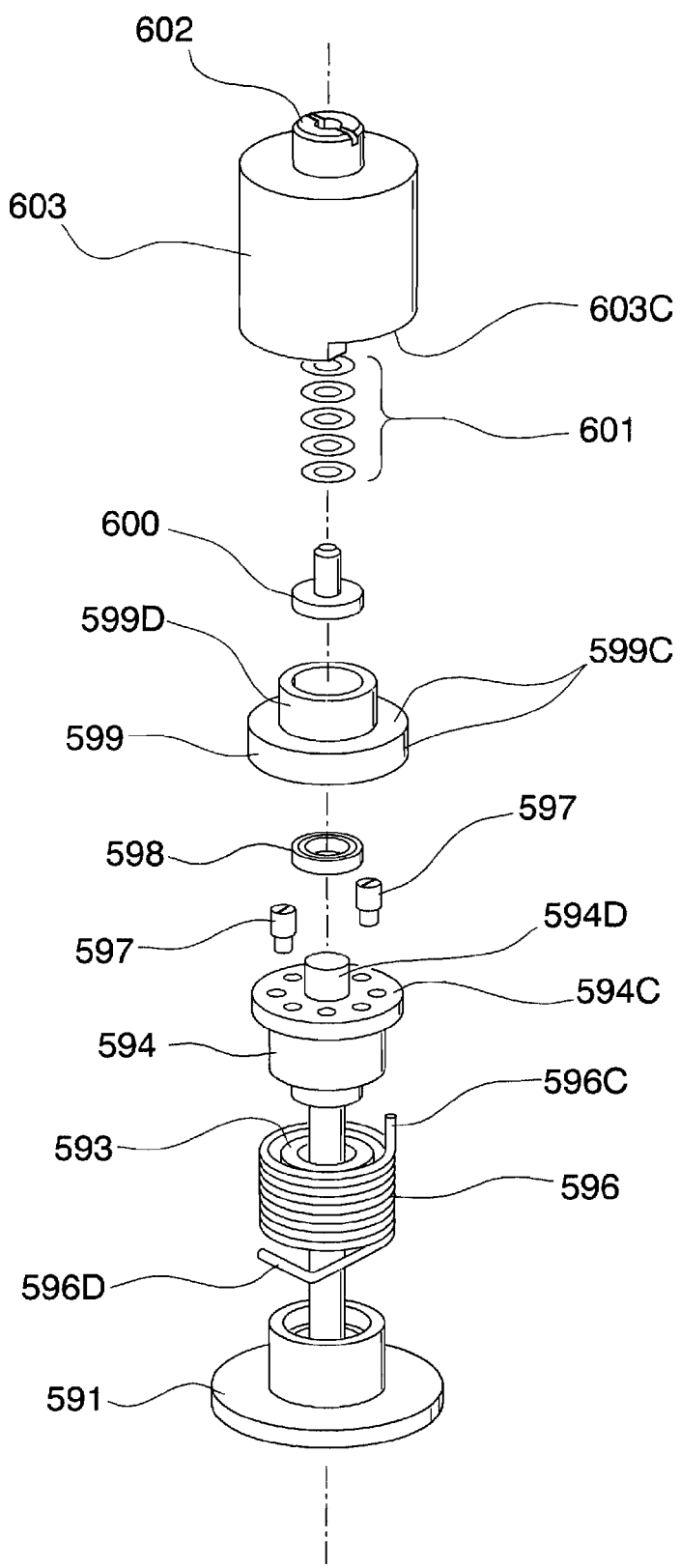
FIG. 7 is an exploded view for a rotational axis.

As illustrated in FIGS. 6 and 7, the rotation shaft 584A has a bearing 591 fixed to the support chip 582A. The bearing 591 has a flange at an end of the cylinder so that the bearing 591 is fixed to the support chip 582A by bolts passing through holes formed on the flange. Outer rings of the bearings 592 and 593 are press-fitted into the inside of the cylinder of the bearing 591 so as to be separate in the axial line. A drive shaft 594 is supported by the bearings 592 and 593 rotatively relative to the bearing 591. The reduced diameter portion of the drive shaft 594 passes through the bearing 591.

An end section of the drive shaft 594 is enlarged in diameter substantially to that of the bearing 591. A coil spring 596 is wound around between an outer periphery of the drive shaft 594 and an outer periphery of a cylindrical section of the bearing 591. Terminals 596C and 596D are bent on both sides of the coil spring 596. A terminal 596C is engaged with a groove formed on the flange 594C formed at an end of the drive shaft 594. An elemental wire of the coil spring 596 is rectangular in cross section. The rectangular shape may be a square or a rectangle.

The drive shaft 594 is formed by a protrusion 594D and a flange 594C. A plurality of screw holes are formed around the protrusion 594D. Each rotative pin 597 is screwed into each screw hole disposed by 180 degrees offset in a circumferential direction. An inner ring of the bearing 598 is press-fitted and fixed into the protrusion 594D. A bearing 599 is attached to an outer periphery of the bearing 598. The bearing 599 has a cylindrical section 599D having a flange. Inserted in advance into the cylindrical section 599D is a ring retainer 600 that depresses the ring retainer 600 toward a drive shaft 594 with a preload screw 602 via a diaphragm spring 601. A plurality of through-holes 599C are formed on the flange of the bearing 599 at equal intervals in a circumferential direction. The through-holes 599C are disposed corresponding to the disposition of the screw holes of the drive shaft 594. The diameter of the through-hole 599C is greater than that of a head portion of the rotative pin 597. That is, the through-hole 599C has freeplay.

Provided further to cover the flange 594C of the bearing 594 and a coil spring 576 is a cylindrical cover 603. A notch 603C is formed on a base portion of the cover 603. The other terminal 596D of the coil spring 596 is hooked at the notch 603C. In addition, a cylindrical section 599D of the bearing 599 protruding from the cover 603 is fixed to the frames 580A by a pin.

Since an initial state of the coil spring 596 tightens the outer peripheries of the drive shaft 594 and the bearing 591, the drive shaft 594 is joined to the bearing 591 by the coil spring 596. Since the bearing 591 is fixed to the support chip 582A, the drive shaft 594 cannot rotate in the direction for tightening the coil spring 596. However, it is rotatable in a direction for loosening the coil spring 596. In contrast, a tilting movement provided by an operator of the operation stick 531A into the direction for tightening the coil spring 596 tilts the frames 580A that makes contact with the operation stick 531A. Tilting the frames 580A rotates the bearing 594 of the rotation shaft 584A and the cover 603. Rotating the cover 603 loosens the coil spring 596, thereby releasing the drive shaft 594 locked to the bearing 591. This results in allowing the drive shaft 594 to rotate, thereby transferring the rotation to a sprocket 595. The present symmetric disposition of the rotation shaft 585A with respect to the operation stick 531A transfers the rotational movement of the operation stick 531A but not the rotational movement for tightening the coil spring 596 from the sprocket 595. The operator's operation is transferred but a reaction force by the sprocket 595 is maintained when the operator stops the operation. Thus, the position is maintained, and the operation can be facilitated.

The coil spring 596 for use in such a spring clutch must be made from a high-hardness material. Use of a high-gravity material, e.g. iron, may cause an increase in the weight of the operation section 520. Therefore, a high-hardness and low-gravity material, e.g., duralumin (#2000) or extra super duralumin (#7000), may be used.

Meanwhile, loosening the coil spring 596 to release the locked state and transferring the rotation via the coil spring 596 inevitably provide an excessive force acting on the coil spring 596. In order to avoid such a state, a play is provided so that the head portion of the rotative pin 597 of the drive shaft 594 makes contact with a periphery wall of the through-hole 599C of the bearing 594 after releasing the locked state. Rupture of the coil spring 596 is prevented by transferring the rotation by means of the rotative pin 597. The spring clutch having such a configuration is not limited to the present embodiment and can be used for a rotative structure for the procedure instrument or for the overtube.

In addition, a drive shaft 584 protruding from the flange of the bearing 591 is supported by bearings 613 and 614 so as to be rotative with respect to a hollow shaft 612. The sprocket 595 is fixed to a hollow shaft 611. It should be noted that a rotative member for pushing and drawing a wire, e.g., a wire pulley, may be used in place of the sprocket 595.

The hollow shaft 612 is rotatively supported by the bearing 592 with respect to the bearing 591. The drive shaft 594 and the hollow shaft 612 both protruding over the sprocket 595 are inserted in a torque limiter 611. The torque limiter 611 includes an outer 611C fixed to the hollow shaft 612 and an inner 611D fixed to the drive shaft 594. The inner 611D and the outer 611C unitarily rotate until a predetermined torque is applied. When excessive torque is applied, the outer 611C slides on the inner 611D; and thus, the rotation is not transferred.

Figure 8:
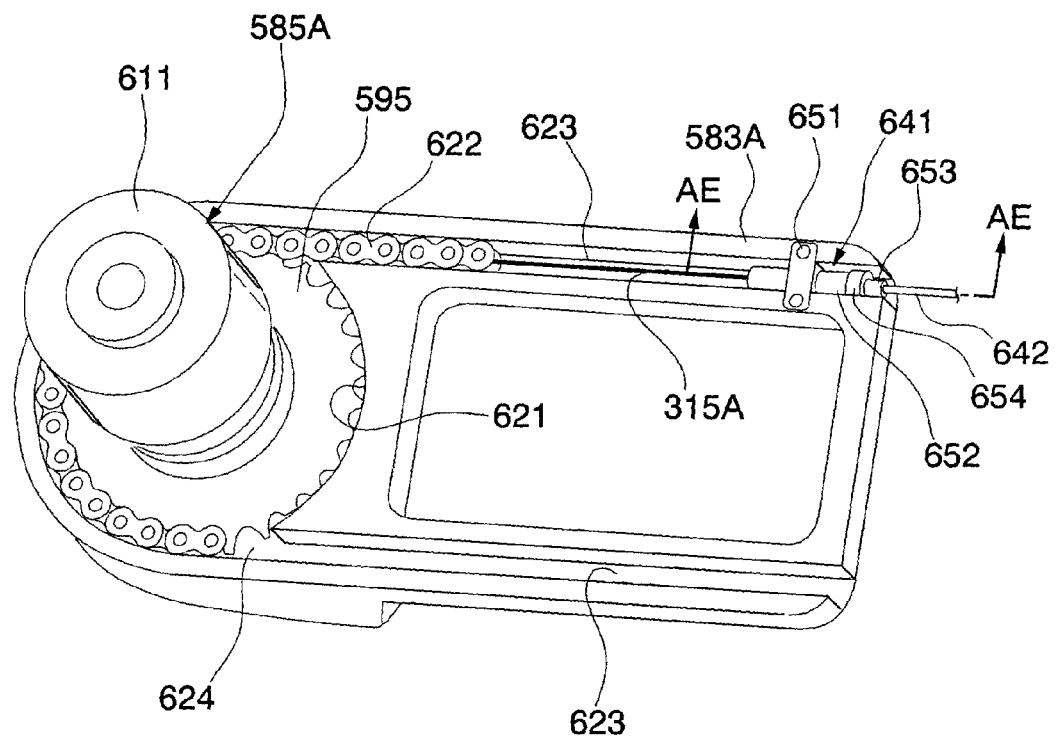
FIG. 8 is a perspective view for the other rotational axis, a support chip, and a bending wire.

As illustrated in FIG. 8 showing a configuration of the rotation shaft 585A, the sprocket 595 is rotatively housed in a circular recessing section 621 formed in the support chip 583A. A chain 622 is wound on teeth of the sprocket 595. A groove 623 is formed to the support chip 583A. An end part of the chain 622 can be drawn into a groove 623 that continues to the recessing section 621. The groove 623 is formed deeper than the recessing section 621. Providing a gap 624 between the groove 623 and the recessing section 621 prevents the chain 622 from being entangled between the sprocket 595 and the recessing section 621, thus guiding the chain 622 into the groove 623.

A first bending wire 315A is fixed to an end part of the chain 622. The first bending wire 315A bends the first bending parts 306 of the first arm members 302A illustrated in FIG. 1 in a right-hand direction.

Figure 9:
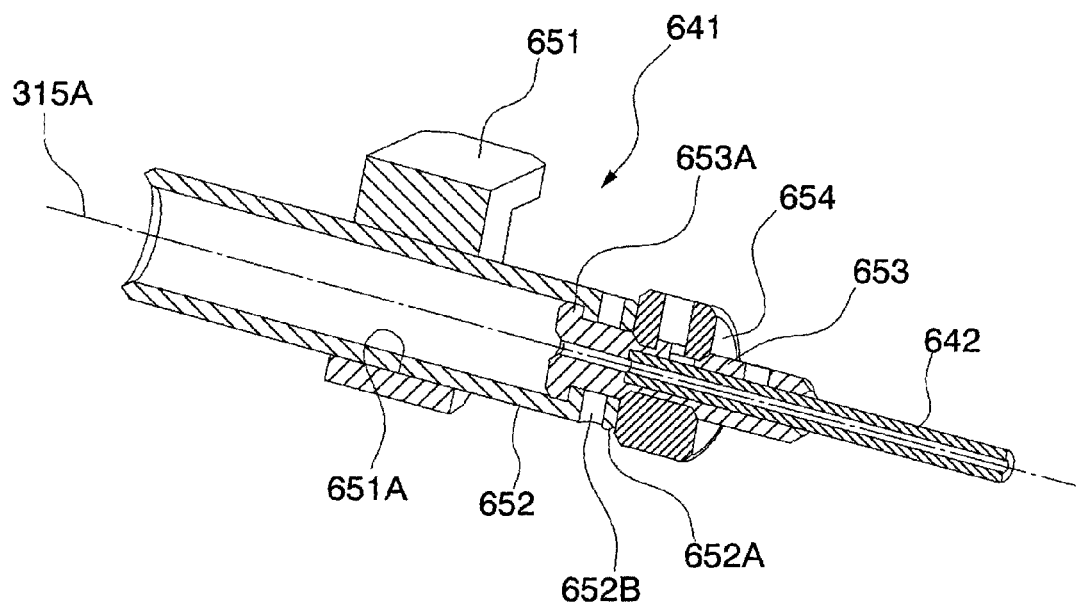
FIG. 9 is a cross-sectional view along the line AE-AE in FIG. 8.

As illustrated in FIG. 8, the first bending wire 315A is drawn into an adjuster 641 disposed at an end part of the groove 623 of the support chip 583A and introduced into a connection sheath 515 together with the coil sheath passing through a coil sheath 642 connected to the adjuster 641. The first bending wire 315A is finally reached to the first arm member 302A. As illustrated in FIGS. 8 and 9, the adjuster 641 has a coil base 651 fixed to the support chip 583A. A screw hole 651A is formed to the coil base 651. An adjustment shaft 652 having a thread on the outer periphery thereof is screwed into the screw hole 651A. The adjustment shaft 652 is a cylinder having a bottom. An end section 652A corresponds to the bottom part into which a coil stopper 653 is inserted. The removal of the coil stopper 653 is prevented by engaging a flange-shaped protrusion 653A with an inner surface of the end section 652A. Removal prevention in the reverse direction is provided by attaching a lock-screw 654 to the outer periphery. An end part of the coil sheath is fixed to the coil stopper 653. The first bending wire 315A passes through the adjustment shaft 652, followed by the coil stopper 653 and the coil sheath 642. The first bending wire 315A sometimes loosely extends during the step using the medical treatment endoscope 501. In this case, inserting a fixture into a hole 652B of the adjustment shaft 652 and rotating them cause the coil sheath 642 together with the adjustment shaft 652 to move in the axial direction. Forwarding the coil sheath 642 draws the first bending wire 315A from the coil sheath 642, thereby adjusting the loose state. Since the loose state can be adjusted by means of a screw, it is not necessary to dissemble the apparatus. Since the adjustment shaft 652 is rotatively engaged with the coil stopper 653, rotating the adjustment shaft 652 will never rotate the coil sheath 642.

Also, a sprocket 595 of the rotation shaft 584A is housed in the support chip 582A, and the chain 622 is wound around the sprocket 595. A first-bending wire which is not shown in the drawing is attached to the chain 622. The first bending wire 315A bends the first bending parts 306 of the first arm members 302A illustrated in FIG. 1 in a right-hand direction. An adjuster 641, also provided to the support chip 582A, can adjust the loose state by forwarding or drawing the coil sheath 642 having the first bending wire 315B therethrough. The first bending wire 315B inserted through the coil sheath 642 is introduced into the connection sheath 515 together with the coil sheath 642 and reached to the first arm member 302A.

As explained previously, the torque limiters 611 provided to the rotation shafts 584A and 585A prevent the rotation of the rotation shaft 585A from being transferred to the sprocket 595 when an excessive input is provided from the operation stick 531A. This results in preventing an excessive force from being applied to the first bending wire 315A. Considering a case assumed to use no torque limiter 611 may lead to a possibility where an excessive force is applied to the first bending wire 315A. The torque limiter 611 for controlling the maximum torque can prevent the first bending wire 315A from being fractured. In addition, disposing the torque limiter 611, the sprocket 595, and the rotation shafts 564A and 565A in this order from the outside shorten the distance between the support chips 582a and 583A, thereby downsizing the bracket 551A. This increases freedom in layout and contributes to a downsized and light-weight configuration.

The first rotation mechanism 561A will be explained next principally with reference to FIG. 5.

A rotation shaft 564A has a similar configuration to the rotation shaft 584A of the second rotation mechanism 581A except for the drive shaft 594 attachably engaged with the frame 567A via the rotative pin 597 in the rotative direction. Similarly, the other rotation shaft 565A has a similar configuration to the rotation shaft 585A of the second rotation mechanism 581A except for the drive shaft 594 attachably engaged with the frame 567A via the rotative pin 597 in the rotative direction.

Furthermore, a first bending wire 315D is joined to the sprocket 595 of one of the rotation shafts 564A via the chain 622. A first bending downward-operating wire 315D is joined to the sprocket 595 of one of the rotation shafts 564A via the chain 622. The first bending wire 315C and the bending wire 315D bend two first bending parts 306 of the first arm members 302A illustrated in FIG. 72 in vertical opening directions. The adjuster 641, also provided to the support chip 562A and 563A, can adjust the loose state by forwarding or drawing the coil sheath 642 having the first bending wires 315C and 315D therethrough.

Next, the operation stick 531A will be described.

Figure 10:
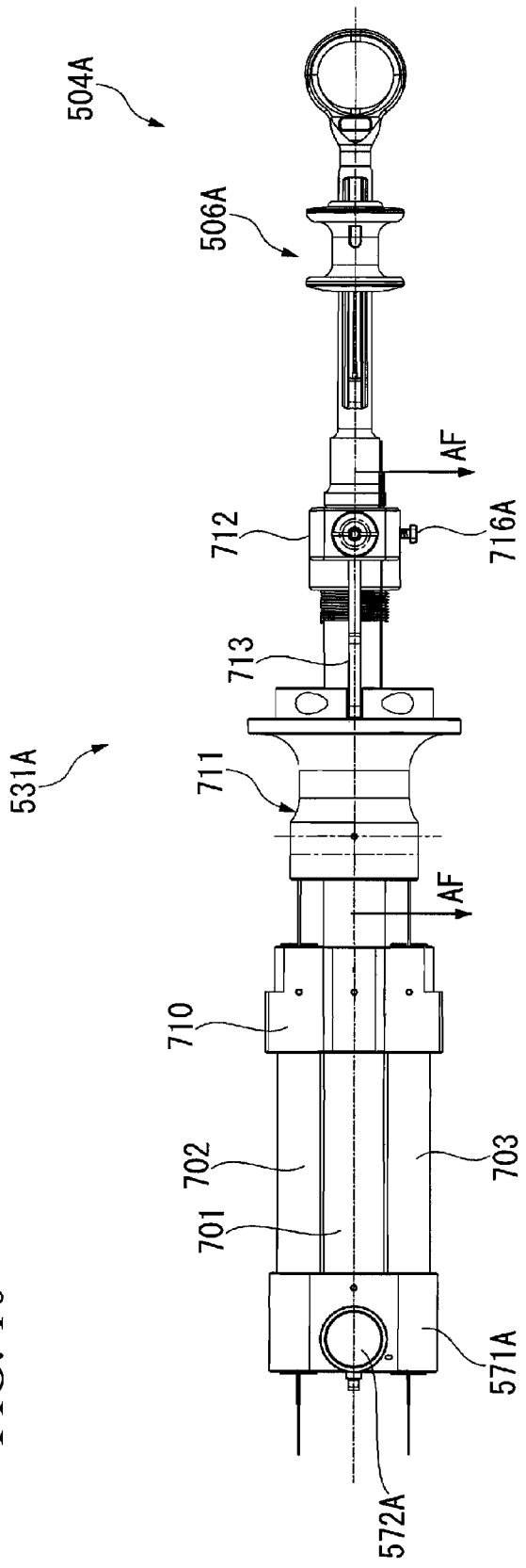
FIG. 10 is a plan view illustrating a first operation stick and a procedure instrument.

In the operation stick 531A as illustrated in FIGS. 5, 6, and 10, three cylindrical shafts 701, 702, and 703 bundled together are fixed to a tip portion to which a ball roller 572A is attached. The central shaft 701 is longer than two shafts, i.e., shafts 702 and 703. The other two shafts 702 and 703 barely reach to an abutment section 710 that serves as a rotative fulcrum making contact with the frame 567A of the first rotation mechanism 561A. In contrast, the central shaft 701 extends beyond an abutment section 710.

A second bending slider 711 capable of freely forwarding or retracting in the axial direction is attached to the central shaft 701. Furthermore, a ratchet base 712 is fixed to a base end of the shaft 701. In the initial state, the second bending slider 711 cannot be extended or retracted because the second bending slider 711 is joined to the ratchet base 712 by a connection plate 713 connected to the second bending slider 711.

Figure 11:
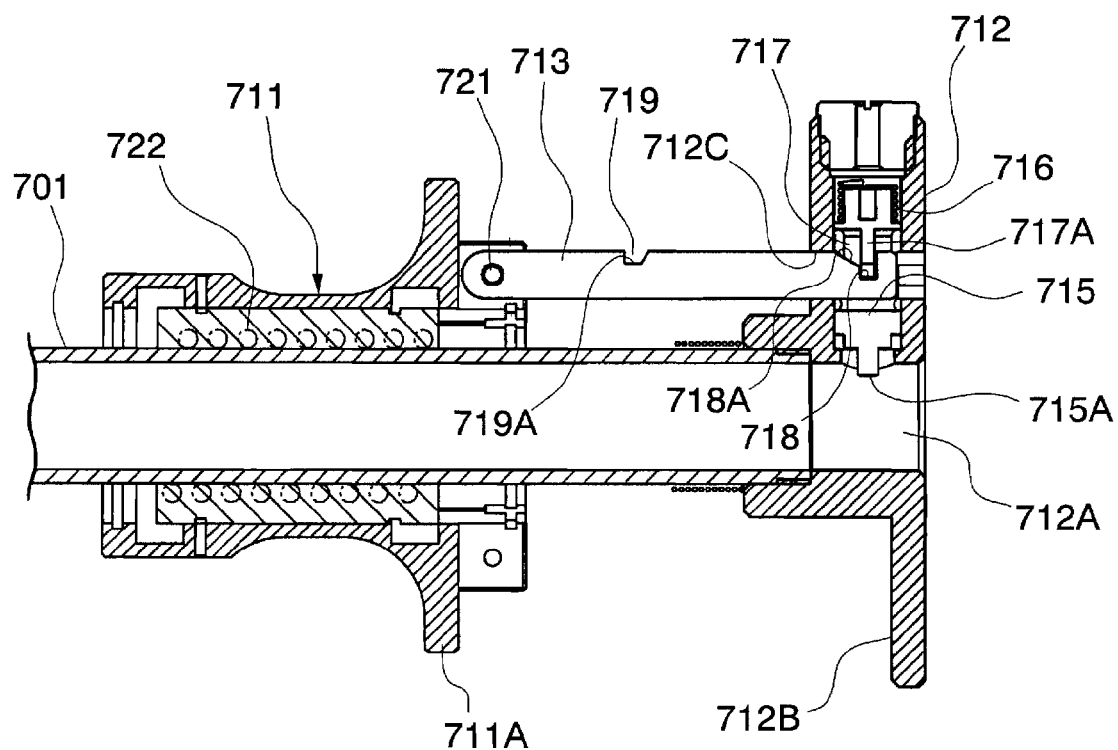
FIG. 11 is a cross-sectional view along the line AF-AF in FIG. 10 illustrating a pre-insertion state of the procedure instrument.
Figure 12:
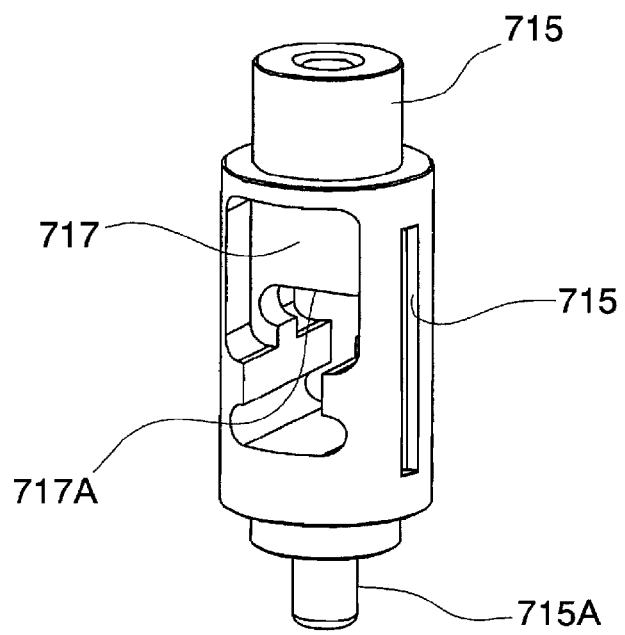
FIG. 12 is a perspective view for a piston.

As illustrated in FIG. 11, a through-hole 712A is formed in the center of the ratchet base 712. The through-hole 712A serves as an entrance from which the operation section 506A of the procedure instrument 504A is inserted. Furthermore, a part 712B of an outer periphery of the ratchet base 712 extends in a direction orthogonal to the axial line direction. Putting a thumb here allows the second bending slider 711 to be smoothly forwarded or retracted. A piston 715 slidable in a radial direction is housed in the ratchet base 712. The piston 715 is urged by a coil spring 716 in a radial direction orthogonal to the axial line direction. A protrusion 715A at the tip protrudes into a through-hole 712A that is an insertion path for the procedure instrument 504A. A slit 717 is formed on the piston 715. An engagement chip 717A is formed in the slit 717. A first groove 718 of the connection plate 713 is engaged with the engagement chip 717A. The first groove 718 is inserted through a slit 712C penetrating the ratchet base 712. Meanwhile, a vertical groove 717C that is parallel in a radial direction may be formed on the piston 715 as illustrated in FIG. 12. Inserting the tip portion of a clamping-bolt 716A (see FIG. 10) into a vertical groove 717C of an outer periphery of the ratchet base 712 can prevent the rotation of the piston 715. This prevents the piston 715 from galling the connection plate 713, thereby providing smooth movements of the piston 715 and the connection plate 713 as explained later.

Figure 23:
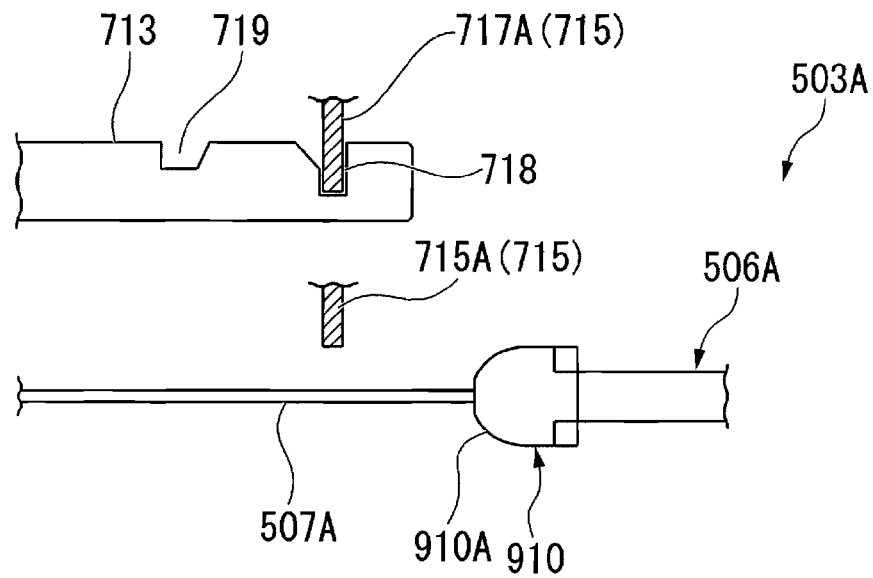
FIG. 23 illustrates motions provided by a cam, a piston, and a connection plate when the procedure instrument is inserted into the first operation stick.
Figure 25:
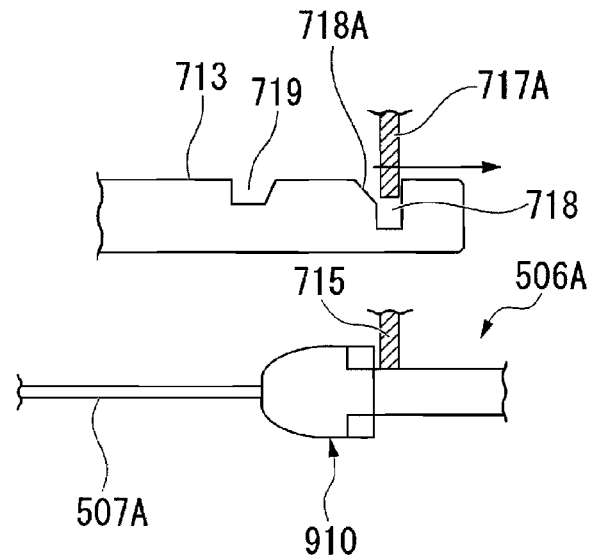
FIG. 25 illustrates the connection plate in a retractable state.
Figure 27:
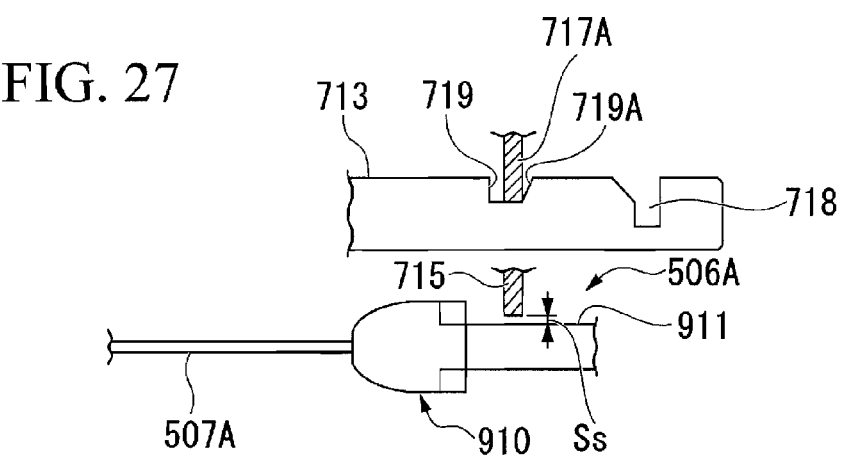
FIG. 27 illustrates an engaged state of the cam to a second groove.
Figure 28:
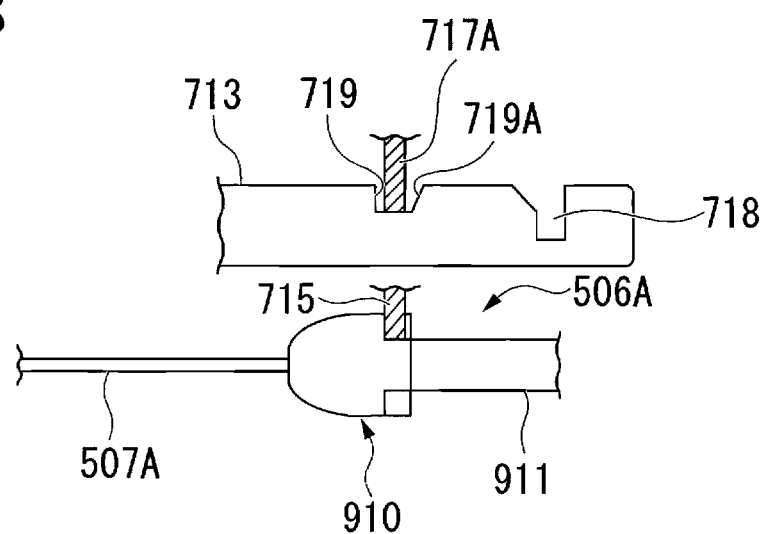
FIG. 28 illustrates the cam pushing up the piston when removing the procedure instrument.
Figure 29:
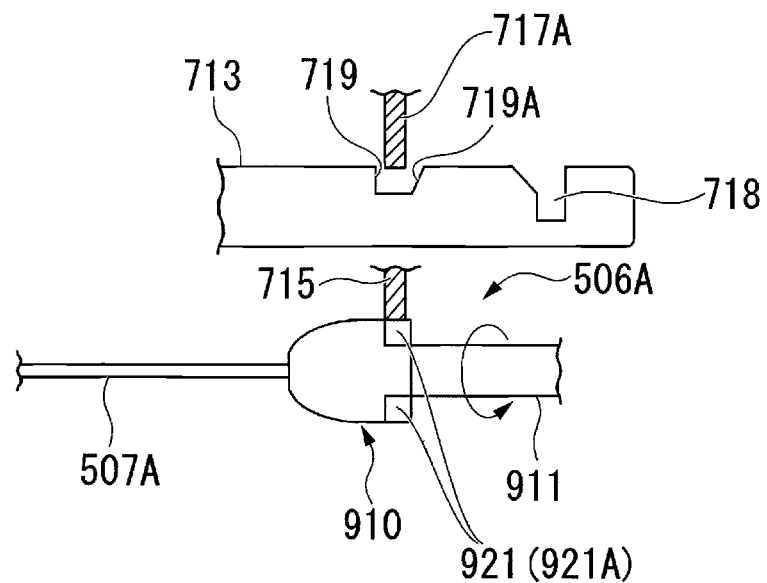
FIG. 29 illustrates the piston pushed up by rotating the cam.

The tip of the connection plate 713 is joined to the second bending slider 711 by a fulcrum pin 721 and extends substantially parallel in the axial line from here toward the ratchet base 712. The recessing shape of the first groove 718 allows the engagement chip 717A of the piston 715 to enter there, and a midpoint of the wall surface of the tip portion of the first groove 718 forms an inclination surface 718A. The inclination surface 718A gradually widens the first groove 718 from the midpoint to the tip portion. A second groove 719 is formed at a further tip portion than the first groove 718 is formed. The recessing shape of the second groove 719 allows the engagement chip 717A of the piston 715 to enter there. The second groove 719 is deeper than the first groove 718. The base end wall surface of the second groove 719 forms an inclination surface 719A. The inclination surface 719A gradually widens the second groove 719 toward the tip portion. The first groove 718 is positioned so that the second bending part 308 of the first arm member 302A as illustrated in FIG. 1 becomes straightened. The second groove 719 is positioned so that the second bending parts 308 bend to open the first arm member 302A. This allows the arm section 302A to close by engaging the first groove 718 with the piston 715, and allows a second arm member 303A to open by engaging the second groove 719 with the piston 715. As previously described, the engagement of the piston 715 with the grooves 718 and 719 can be released with a small force since the inclination surfaces 718A and 719A are formed in the grooves 718 and 719. This facilitates smooth switching of the engagement position of the piston 715 with the grooves 718 and 719. As illustrated in FIG. 23, a spring 791 forces the second bending slider 711 and the connection plate 713 to be positioned toward the tip portion by the spring force when the procedure instrument 504A is not inserted and thus, the first groove 718 engages with the piston 715. As illustrated in FIG. 25, the piston 715 is pushed by the operation section 506A of the procedure instrument 504A when the procedure instrument 504A is inserted. Since this state of the engagement chip 717A can move up the inclination surface 718A, the second bending slider 711 can be drawn, and the second bending part 308 can be opened. In this configuration, the procedure instrument 504A must be inserted to draw the second bending slider 711 because the tip of the procedure instrument 504A can hardly be passed through the opening state of the second bending part 308. As illustrated in FIG. 27, the engagement chip 717A makes contact with the inclination surface 719A as long as the second bending slider 711 is drawn toward the base end. The tension applied by second bending wires 316A and 316B urges the slider 711 toward the tip. As illustrated in FIGS. 28 and 29, raising the piston 715 necessitates a significant force if the disposition angle of the inclination surface 719A is significantly equal to 90°. If the disposition angle is substantially horizontal, the piston 715 is spontaneously raised by the tension applied by the second bending wires 316A and 316B and therefore, the second bending slider 711 moves toward the tip, and the second bending part 308 closes. The suitable angle α of the inclination surface 719 is $60° \leq \alpha < 90°$.

The second bending slider 711 is disposed coaxially with the axial line of the operation stick 531A. Therefore, the compact first operation unit 530A can be obtained. Formed at the base end thereof is an edge section 711A for putting a thumb. A linear stroke 722 is built in a portion making contact with the shaft 701 to provide smooth sliding movement on the shaft 701.

Figure 13:
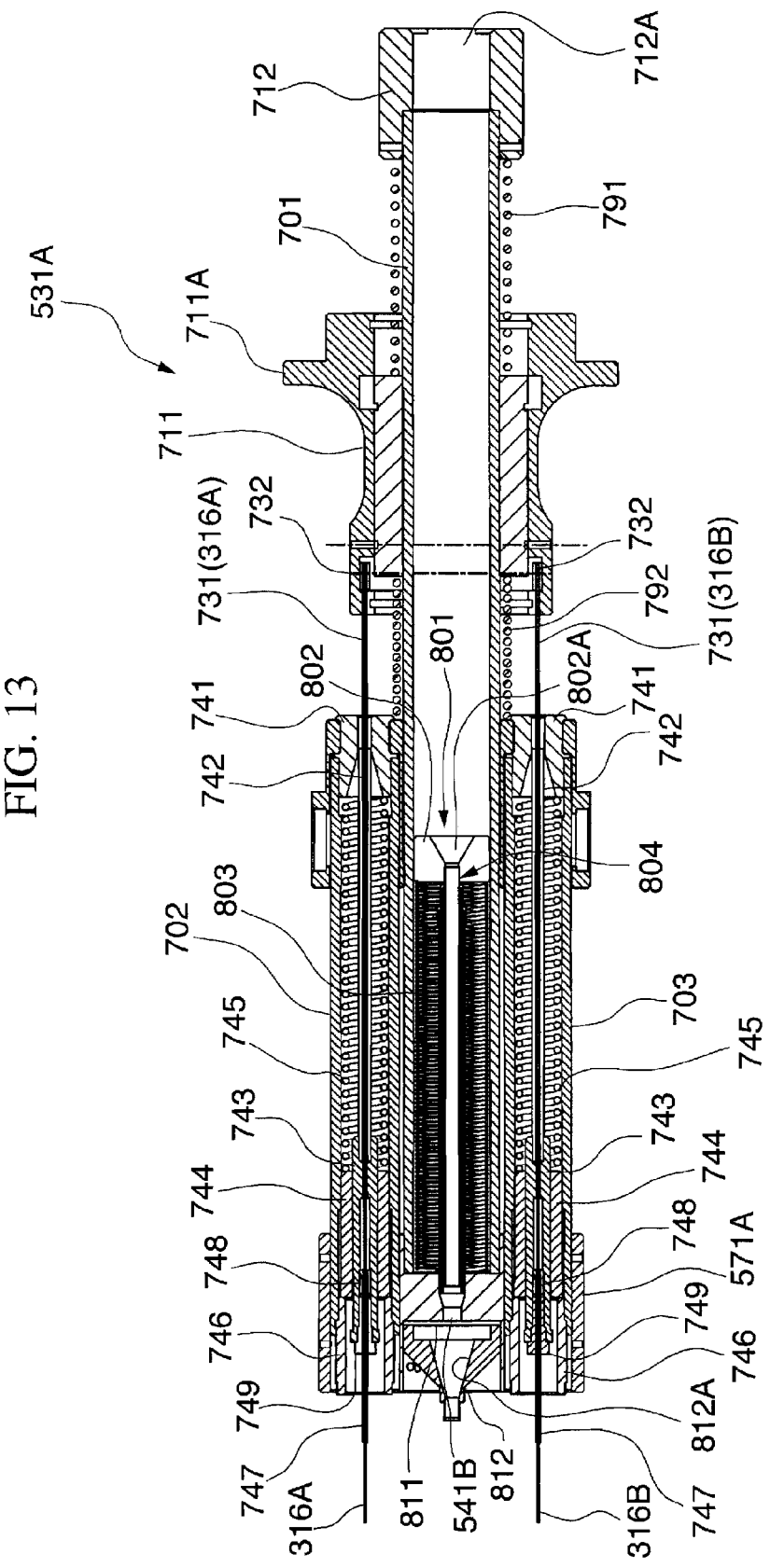
FIG. 13 is a cross-sectional view showing an enlarged state of a first operation stick illustrated in FIG. 6.

As illustrated in FIG. 13, two pipes 731 are attached to the tip of the second bending slider 711 so as to place the axial line between pipes 731. Second bending wires 316A and 316B are passed respectively through these pipes 731. The second bending wires 316A and 316B are fixed to an engagement member 732 in the second bending slider 711 so that the second bending wires 316A and 316B cannot be removed from the second bending slider 711. Disposing the second bending wires 316A and 316B symmetrically with respect to the second bending slider 711 equalizes the force applied to the second bending slider 711 and thus providing smooth movement thereof.

Two shafts 702 and 703, disposed further toward the tip, each have the pipe 731 inserted therethrough. The pipe 731 and the second bending wires 316A and 316B are inserted through the shafts 702 and 703 disposed side by side. The shafts 702 and 703 each have a retainer member 741 at the base end. Another pipe 742 is inserted from the tip through the retainer member 741. A pipe 731 and a second bending-wires 316A and 316B are passed through the pipe 742. The tip of the pipe 742 is supported by a coil-receiving casing 743. The coil-receiving casing 743 is screwed in the hole of a cylindrical pusher 744 and fixed there. An end portion of a coil spring 745 makes contact with the base end of the pusher 744. The other end portion of the coil spring 745 is butted against the retainer member 741. The pusher 744 is urged by the coil spring 745 toward the tip. In response to excessive force that draws the second bending wires 316A and 316B, a force that relatively moves a coil sheath 747 to an operator's hand is applied and thus, the coil spring 745 is compressed via the pusher 744. The coil spring 745 that is preset to a length exerting a predetermined force begins to contract if the preset force is overreached. Since the second bending wires 316A and 316B can further be drawn in accordance with the contraction of the coil spring 745, an excessive force is not applied to the second bending wires 316A and 316B. A force applied to the second bending wires 316A and 316B will never increase rapidly as long as the coil spring 745 can be contracted if an excessive force is applied and therefore, the second bending wires 316A and 316B will never be cut since overload mass is curbed. Meanwhile, the coil spring 745 is compressed by a pusher retainer 746 screwed from the tips of the shafts 702 and 703. Since the initial position of the pusher 744 can be adjusted in accordance with the compression mass of the pusher retainer 746, differences in rigidity and bending force based on the coil springs 745 can be adjusted.

Furthermore, only the second bending wires 316A and 316B are extracted from the pipe 742. The second bending wires 316A and 316B are inserted through the pusher retainer 746 in the coil-receiving casing 743 and introduced through the connection sheath 515 together with the coil sheath 747 to reach to the second bending part 308. The base end of the coil sheath 747 is brazed to a tubular coil receiver 748 and fixed there in the coil-receiving casing 743. A coil-receiver-retainer 749 is screwed from the tip through the coil-receiving casing 743. The coil-receiver-retainer 749 rotatively locking the coil receiver 748 prevents the coil sheath 747 from being removed from the coil-receiving casing 743, thereby preventing the pusher retainer 746 from being twisted. The lengths of the second bending wires 316A and 316B corresponding to the coil sheath 747 may sometimes have an assembly error, and such an error may sometimes be caused by the stretching of the second bending wires 316A and 316B. Adjusting the screwing amount of the coil-receiving casing 743 relative to the pusher 744 can correct the error.

Figure 14:
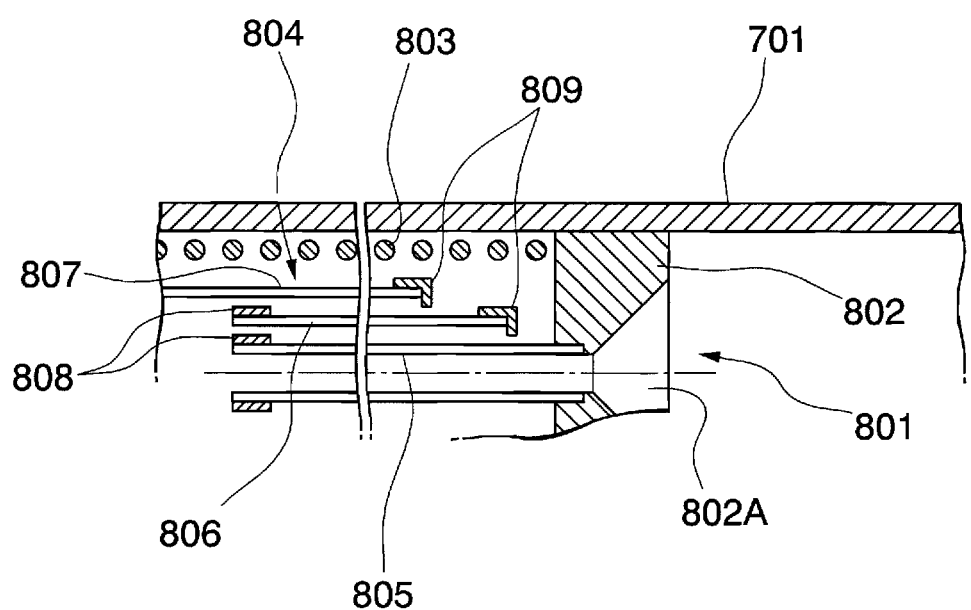
FIG. 14 shows a channel in magnified view.

As illustrated in FIGS. 13 and 14, a channel 801 for passing a procedure instrument 504A therethrough is built in the central shaft 701. The channel 801 has, in order from the base end, a retainer 802 that accommodates the procedure instrument 504A, a coil spring 803 inserted between the retainer 802 and the tip section 571A, and an extendable pipe 804 disposed in the coil spring 803. A hole 802A is formed in the center of the retainer 802. The hole 802A serves as an entrance for inserting the procedure instrument 504A therefrom. The hole 802A is a tapered hole where the opening diameter increases toward the base end. The hole 802A having a funnel shape facilitates the insertion of a distal end of an insertion section 507A of the procedure instrument 504A. The extendable pipe 804 has three pipes 805, 806, and 807 each of which are different in diameter. These pipes are disposed coaxially. A removal stop 808 is attached to the pipes 805 and 806. A stopper 809 locked to the removal stop 808 is attached to each pipe 806 and 807. That is, the extendable pipe 804 becomes the shortest when three pipes 805, 806, and 807 substantially overlap. Extending each pipe 805, 806, and 807 and locking the stopper 809 to the removal stop 808 allows the extendable pipe 804 to be the longest. While the drawings illustrate the compressed state of the coil spring 803, the coil spring 803 restores under the no-load condition. The retainer 802 moves to the vicinity of a shaft 701 and to the vicinity of the distal end of the piston 715. Since the retainer 802 is disposed at the base end of the shaft 701 unless the procedure instrument 504A is not inserted, the insertion section 507A of the procedure instrument 504A can be inserted easily. The retainer 802 is pushed by the tip portion of the operation section 506A of the procedure instrument 504A to be forwarded to the position illustrated in FIG. 13 when the procedure instrument 504A is inserted. It should be noted that the extendable pipe 807 is not limited to a triple-pipe structure.

A space for passing the procedure instrument 504A therethrough is provided in a tip section 571A that joins three shafts 701, 702, and 703. An airtight valve 811 is provided on a path into which the procedure instrument 504A is inserted and thus, the airtight condition inside of the body subjected to a medical operation can be maintained even if the procedure instrument 504A is removed during the medical operation. The airtight valve 811 is made of, for example, a rubber sheet disposed to seal a hole 571B that communicates with the shaft 701. Formed to the rubber sheet is a notch into which an insertion portion of the procedure instrument 504A can be inserted. Passing the procedure instrument 504A therethrough necessitates opening the notch. Removing the procedure instrument 504A closes the notch, thereby maintaining the airtight condition. A retainer 812 is used to fix the airtight valve 811. Fixing the retainer 812 onto the tip section 571A by screws facilitates exchanging the airtight valve 811 made of a rubber sheet. Meanwhile, the procedure instrument 504A is introduced into the body through a hole 812A formed in the retainer 812. Forming a hole 812A so as to be tapered toward the tip facilitates the insertion of the procedure instrument 504A.

The configuration of the second operation unit 530B is explained.

The second operation unit 530B has a symmetric configuration to the first operation unit 530A with respect to the horizontal center line of the operation section 520. A symbol "B" is added to some components included in the operation unit 530B to distinguish them from those of the first operation unit 530A.

A procedure instrument 504A inserted through the operation section 520 will be explained next. Although only the procedure instrument 504A will be explained here, it should be noted that the procedure instrument 504B has the same configuration. An end of each procedure instrument 504A and 504B may be a high-frequency knife, a puncture needle, a snare, a clip, or additional forceps.

Figure 15:
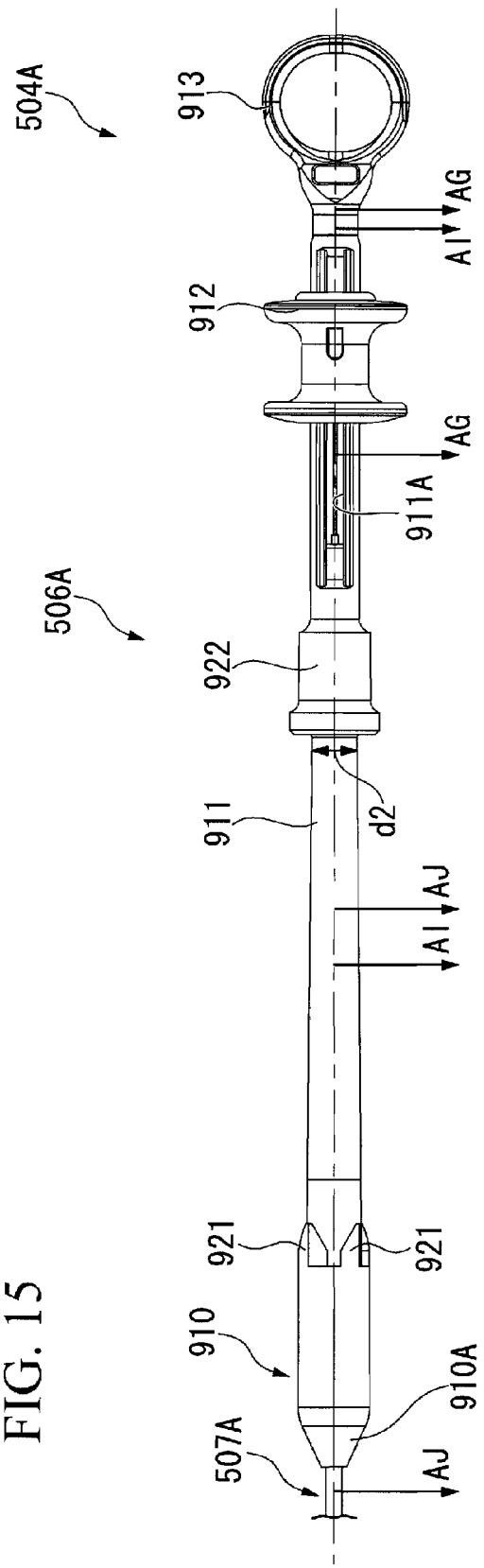
FIG. 15 is a plan view illustrating a procedure instrument.

As illustrated in FIG. 15, a treatment section 505A (see FIG. 1) and an operation section 506A both provided to the tip of the procedure instrument 504A are joined by an elongated flexible insertion section 507A. The operation section 506A has a main body section 911 having a cam 910 at the tip thereof. A slider 912 that drives the treatment section 505A is attached at the base end of the main body section 911 rotatively in the axial line direction. In addition, a finger-hook ring 913 is attached to the base end of the main body section 911.

Figure 16:
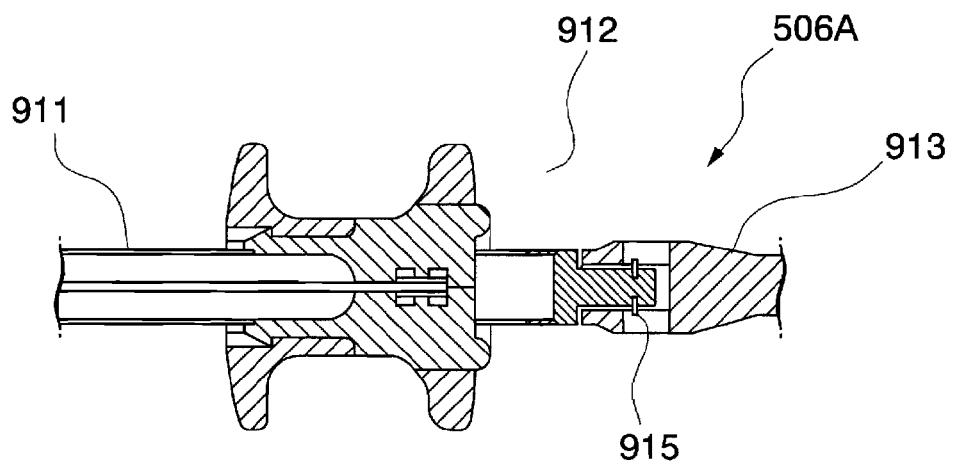
FIG. 16 is a cross-sectional view along the line AG-AG in FIG. 15.
Figure 17:
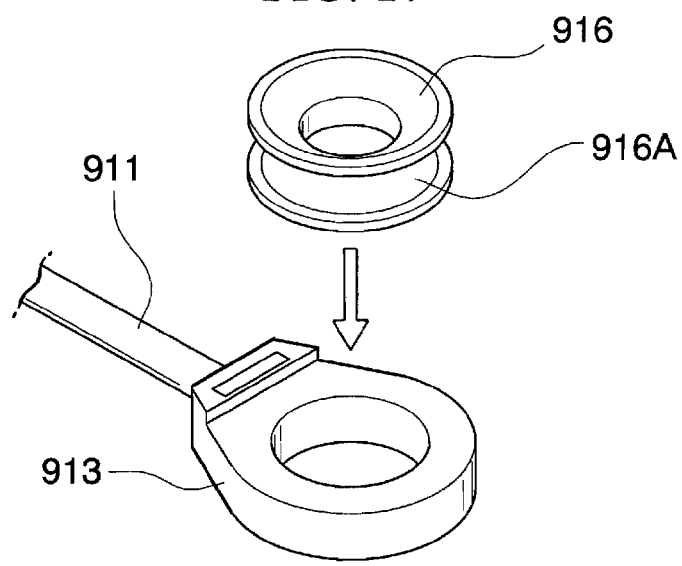
FIG. 17 describes how to attach a protection member to a ring.
Figure 18:
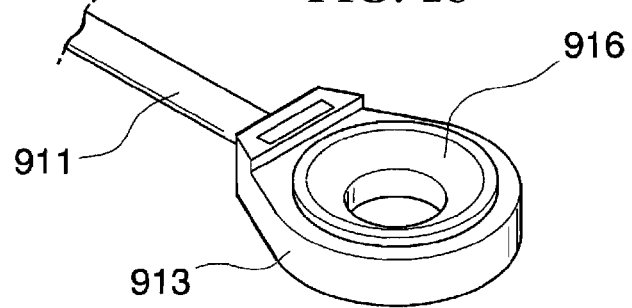
FIG. 18 describes a post-attached protection member disposed to the ring.

As illustrated in FIG. 16, a ring 913 is joined to the main body section 911 via an E ring 915. Operability is desirable since the ring 913 can be rotated by the E ring 915 around the axial line. It should be noted that a rubber-made protection member 916 may be used to be fitted to the inside of the ring 913 as illustrated in FIGS. 88 and 89. A groove 916A detachable from the ring 913 is formed on an outer periphery of the protection member 916. The use of rubber eases pain on fingers during operation. In addition, a detachable configuration is superior in maintaining cleanliness and sterilization. Making the protection member 916 of for example, a silicone rubber, imparts chemical resistance and sterilization.

Figure 19A:
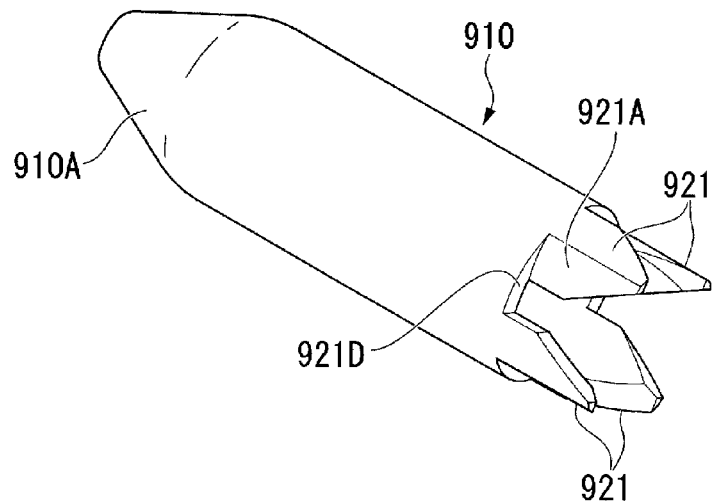
FIGS. 19A and 19B illustrate a cam in a perspective view.

As illustrated in FIGS. 5 and 15, the tip portion of the cam 910 is a taper where an opening diameter decreases. When a taper surface 910A is inserted through the operation stick 531A, the taper surface 910A serves for pushing up the piston 715 and pressing the channel 801. The outer diameter of the cam 910 is substantially the same as the inner diameter of the shaft 701 so that the cam 910 is slidable on the shaft 701. Four blade sections 921 extending in the axial line direction are provided to the base end of the cam 910. As illustrated in FIG. 19A, each blade section 921 is provided only on the outer periphery of the cam 910. A side surface 921A in the circumferential direction forms a tilted and curved surface from the center toward radially outward.

Figure 19B:
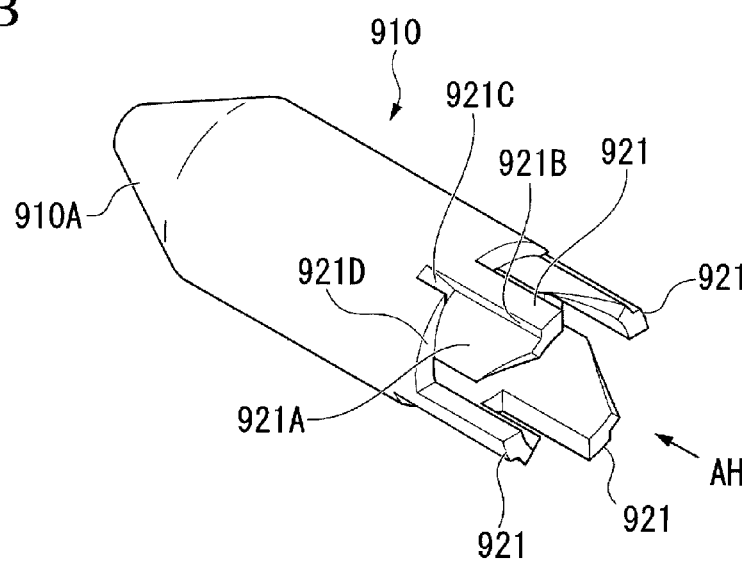
Figure 20:
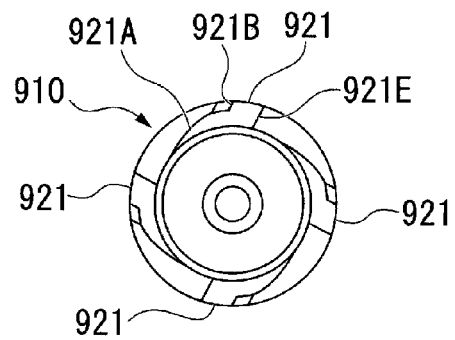
FIG. 20 is a view on arrow AH in FIG. 19.

In addition, as illustrated in FIGS. 19B and 20, a slope 921C directed to the tip together with a gap surface 921B standing in a radial direction may be formed on the outer periphery of the tilted side surface 921A of the cam 910. A gap 921D between the tilted side surface 921A and the outer periphery of the cam 910 is smoothly resolved by the slope 921C. A side surface 921E disposed opposite to the side surface 921A in the blade section 921 has a space greater than the diameter of the piston 715 between the side surface 921A of another blade section 921 adjacent in the circumferential direction and the side surface 921E. The side surface 921E is tilted in the direction the same as the tilting direction of the side surface 921A. The tilting direction of the side surface 921E is significant, i.e., forms a steep surface.

A main body section 911 is screwed into an inner hole of the cam 910 and fixed there. The outer diameter of the main body section 911 including a part inserted into the cam 910 and a stopper 922 having an increased diameter may be reduced gradually toward the base end. That is, FIG. 15 shows an example in which a diameter d2 at the base end is smaller than the diameter d1 at the tip. An operation section 506A of the hole 571B has a play relative to the operation stick 531A to prevent the main body section 911 from pushing up the piston 715 even if the operation section 506A is tilted or bent. Also, the tip of the piston 715 protruding into the shaft 701 is configured to have a correlation with the second groove 719 so that a space is formed between the piston 715 and the second groove 719. Thus, the piston 715 is prevented from interfering with the main body section 911 and therefore, the forward movement or retracting movement of the procedure instrument 504A can be smooth. In addition, the stopper 922 makes contact with a ratchet base 712 when the procedure instrument 504A is inserted through the operation stick 531A and regulates the procedure instrument 504A to prevent it from being pushed further.

Figure 21:
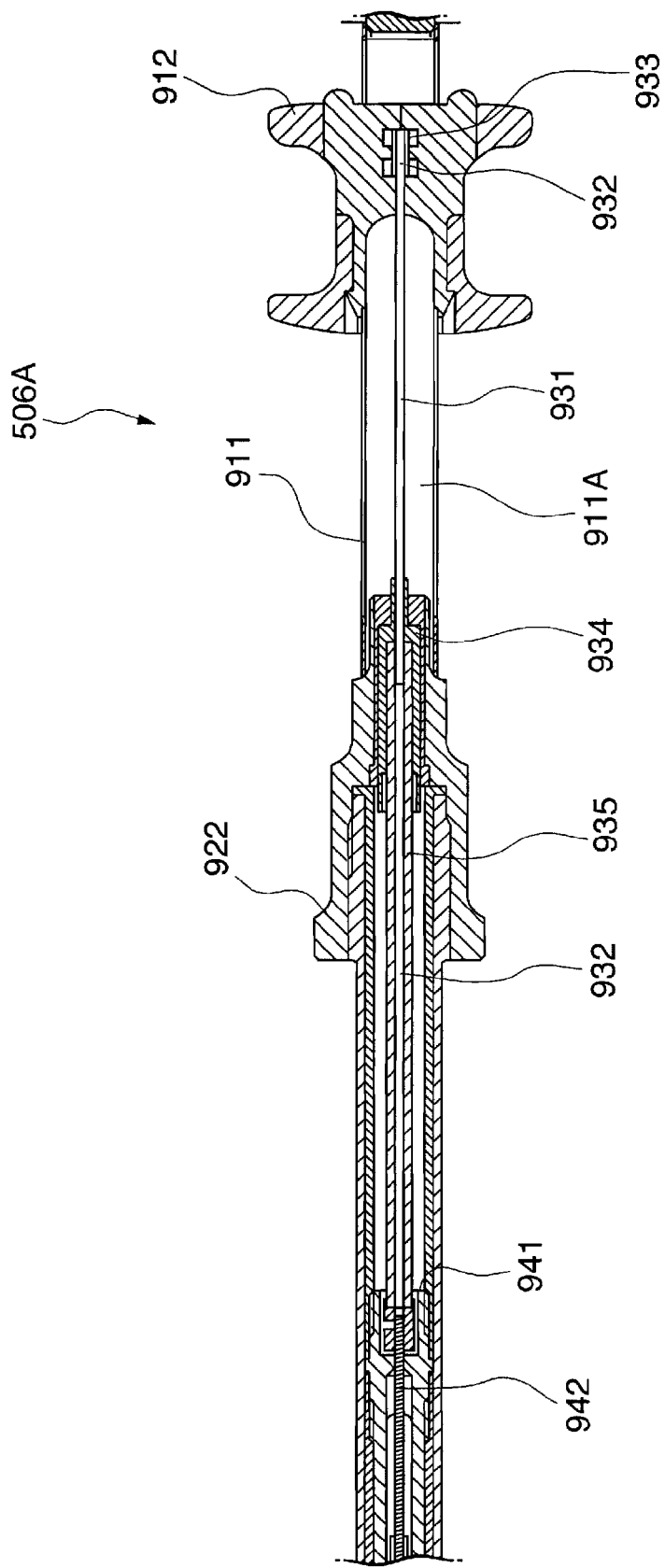
FIG. 21 is a cross-sectional view along the line AI-AI in FIG. 15.

As illustrated in FIG. 21, a pipe 931 is fixed to a slider 912. An operation wire 932 for driving the treatment section 505A is passed through the pipe 931. The base end of the operation wire 932 and the base end of the pipe 931 are locked to the slider 912 by an engagement member 933. The pipe 931 passing through a slit 911A of the main body section 911 is extendably supported by a resin-made pipe retainer 934. An operation wire 932 passing through another pipe 935 fixed to the pipe retainer 934 is extracted and enters an intermediate coupling 941 together with the pipe 935, and is inserted into a metal-made single-layered coil 942 therein. Isolation is imparted to the pipe 935 by coating it with a thermally-contracting tube.

Figure 22:
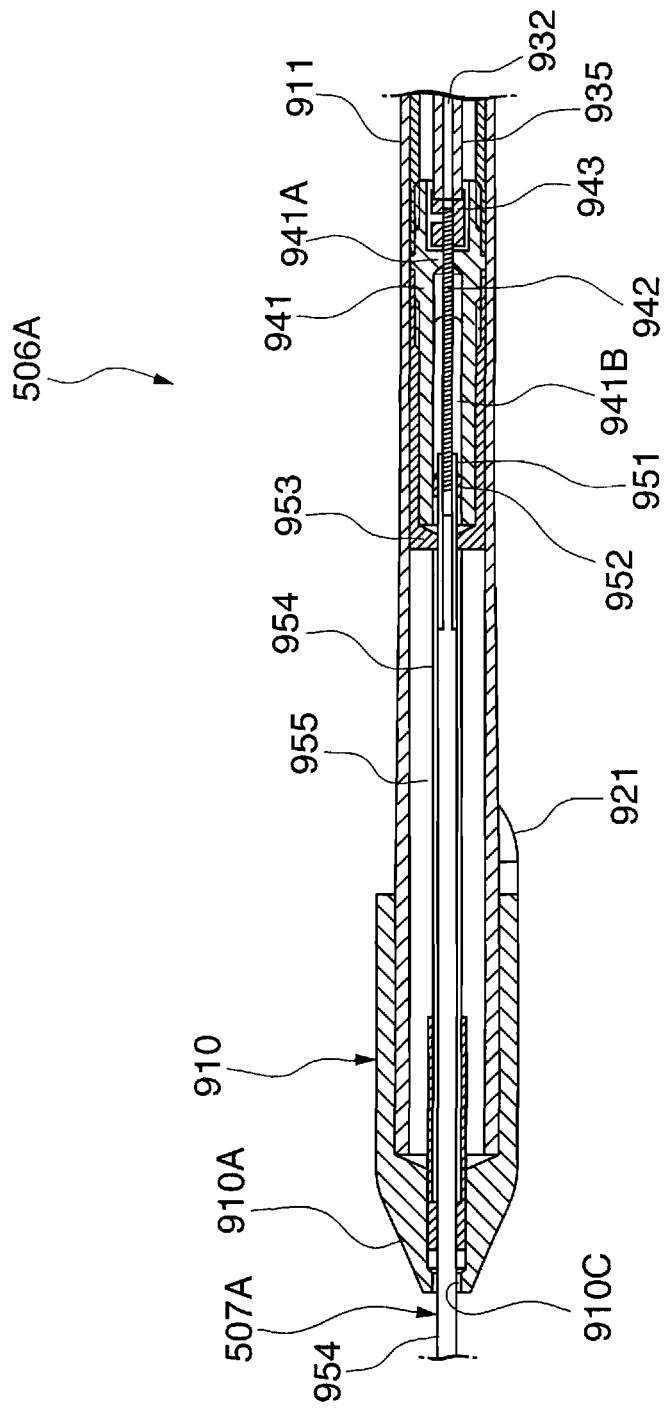
FIG. 22 is a cross-sectional view along the line AJ-AJ in FIG. 15.

As illustrated in FIG. 22, a coil receiver 943, to which the base end of the single-layered coil 942 is fixed, is housed in the base end of the intermediate coupling 941. The tip of the previously described pipe 935 is inserted into the coil receiver 943. A diameter-contracting section 941A is provided to the intermediate coupling 941 to prevent the coil receiver 943 from being removed toward the tip. The single-layered coil 942 is inserted into a multi-layered coil 951 farther toward the tip than the diameter-contracting section 941A. The multi-layered coil 951 is configured to have more than three coils disposed coaxially. For example, an innermost layer coil and an outermost layer coil are wound in the same direction, and an intermediate-layer coil is wound in the opposite direction in the case of a three layer structure. This results in that rotating of the innermost layer coil and the outermost layer coil in the coil-loosening direction tightens the intermediate-layer coil, thereby causing the intermediate layer coil to interfere with the innermost layer coil. Thus, the rotation torque is transferred to the treatment section 505A at the tip. Rotating in the opposite direction causes the loosening intermediate layer coil to interfere with the outermost layer coil, thereby transferring the rotation torque to the treatment section 505A. In addition, using a metal-made multi-layered coil 951 improves the transferred rotation torque. A resin-made coil may be used for obtaining insulation.

A coil receiver 952 is brazed to the multi-layered coil 951. The coil receiver 952 is slidably inserted through a longitudinal groove 941B formed on the insulative intermediate coupling 941. Accordingly the multi-layered coil 951 can engage with the intermediate coupling 941 in the rotative direction, but not in the forward direction or the retracting direction. Meanwhile, a resin-made removal stop 953 is attached to the tip of the intermediate coupling 941. Since the removal stop 953 regulates the protrusion of the coil receiver 952, the multi-layered coil 951 will never be removed from the intermediate coupling 941. Also, the coil receiver 952 will never make contact with the main body section 911. This configuration will not affect the length of the multi-layered coil 951 even if the single-layered coil 942 contracts or extends during a medical operation.

Also, the single-layered coil 942 can be brazed to the coil receiver 943 that is slid toward the base end and extracted from the intermediate coupling 941 after brazing the multi-layered coil 951 to the coil receiver 952. Meanwhile, the intermediate coupling 941 should preferably be made of high heat-resistance resin, e.g., PEEK (polyetheretherketone) taking the high temperature applied during the brazing operation into account.

The outer periphery of the multi-layered coil 951 extracted from the intermediate coupling 941 is coated by an insulative tube 954. A fluoro resin-made insulative tube 954 has lower sliding friction, thus providing desirable rotation. The isolated and coated multi-layered coil 951 passing through a winding-protection pipe 955 is extracted from a hole 910C formed at the tip of the cam 910.

The main body section 911 should preferably be made of a metal material taking durability into account. In this case, providing insulation to the operation section 506A realizes a procedure instrument 504A for use in a medical operation with a high-frequency apparatus. Therefore, the use of a resin in the removal stop 953, intermediate coupling 941, thermally-contracting tube of the pipe 935, pipe retainer 934, and slider 912 reliably isolates the main body section 911 from the operation wire 932 and coils 942 and 951. This results in using high-frequency waves with the procedure instrument 504A such as an incision knife or high-frequency forceps. Apparatuses of this type can be used compatibly. Insulation coating onto the multi-layered coil 951 may not be necessary unless the procedure instrument is of a high frequency application-type apparatus. In this case, increasing the thickness of the multi-layered coil 951 corresponding to the thickness of the thermally contracting tube for use as a coating will provide a more rotative procedure instrument. The thickness of the thermally contracting tube utilized for the single-layered coil 942 will provide significantly more resistance against compression or expansion.

Consequently, steps for carrying out operations using the medical treatment endoscope 501 will be explained. Meanwhile, a case will be explained as follows where an endoscope is introduced from a mouth as a natural orifice of a patient, a procedure instrument is introduced from an opening formed in a stomach into an abdominal cavity to grasp tissue. It should be noted that operations can be carried out through another organ or another path. Although we concentrate on the procedure instrument 504A and the first operation unit 530A in the explanation, the procedure instrument 504B and the operation unit 530B can be used independently because they are mere symmetric components.

Figure 24:
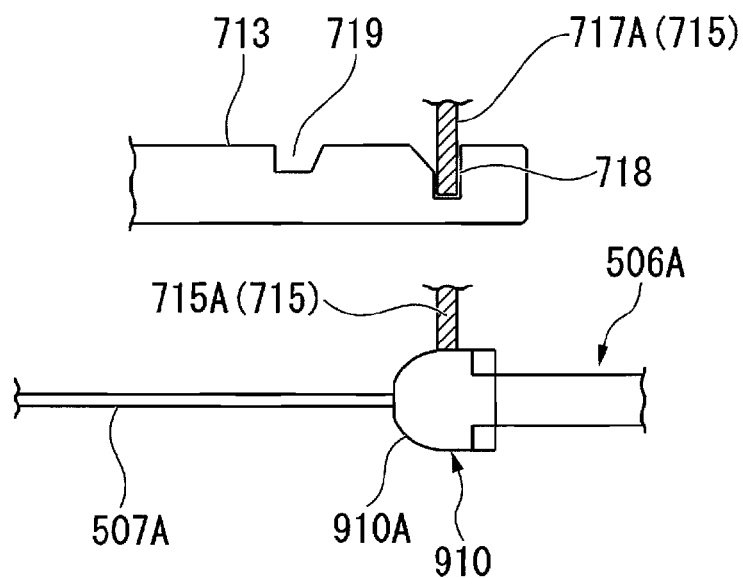
FIG. 24 illustrates the piston pushed up by the cam.

Two procedure instruments 504A and 503B are inserted into the medical treatment endoscope 501. The procedure instrument 504A is inserted into the first operation unit 530A. As schematically illustrated in FIG. 23, when the procedure instrument 504A is not inserted yet, the piston 715 provided to the ratchet base 712 at the tip of the first operation stick 531A engages with the first groove 718 of the connection plate 713 and locks the connection plate 713. Locking the connection plate 713 prevents the second bending slider 711 from moving since the ratchet base 712 is unmovable. This corresponds to a position where the second bending part 308 becomes straightened. That is, the second bending part 308 is always straightened in the medical treatment endoscope 501 when the procedure instrument 504A is inserted. As illustrated in FIG. 24, forwarding the operation section 50A into the first operation stick 531A pushes up the piston 715 with the taper surface 910A of the cam 910 at the tip of the operation section 506A. As illustrated in FIG. 25, the piston 715 being capable of moving up the inclination surface 718A of the first groove 718 of the connection plate 713 allows the second bending slider 711 to be controlled in the direction indicated by an arrow shown in the drawing.

As illustrated in FIG. 5, the insertion section 507A of the procedure instrument 504A passing through the channel 801 is introduced into a channel in the connection sheath 515. The insertion section 57A further passing through the endoscope insertion section 503 is introduced to the tip of the first arm member 302A. Similarly, the procedure instrument 504B inserted into the operation stick 531B of the operation unit 530B is disposed at the tip of the second arm member 303A.

After closing the arm sections 302A and 303A having the procedure instruments 504A and 504B previously passing therethrough, the endoscope insertion section 503 is introduced into a body cavity from an opening previously formed in a stomach wall. In addition, the endoscope insertion section 503 may be passed through an overtube previously inserted into a body.

A section to be treated is confirmed while observing with a monitor an image obtained by an endoscopic image-pickup device provided to the tip of the endoscope insertion section 503. At this time, a first operator manipulates an angle knob 512 of the endoscope insertion section 502 and bends a third bending part 203B. Furthermore, a second operator bends the second bending part 308 and the first bending part 306 if necessary.

Figure 26:
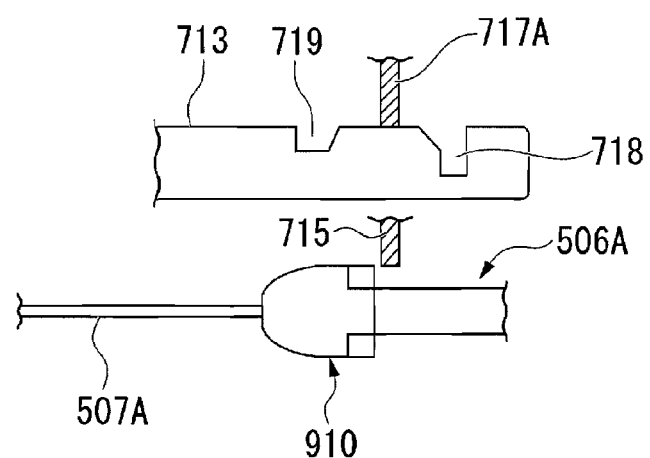
FIG. 26 illustrates the cam disposed between two grooves of the connection plate.

Bending the second bending part 308 necessitates retracting the second bending slider 711 provided to the operation sticks 531A and 531B. As illustrated in FIG. 25, retracting the second bending slider while the piston 715 is elevated causes the engagement chip 717A of the piston 715 to go up the inclination surface 718A, thereby causing the connection plate 713 to slide on the piston 715 as illustrated in FIG. 26. The second bending slider 711 which cannot be farther retracted after the piston 715 is housed in the second groove 719 as illustrated in FIG. 27. The second bending part 308 as illustrated in FIG. 1 bends at this position, causing the first arm member 302A to open. In addition, since the second groove 719 is shallower than the first groove 718, a space Ss is formed between the cam 910 and the main body section 911 of the operation section 506A when the piston 715 engages with the second groove 719. Absence of sliding friction between the main body section 911 and the piston 715 allows smooth extension and retraction of the main body section 911.

Furthermore, bending the first bending part 306 necessitates tilting the operation sections 506A and 506B of the procedure instruments 504A and 504B while observing the endoscopic image.

As illustrated in FIG. 4, tilting the operation section 506A upward relative to the operator causes the rotation shafts 564A and 565A of the first rotation mechanism 561A to rotate in accordance with the tilting angle. The rotation of the sprocket 595 attached to the rotation shafts 546A and 565a causes extension and retraction of the first bending wires 315A and 315B attached to the chain 622, thereby bending the first bending part 306 upward. In contrast, tilting the operation section 506A downward relative to the operator causes the rotation shafts 564A and 565A of the first rotation mechanism 561A to rotate in the direction reverse to the upward tilting direction in accordance with the tilting angle. The reverse rotation of the sprocket 595 attached to the rotation shafts 546A and 565a causes extension and retraction of the first bending wires 315A and 315B attached to the chain 622, thereby bending the first bending part 306 downward.

Tilting the operation section 506A in a right-hand direction relative to the operator causes the rotation shafts 584A and 585A of the second rotation mechanism 581A to rotate in accordance with the tilting angle. The rotation of the sprocket 595 attached to the rotation shafts 584A and 585A causes extension and retraction of the first bending wires 315C and 315D attached to the chain 622, thereby bending the first bending part 306 in the right-hand direction. In contrast, tilting the operation section 506A in a left-hand direction relative to the operator causes the rotation shafts 584A and 585A of the second rotation mechanism 581A to rotate in the reverse direction in accordance with the tilting angle. The rotation of the sprocket 595 attached to the rotation shafts 584A and 585A causes extension and retraction of the first bending wires 315C and 315D attached to the chain 622, thereby bending the first bending part 306 in the right-hand direction.

Since the second rotation mechanism 581A is not driven when the first rotation mechanism 561A is driven, and the first rotation mechanism 561A is not driven when the second rotation mechanism 581A is driven, each bending can be obtained without being affected by these rotation mechanisms. Meanwhile, tilting the operation section 506A drives the first and second rotation mechanisms 561A and 581A in accordance with the tilting ratio with respect to the vertical and horizontal directions, thereby bending the first bending part 306 diagonally in a direction the same as the tilting direction of the operation section 506A. Since the center or barycenter of the operation stick 531A in the longitudinal direction is configured to substantially coincide with the positions of the rotation shafts 546A, 565A, 584A, and 585A, the operation stick 531A and the operation section 506A of the procedure instrument 504A during hands-free operation by the operator will not descend with gravity; therefore, erroneous operation can be prevented.

A necessary force is optimized to operate the first bending part 306 by means of a non-electric wire-assisted operation. To be more specific, a portion of the operation stick 531A operated by the operator who inputs a force is decelerated by separating and offsetting the portion from the rotation shafts 546A, 565A, 584A, and 585A. As illustrated in FIG. 6, since a deceleration ratio corresponding to a ratio between a distance Lr an a radius Rs of the sprocket 595 is obtained, the bending operation can be carried out with a small force while downsizing the operation section 520. In this case the distance Lr indicates the length between the base end section of the operation section 506A of the procedure instrument 504A. In addition, the deceleration enhances resolution, thereby enabling accurate bending operation.

As illustrated in FIGS. 5 and 6, since the point of the second rotation mechanism 581A to which a force is transmitted from the first operation stick 531A is offset toward the tip relative to the rotation shafts 564A and 565A such as a roller bearing 572A as illustrated in FIG. 6, the force necessary at the transfer position is decreased, and friction among components can be reduced. This decreases the rigidity required for components used there and obtains a small and light-weight operation section 520. Also, the use of the ball roller 572A at the point of the second rotation mechanism 581A to which the force is transferred from the first operation stick 531A reduces the friction due to the second rotation mechanism 581A when rotating the first operation stick 531A vertically, thereby reducing the necessary force for the vertical operation.

Grasping tissue necessitates adjusting the position of a forceps member that is opened or closed by the operation section 506A of the procedure instrument 504A. For example, pushing the operation section 506A into the first operation stick 531A causes the treatment section 505A to protrude further from the first arm member 302A. Also, retracting the operation section 506A from the first operation stick 531A causes the treatment section 505A to be retracted into the first arm member 302A. As illustrated in FIG. 28, since this state of the cam 910 is hooked on the piston 715, the procedure instrument 504A will not be undesirably removed from the first operation stick 531A.

Adjusting the direction of the procedure instrument 504A around the axial line necessitates the main body section 911 of the operation section 506A to rotate around the axial line. Thus, rotational torque is input into the multi-layered coil 951 that is engaged to the intermediate coupling 941 in the rotational direction as illustrated in FIGS. 21 and 22. In the multi-layered coil 951, two coils adjacent to each other in a radial direction interfere with each other while they are tightened or loosened based on their combination of the winding direction and the rotational direction of the operation section 506A and thus, rotational torque is transferred. Since the treatment section 505A is fixed to the tip of the multi-layered coil 951, the transferred rotational torque rotates the treatment section 505A around the axial line. The rotation in the vicinity of the operator's hand is stopped after confirming that a desirable direction is obtained by means of an endoscopic image.

The slider 912 is forwarded after adjusting the direction and position of the treatment section 505A. The operation wire 932 moves an opening-and-closing mechanism of the treatment section 505A to open a pair of forceps members. The single-layered coil 942 receives an extension force generated by pushing the operation wire 932. The extension force is not applied to the multi-layered coil 951 because the multi-layered coil 951 is not engaged with the operation section 506A in the extension and retraction directions. This allows the treatment section 505A to be adjusted even if the forceps members are opened. Consequently, retracting the slider 912 causes the forceps members to close and grasp tissue. The compression force generated temporarily is received by the single-layered coil 942.

The procedure instruments 504A and 504B are retracted from the medical treatment endoscope 501 after completing necessary treatments. The procedure instruments 504A and 505B are also retracted from the medical treatment endoscope 501 in order to exchange procedure instruments necessary for a treatment. As illustrated in FIG. 28, the operation section 506A is rotated around the axial line after the cam 910 abuts the piston 715. The piston 715 is pushed up along the tilted side surface 921A of the blade section 921 of the cam 910. As illustrated in FIG. 29, providing the tilted side surface 921A enables pushing up of the piston 715 with a small force. Meanwhile, as illustrated in FIGS. 19 and 20, the procedure instrument 504A will never be rotated excessively if the gap surface 921B is provided. Furthermore, providing the slope 921C facilitates offsetting the piston 715 from the cam 910 in an axial line direction (thrust direction), thereby removal is easy. Meanwhile, it is preferable that the entire cam 910 be made of a metal in view of breakage protection. In addition, the cam 910 may be made of POM (polyoxymethylene) that has desirable slidability in view of facilitating operation in extension and retraction operations in the first operation stick 531A.

However, the treatment sections 505A and 505B cannot be removed if the second bending part 308 of the arm sections 302A and 303A is opened, and the engagement of the piston 715 and the cam 910 can be released. The piston 715 pushed up by the cam 910 in the operation section 520 is configured to automatically restore the second bending part 308 to a straightened state. That is, pushing up the piston 715 and releasing the engagement with the second groove 719 retract the second bending slider 711 with tension applied by the second bending wires 316A and 316B and a resilience of the coil spring 745. This results in causing the second bending part 308 to restore into the straightened state. In addition, a resilient part like a spring 792 as illustrated in FIG. 13 may be added to prevent energetic restoration of the second bending slider 711. Consequently, the medical treatment endoscope 501 is removed from the body after removing the procedure instrument 504A.

Next, a modified example of the present embodiment will be described as follows.

Figure 30:
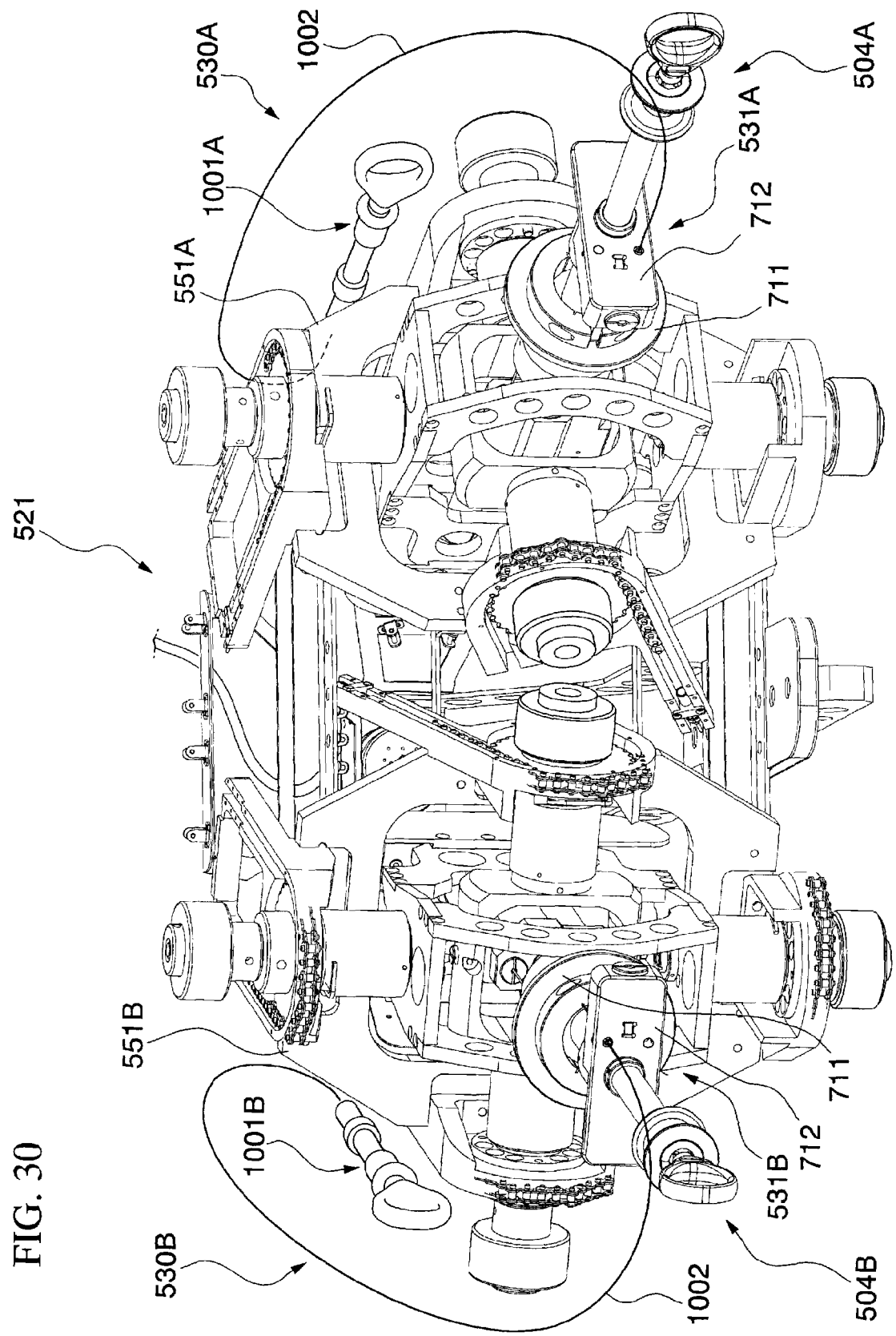
FIG. 30 illustrates a base having an operation section joined to a second bending slider disposed on a side of a base.
Figure 31:
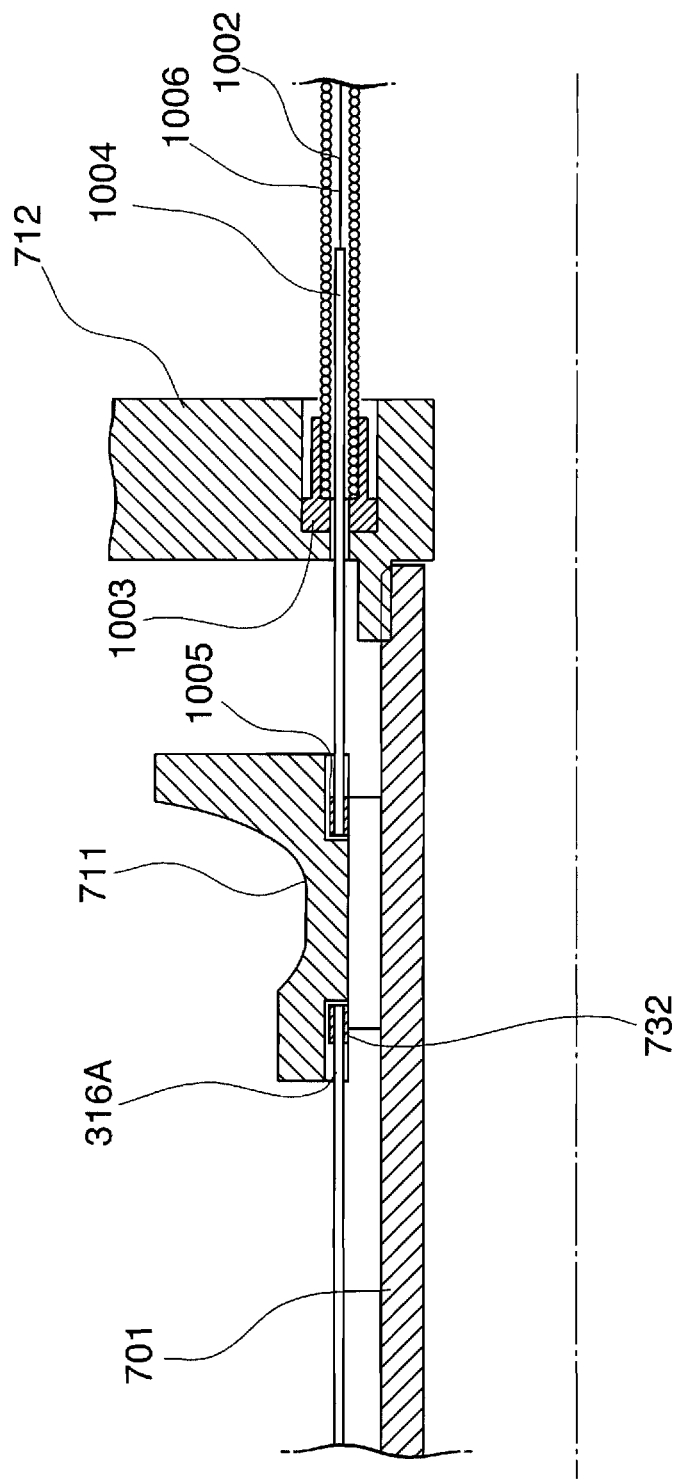
FIG. 31 is a cross-sectional view illustrating a mechanism for joining the second bending slider to the operation section in the configuration shown in FIG. 30.

As illustrated in FIG. 30, operation sections 1001A and 1001B each for operating the second bending slider 711 may be fixed to the bracket 551A and a bracket 551B in parallel with each axial line of the operation sticks 531A and 531B. The operation sections 1001A and 1001B each have an extendable and retractable slider. Moving the slider causes the wire in a coil sheath 1002 to be extended or retracted. As illustrated in FIG. 31, the coil sheath 1002 is fixed to the coil receiver 1003 attached to the ratchet base 712. A pipe 1004 is passed through the coil receiver 1003. The pipe 1003 passing through the coil sheath 1002 is rotatively engaged with the second bending slider 711 via the wire receiver 1005 together with the second bending wires 316A, 316B. A wire 1006 joined to the sliders of the operation sections 1001A and 1001B is passed through the pipe 1004. Retracting the sliders of the operation sections 1001A and 1001B moves the wire 1006, thereby drawing the second bending slider 711 and opening the second bending part 308. In this configuration, the operation section 520 can be downsized and thus, operation of the second bending part 308 can be facilitated. Also, this configuration prevents the movement of the operation sticks 531A and 531B during the operation of the second bending part 308. Thus, grasped tissue will never be moved unexpectedly.

Figure 32:
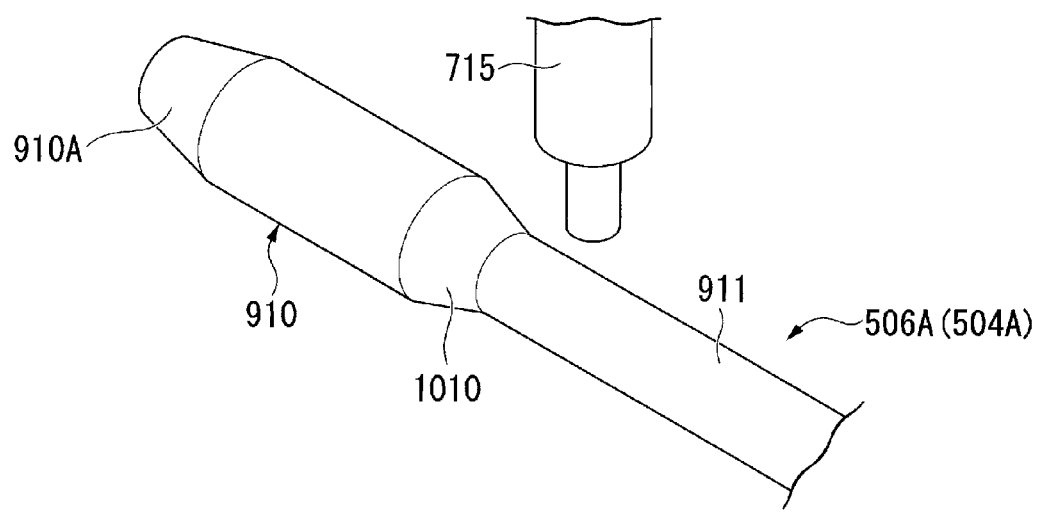
FIG. 32 shows a modified example of the cam.

As illustrated in FIG. 32, the base end of the cam 910 may be an inclination surface 1010. Drawing the procedure instrument 504A from the first operation stick 531A causes the piston 715 to move up the inclination surface 1010, thereby removing the procedure instrument 504A. The procedure instrument 504A cannot be removed with a force based on the retraction of the procedure instrument 504A toward the operator during a treatment. Further additional force will provide retraction. In this configuration, the procedure instrument 504A can be removed without rotating the operation section 506A.

Figure 33:
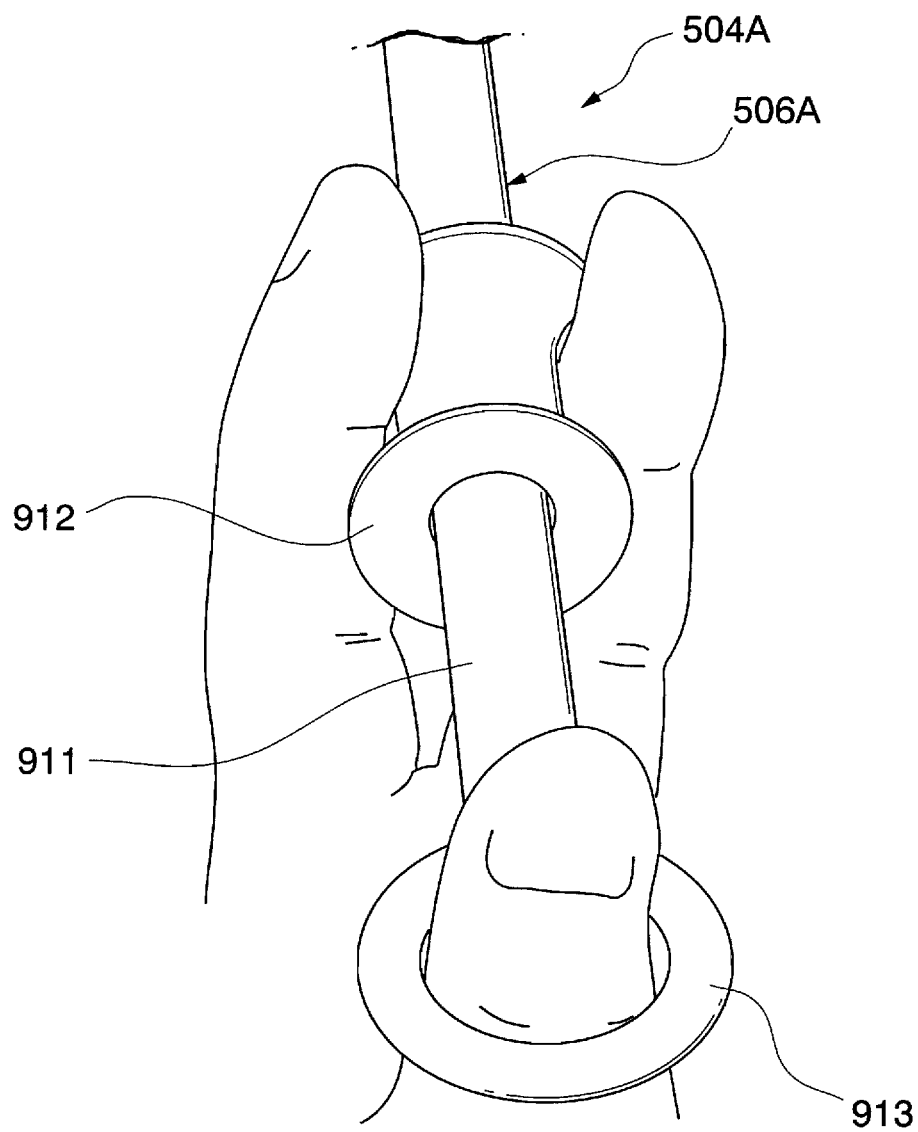
FIG. 33 illustrates a feed operation for the procedure instrument.
Figure 34:
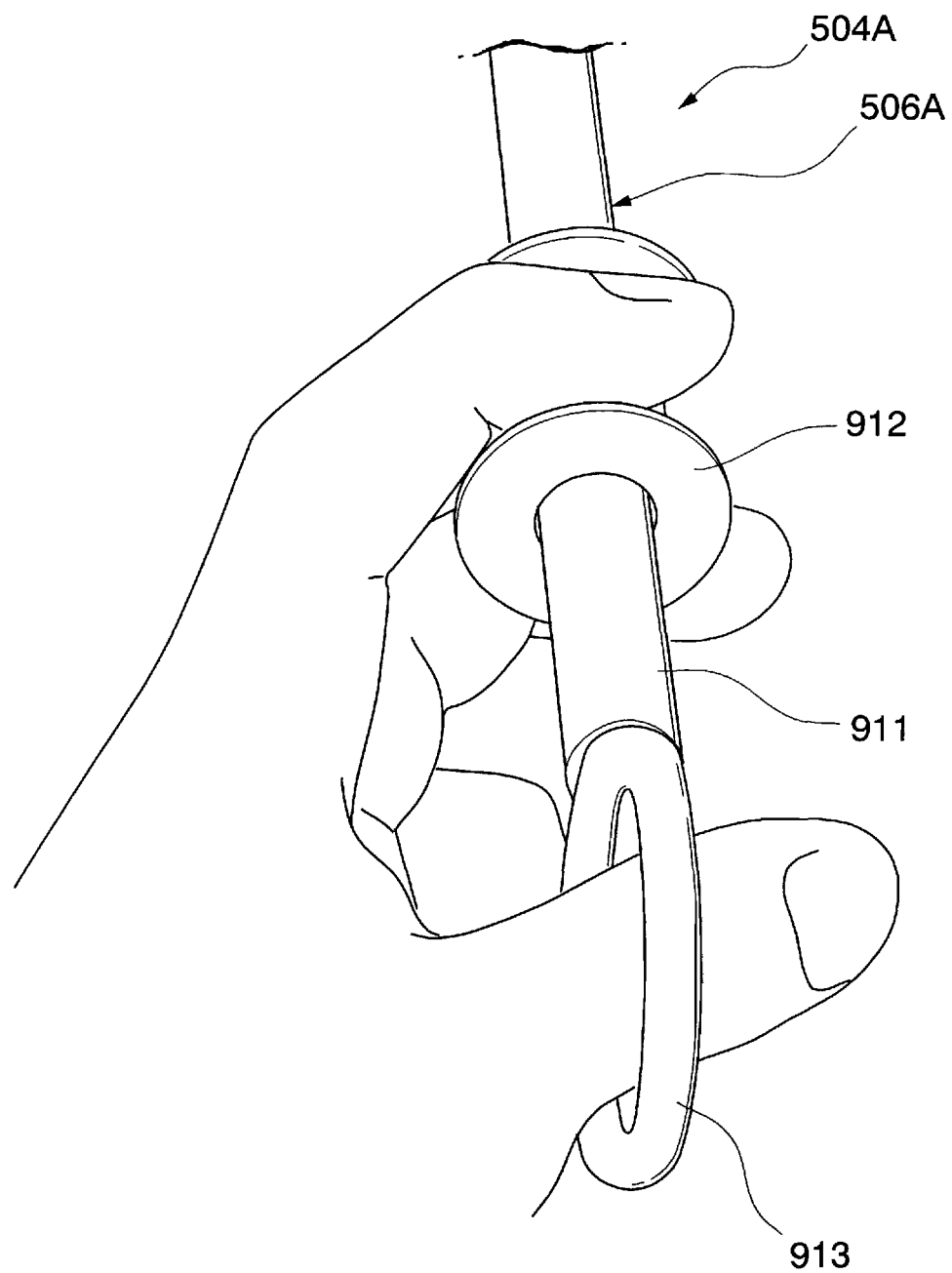
FIG. 34 illustrates a feed operation for the procedure instrument.

In addition, operations for significant rotations of the procedure instruments 504A and 504B will be explained with reference to FIGS. 33 and 34. This includes cases where we intend to adjust the treatment section 505A in the optimum direction to grasp tissue. As illustrated in FIG. 33, the slider 912 is held with an index finger and a middle finger. The hand-held state of the slider 912 is rotated in a clockwise direction by 90°. The index finger and the middle finger are withdrawn from the slider 912 after rotating the slider 912 and the main body section 911 to the positions illustrated in FIG. 34. The hand not holding the slider 912 is rotated in a counterclockwise direction by 90° to the position illustrated in FIG. 33. This state of the insertion section 507A of the procedure instrument 504A has friction relative to channels in a first operation stick 531A and the second arm member 302A. To be more specific, the channels are a channel 801, a channel in the connection sheath 515, and a channel in the endoscope insertion section 503. Therefore, the insertion section 507A will not rotate in the counterclockwise direction with a mere touch with the slider 912 and thus, its disposition is maintained. Repeating the above steps enables 90° feed operation of the procedure instrument 504A.

Figure 35:
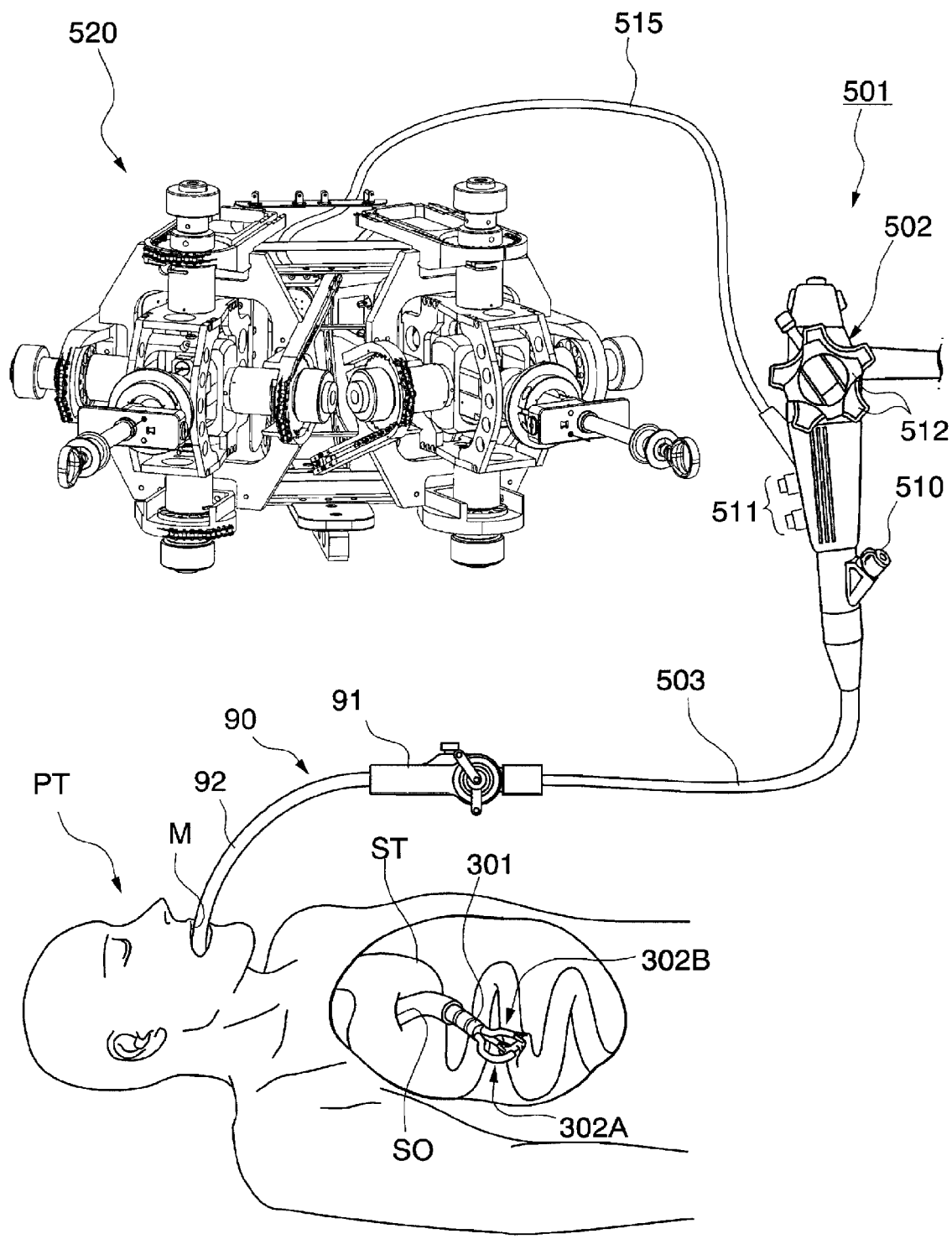
FIG. 35 illustrates a combined use of the medical treatment endoscope and an overtube.

As illustrated in FIG. 35, the medical treatment endoscope 501 may be passed through the overtube 90. The first operator handling the endoscope insertion section 502 conducts ordinary endoscopic operation with his/her left hand while operating the endoscope insertion section 503 and overtube 90 with his/her right hand. The use of bending of the overtube 90 improves the approachability to the object position in the abdominal cavity.

Second Embodiment

In a medical treatment endoscope of the present embodiment, a channel for inserting a procedure instrument therethrough is detachable in the operation section.

Figure 36:
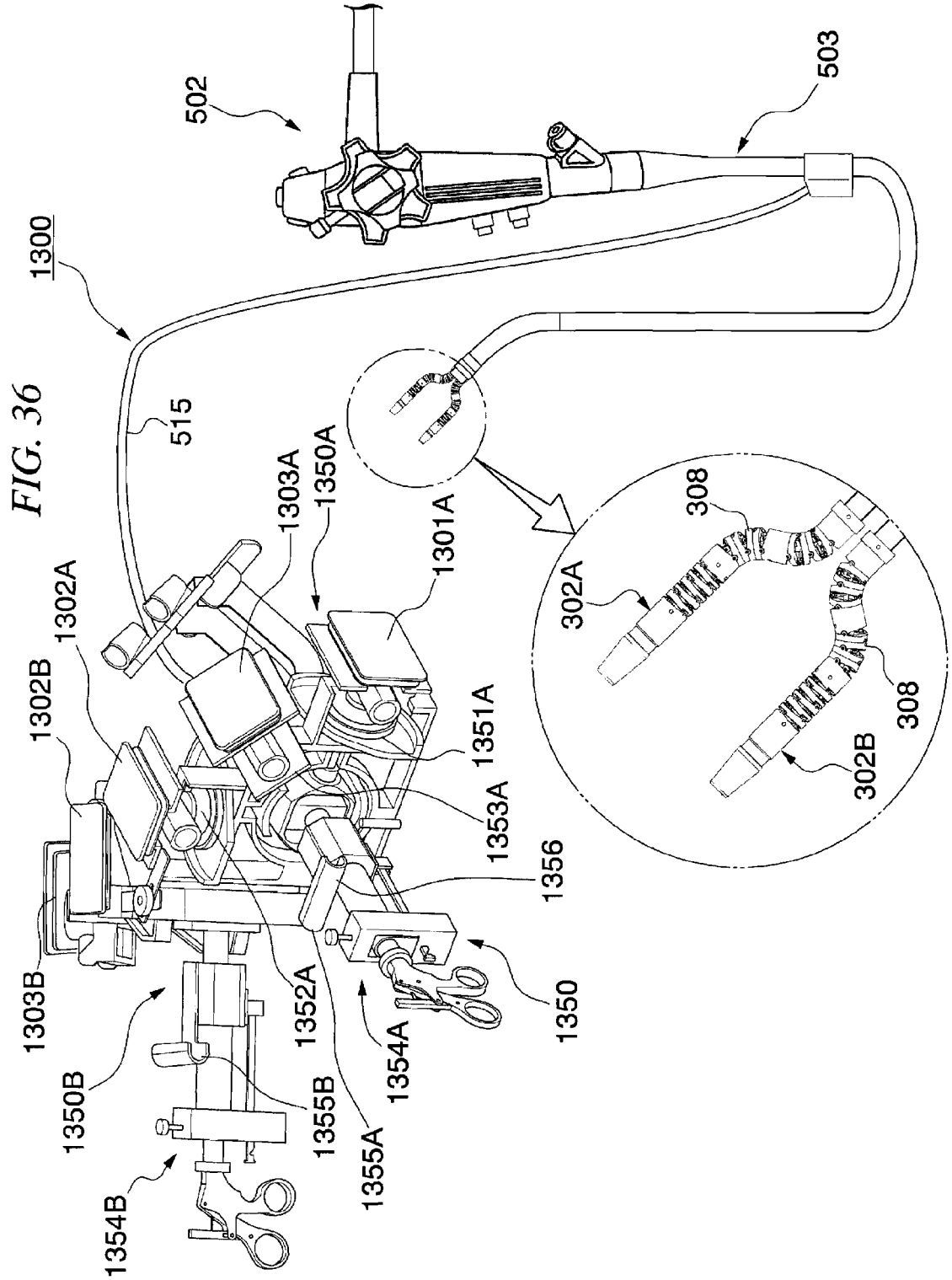
FIG. 36 shows the structure of the medical treatment endoscope according to the second embodiment of the present invention.

As illustrated in FIG. 36, a medical treatment endoscope 1300 according to the present embodiment is provided with the endoscope insertion section 502, the endoscope insertion section 503, and the operation section 1102 that are the same as those of the first embodiment. Wires for maneuvering the two arm sections 302A and 302B extending from the endoscope insertion section 503 passing through the connection sheath 515 are connected to a wire unit detachable from the operation section 1350. Three wire units are provided to each arm section and include two first wire units having a vertically moving first wire unit 1301 and a horizontally moving second wire unit 1302; and a second-bending-wire unit 1303. Therefore, the present embodiment is provided with six wire units in total, i.e. wire units 1301A, 1302A, and 1303A that are connected to the first arm section 302A and wire units 1301B (not shown in the drawing), 1302B, and 1303B that are connected to the second arm section 302B.

The operation section 1350 having substantially the same structure as the operation section 520 of the first embodiment includes a first operation unit 1350A for maneuvering the first arm section 302A; and a second operation unit 1350B for maneuvering the second arm section 302B.

The first wire units 1301A and 1301B are attached to first rotation mechanisms 1351A and 1351B of the operation units 1350A and 1350B, not shown in the drawing, respectively. The second wire units 1302A and 1302B are respectively attached to second rotation mechanisms 1352A and 1352B of each operation unit, not shown in the drawing. In the operation units 1350A and 1350B, the second bending wire units 1303A and 1303B are attached detachably to second bending-operation-mechanisms 1353A and 1353B, not shown in the drawing, provided between the first rotation mechanism and the second rotation mechanism.

The second-bending-operation mechanisms 1353A and [B]1353B are connected to sliders 1355A and 1355B provided to operation sticks 1354A and 1354B having procedure instruments inserted through the arm sections 302A and 302B via transmission members, e.g. a wire. (details thereof will be explained later). Drawing the sliders 1355A and 1355B proximally causes the second bending 308 of the arm section to bend. Finger hook sections 1356 formed by bending a plate member are provided to the sliders 1355A and 1355B so that operation while grasping the operation sticks 1354A and 1354B by hooking fingers thereto can be conducted.

Accordingly, maneuvering the operation sticks 1354A and 1354B cause the wires connected to the wire units 1301 and 1302 via rotation mechanisms 1351 and 1352 to be operated, thereby permitting operation of the arm sections 302A and 302B.

An operation stick (hereinafter called simply a "stick") and the structure of a channel will be explained next. It should be noted that the sticks 1354A and 1354B have the same structure in the following explanation provided in associate with the stick 1354A as an example.

Figure 37:
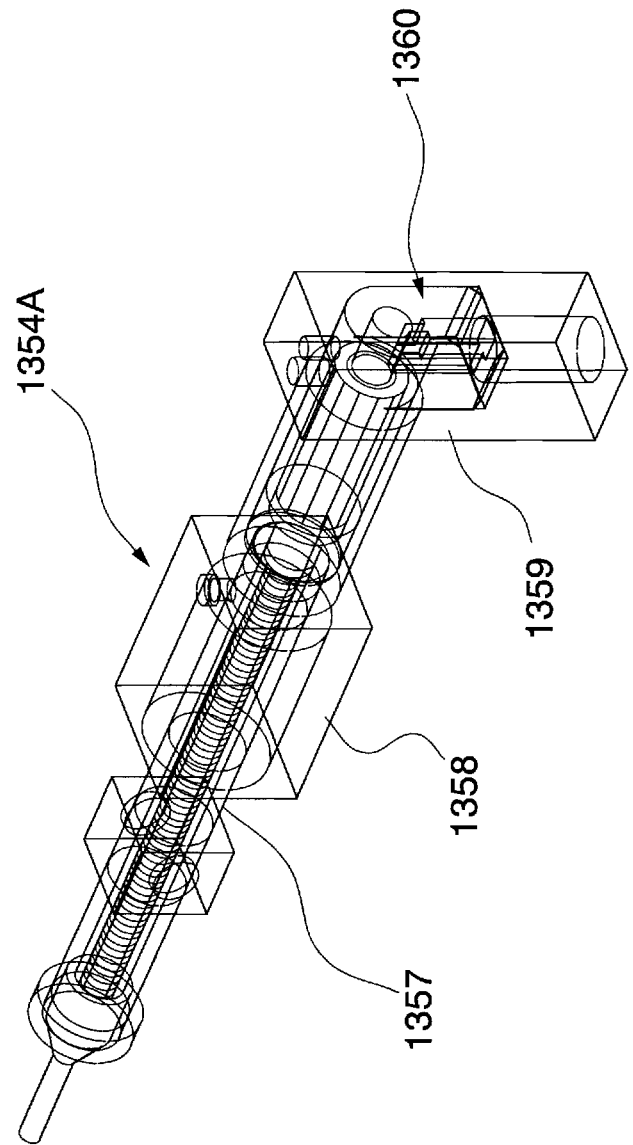
FIG. 37 shows an operation stick of the medical treatment endoscope.

FIG. 37 is a perspective view showing the stick 1354A. It should be noted that FIG. 37 is a perspective view facilitating visualization of the inside of the stick 1354A. The stick 1354A is provided with a tubular main body 1357; a slider section 1358 having a slider 1355, provided therein, which will be explained later; and a fixture section 1359 for fixing a channel unit 1360 to the main body 1357. The channel unit 1360 having a procedure instrument therethrough is inserted in the main body 1357 from the vicinity of the fixture section 1359 and is fixed to the fixture section 1359 detachably.

Figure 38:
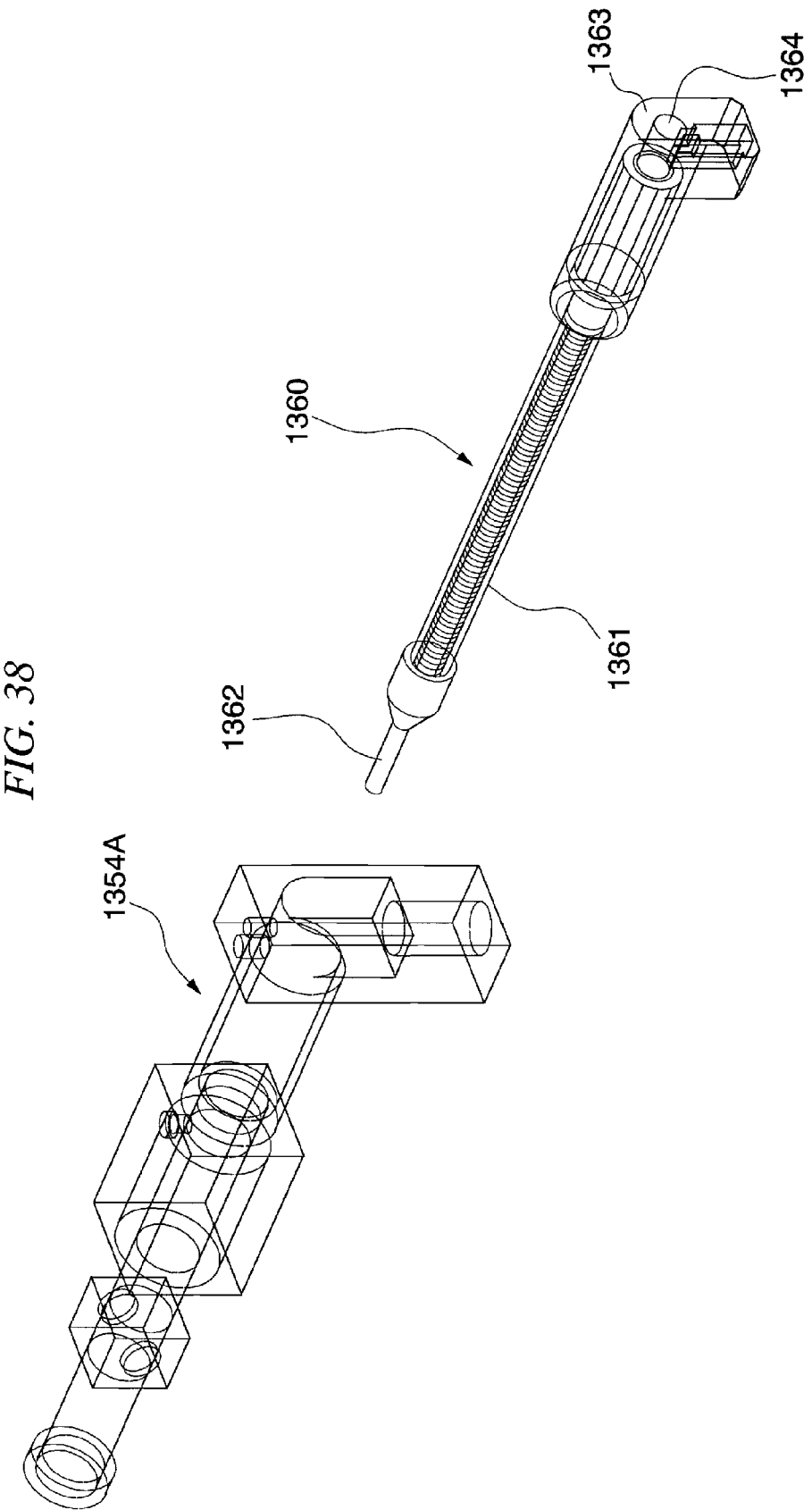
FIG. 38 is a perspective view showing a channel unit removed from an operation stick.

FIG. 38 is a perspective view showing the channel unit 1360 removed from the stick 1354A. The channel unit 1360 is provided with a tubular main body 1361; a connecting section 1362 attached to one of the ends of the main body 1361; and a mating fixed section 1363 fixed to the fixture section 1359 of the stick 1354A.

The channel unit 1360 is made from a material resistible to cleaning and sterilization. Specific adaptable examples are: SUS303 and SUS 304 as a metal material; and, for example, polyester, polyetheretherketone, and polyethersulphone as a resin material.

The connecting section 1362 is connected with the instrument channel which communicates with an inner cavity of the first arm section 302A and extends to the connection sheath 515 through the endoscope insertion section 503. It is preferable that the tip of the connecting section 1362 is made from a flexible material which can absorb a shift in distance to some extent between a distal end of the stick and the fixture position because operating the operation units 1350A and 1350B will vary the shift.

It should be noted that the structure of the tip of the connecting section 1362 and a method for connecting it to the instrument channel will be explained later.

The mating fixed section 1363, which has the next smaller size than that of the fixture section 1359 of the stick 1354A, is enclosed in the fixture section 1359 and fixed detachably. In addition, an opening 1364 for inserting a procedure instrument therethrough is provided to the mating fixed section 1363. The procedure instrument inserted into the opening 1364 and passing through the main body 1361 and the connecting section 1362 upon entering the instrument channel can reach to the first arm section 302A.

Figure 39:
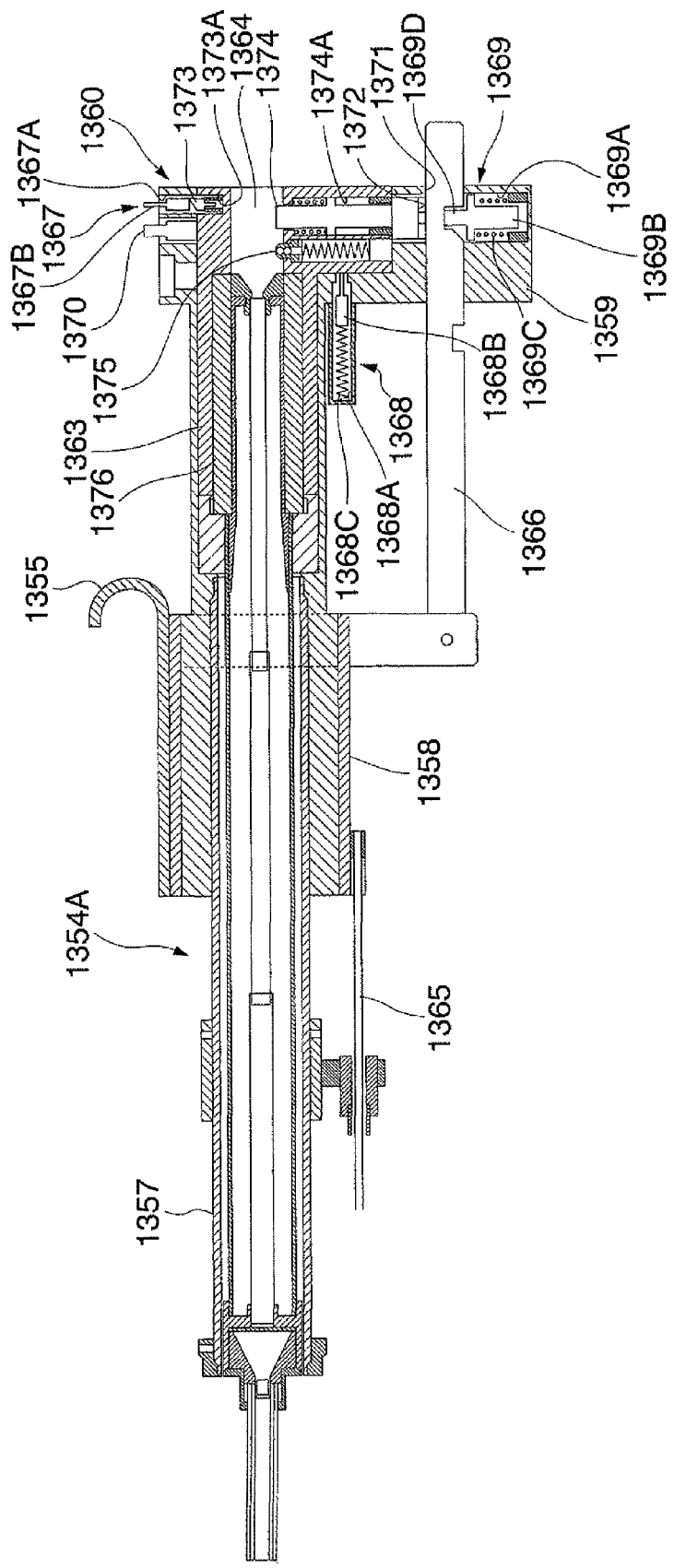
FIG. 39 is a cross-sectional view of the operation stick.

FIG. 39 is a cross-sectional view showing the stick 1354A having the channel unit 1360 inserted therein. The slider section 1358 capable of sliding along the axial line of the main body 1357 is attached to an outer periphery of the main body 1357. An operation member 1365 attached to the second bending operation mechanism 1353 is attached to the slider section 1358. For example, the operation member 1365 is formed by a wire inserted through a metal coil, which is not shown in the drawings. Therefore, drawing the slider 1355 enables operation of the second bending of the first arm section 302A via the second bending operation mechanism 1353. In addition, an erroneous-operation-preventive connecting member 1366 attached to the slider section 1358 is inserted through the fixture section 1359. The connecting member 1366 provides substantially the same function and movement as those of the connection plate 713 explained in the first embodiment, and details thereof will be explained later.

The fixture section 1359 has a release switch 1367 which releases the fixture between the stick 1354A and the channel unit 1360; an urging section 1368 which protrudes the channel unit 1360 when the fixture is released; an erroneous-movement-preventive section 1369 which engages with the connecting member 1366 to regulate the movement of the slider section 1358; and a removal button 1370 used for removing the procedure instrument inserted into the channel unit 1360.

A switching member 1367B provided to the release switch 1367 and attached in a through-hole 1367A provided on the upper surface of the fixture section 1359 is capable of sliding in the through-hole 1367A.

A cylinder 1368B inserted into a hole 1368A provided in parallel with the axial line of the main body 1361 forms the urging section 1368. Such a structure called a plunger is commonly known. The cylinder 1368B urged by a spring 1368C is configured to protrude into the inner cavity of the fixture section 1359.

A substantial cylindrical engagement piston 1369B inserted into a hole 1369A provided to the bottom surface of the fixture section 1359 forms the erroneous-movement-preventive section 1369. A spring 1369C urges the engagement piston 1369B upward. The hole 1369A crosses a through-hole 1371 having the connecting member 1366 inserted therethrough substantially orthogonally. In addition, the engagement piston 1369B is provided with a through-hole 1372 which communicates with the through-hole 1371.

This causes the connecting member 1366 to pass through the through-holes 1371 and 1372 and protrude in the vicinity of the fixture section 1359 proximally. An upwardly-protruding engagement protrusion 1369C provided in the through-hole 1372 of the engagement piston 1369B is capable of engaging with an engagement groove, which will be explained later, provided to the connecting member 1366.

On the other hand, the mating fixture section 1363 of the channel unit 1360 is provided with engagement jaws 1373 which engage with the stick 1354A; a first piston 1374 (regulating section) synchronously moving with the erroneous-movement-preventive section 1369 to control the movement of the connecting member 1366; and a second piston (falloff-preventive section) 1375 for preventing the inserted procedure instrument from dropping off of the channel unit 1360 erroneously.

The engagement jaws 1373 urged by a spring to protrude relative to the upper surface of the mating fixed section 1363 is designed to have dimensions which allow the engagement jaws 1373 to be enclosed fully in the hole 1373A. In addition, the vicinity of the tip is formed to have an oblique surface which facilitates insertion of the channel unit 1360 into the stick 1354A.

Therefore, inserting the channel unit 1360 into the stick 1354A causes the oblique surfaces of the engagement jaws 1373 in the vicinity of the tip to make contact with the fixture section 1359, thereby causing the engagement jaws 1373 to be pushed by the fixture section 1359 and enclosed in the hole 1373A. The engagement jaws 1373 upon reaching the bottom of the through-hole 1367A of the fixture section 1359 moves upward and enters the through-hole 1367A to push the switching member 1367B. Accordingly, the engagement between the engagement jaws 1373 and the through-hole 1367A causes the channel unit 1360 to be detachably fixed to the stick 1354A.

A spring prevents the first piston 1374 inserted and enclosed in the through-hole 1374A from protruding into the inner cavity of the mating fixed section 1363 by urging the first piston 1374. The urging force acting onto the first piston 1374 is set to be significantly weaker than that of the spring 1369C urging the engagement piston 1369B. The through-hole 1374A is provided at a position which provides communication between the through-hole 1374A and the hole 1369A having the engagement piston 1369B inserted therein when the channel unit 1360 is fixed to the stick 1354A unitarily. Therefore, fixing the channel unit 1360 to the stick 1354A unitarily causes the first piston 1374 to make contact with the engagement piston 1369B. In addition, the urging force of the spring 1369C causes the first piston 1374 to protrude into the inner cavity of the mating fixed section 1363. In addition, the lower section of the first piston 1374 pushed downward protrudes below the through-hole 1374A allows the engagement piston 1369B to be pushed down.

In addition, a commonly-known linear bush 1376 is attached to a part of the mating fixed section 1363. Bearings, not shown in the drawing, rotatable in the axial line direction in the inner cavity of the linear bush 1376 can provide accurate extension and retraction movement of an inserted procedure instrument along the axial line with less significant force.

Figure 40:
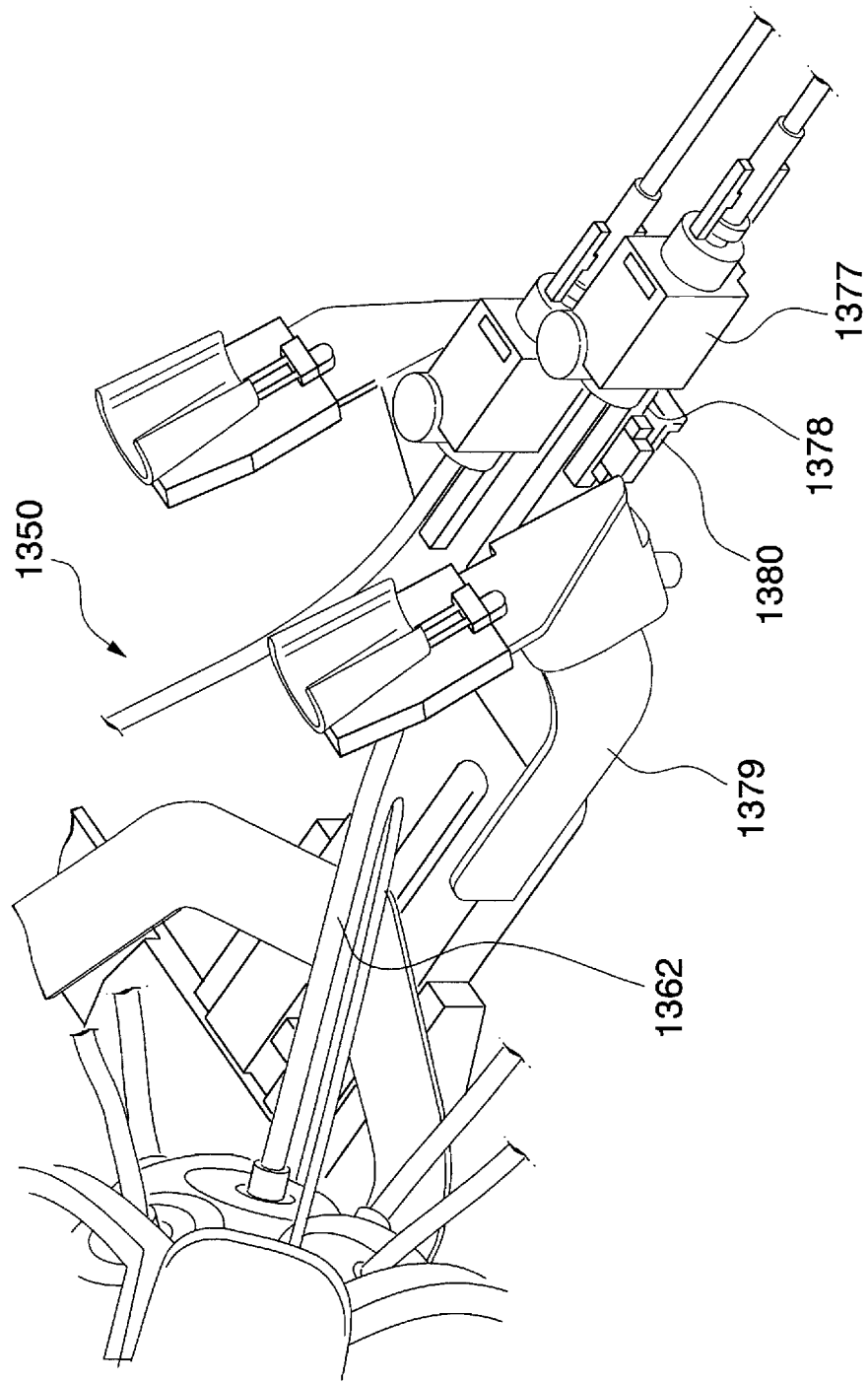
FIG. 40 shows the vicinity of a channel-fixing section of the operation section of the medical treatment endoscope.

FIG. 40 shows the operation section 1350 in the vicinity of the tip in a magnified view. A channel-fixing section 1377 fixing the connecting section 1362 provided to the tip of the channel unit 1360 is provided in the vicinity of the operation section 1350.

The rail 1378 is attached below the channel-fixing section 1377. The rail 1378 engaging with a base 1380 fixed to an enclosure 1379 is capable of sliding in the longitudinal direction of the rail 1378 relative to the base 1380. This allows the channel-fixing section 1377 to make extending and retracting movements of a predetermined length. Accordingly, smooth operation can be obtained since the channel-fixing section 1377 makes extending and retracting movements corresponding to vertical and/or horizontal movements of the two operation sticks 1354A and 1354B of the operation section 1350.

Movement of the medical treatment endoscope having the aforementioned structure in use will be explained as follows. The channel unit explained here in the present embodiment is a sterilized non-recyclable unit 1360A.

Figure 41:
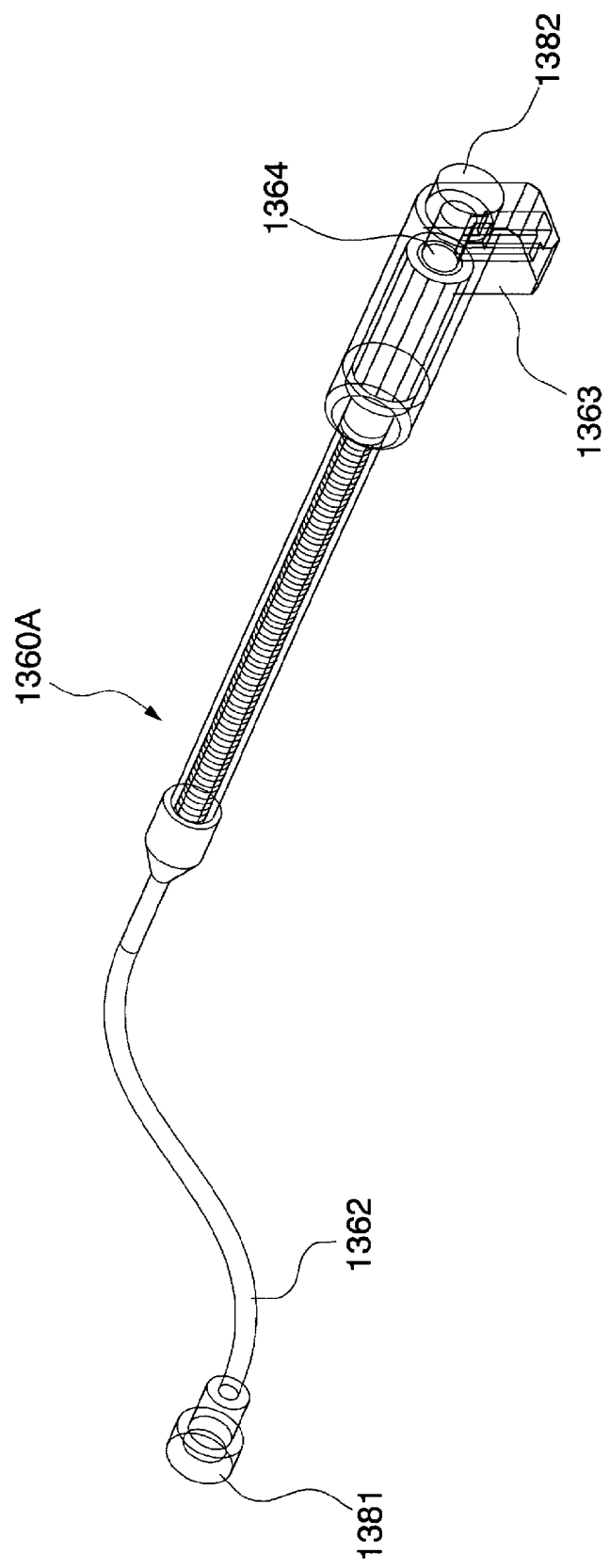
FIG. 41 is a perspective view showing the sterilized channel unit.

FIG. 41 is a perspective view showing the channel unit 1360A. Channels formed on the outer and inner peripheries of the channel unit 1360A are sterilized by various methods, e.g., autoclave method or a gas sterilization method, etc. A first cap 1381 and a second cap 1382 are attached to openings 1364 of the connecting section 1362 and the tubular main body 1361 respectively to maintain unsterilized condition of the channels. The first cap 1381 is set to have a diameter that allows the first cap 1381 to pass through the inner cavity of the stick 1354A. Screw engagement is provided to the caps 1381 and 1382 attached to the channel unit 1360. Forming the screw sections engaging with each other by a metal material improves sterilized condition of the screw sections provided by the autoclave method, etc.

To start with, the channel units 1360A are inserted into the openings of the fixture sections 1359 of the sticks 1354A and 1354B. Subsequently, the engagement jaws 1373 are engaged with the through-hole 1367A of the release switch 1367; and the channel unit 1360A is fixed to the stick 1354A unitarily. The method for operating of the stick 1354A explained as follows is to the stick 1354B connected to the second arm section 302B.

Figure 42:
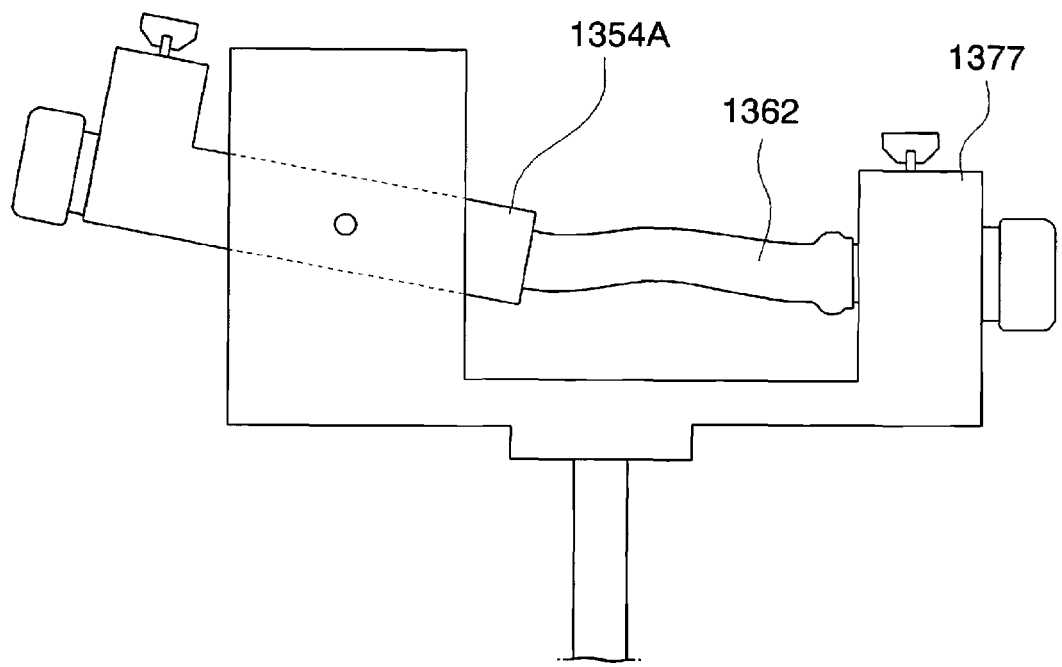
FIG. 42 shows the channel unit inserted into the operation section.

Subsequently, the tip of the connecting section 1362 protruding from the tip of the stick 1354A is inserted from an opening formed in the vicinity of the base end of the channel-fixing section 1377 as shown in FIG. 42.

Figure 43:
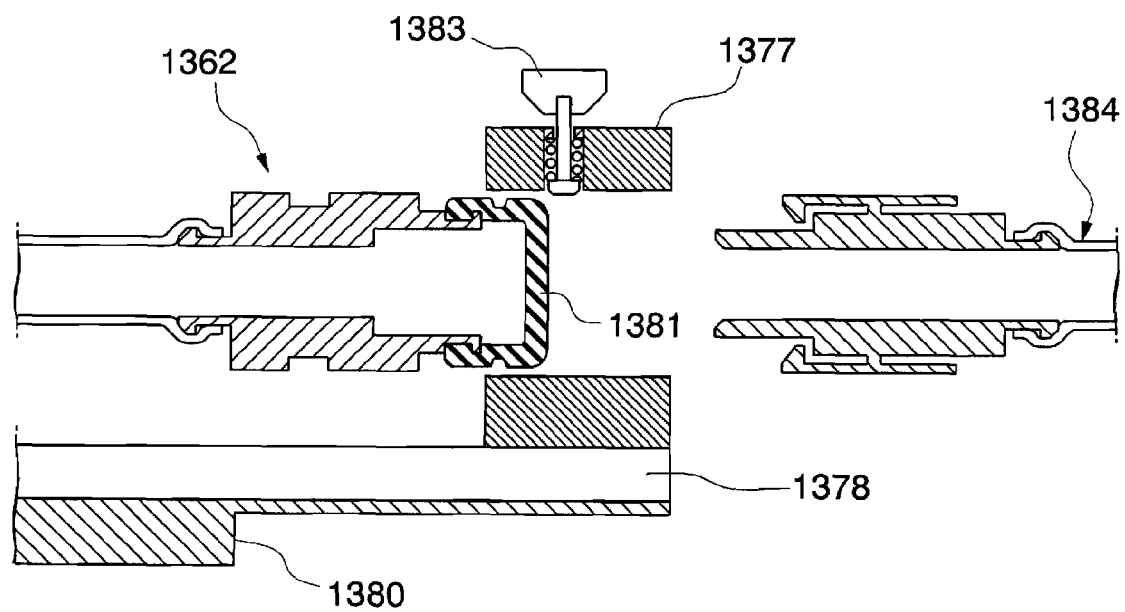
FIG. 43 is a cross-sectional view showing the connection section of the channel unit and the channel-fixing section.

FIG. 43 shows the channel-fixing section 1377 and the connecting section 1362 in a cross-sectional view. A fixed knob 1383 provided to the channel-fixing section 1377 is drawn and the connecting section 1362 is inserted. Subsequently, releasing the fixed knob 1383 upon protruding the first cap 1381 from the tip of the channel-fixing section 1377 causes the fixed knob 1383 urged by a spring to protrude inward relative to the channel-fixing section 1377 and engage with the connecting section 1362. Accordingly, the connecting section 1362 is fixed to the channel-fixing section 1377 detachably as shown in FIG. 42.

Figure 44:
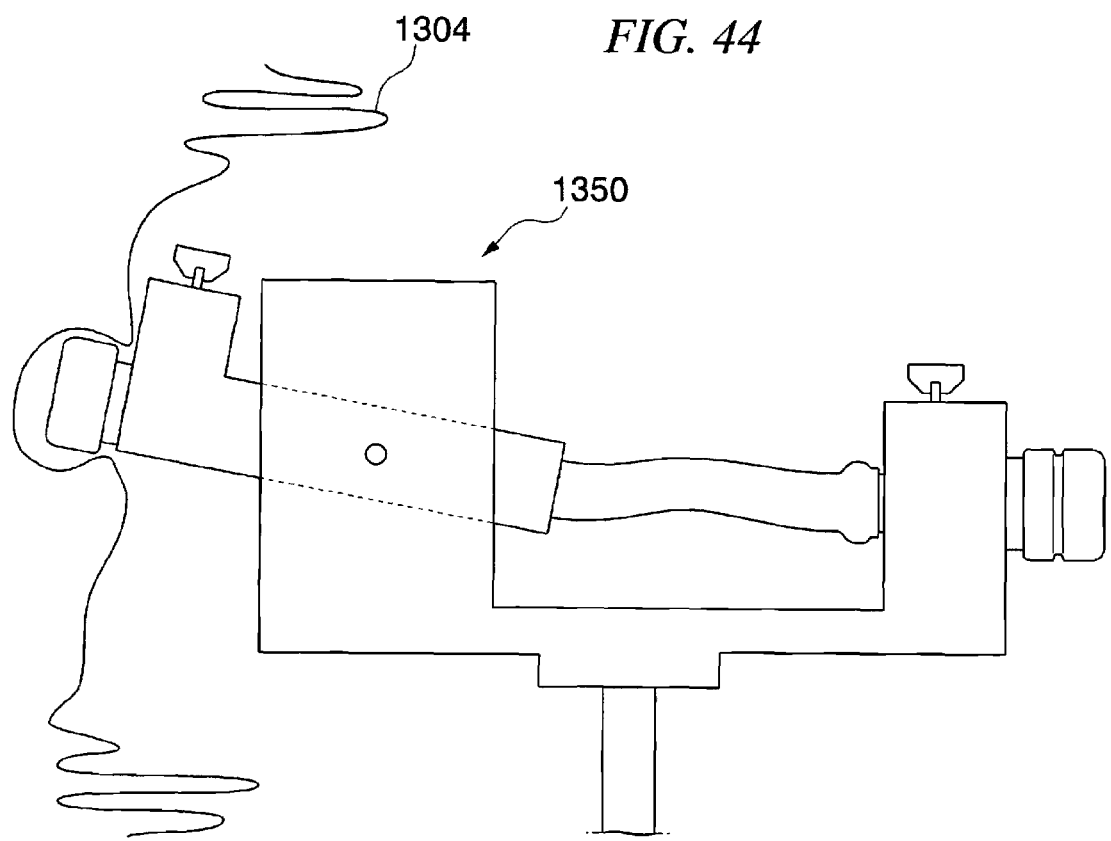
FIG. 44 shows operation of disposing a drape onto the operation section.

Subsequently, the connecting section 1362 is connected to an instrument channel 1384 extending from the endoscope insertion section 503 through the connection sheath 515. As shown in FIG. 44, the operation section 1350 should be covered with a drape 1304 to prevent a user from touching the unsterilized sticks 1354A and 1354B or the whole part of the operation section.

Figure 45:
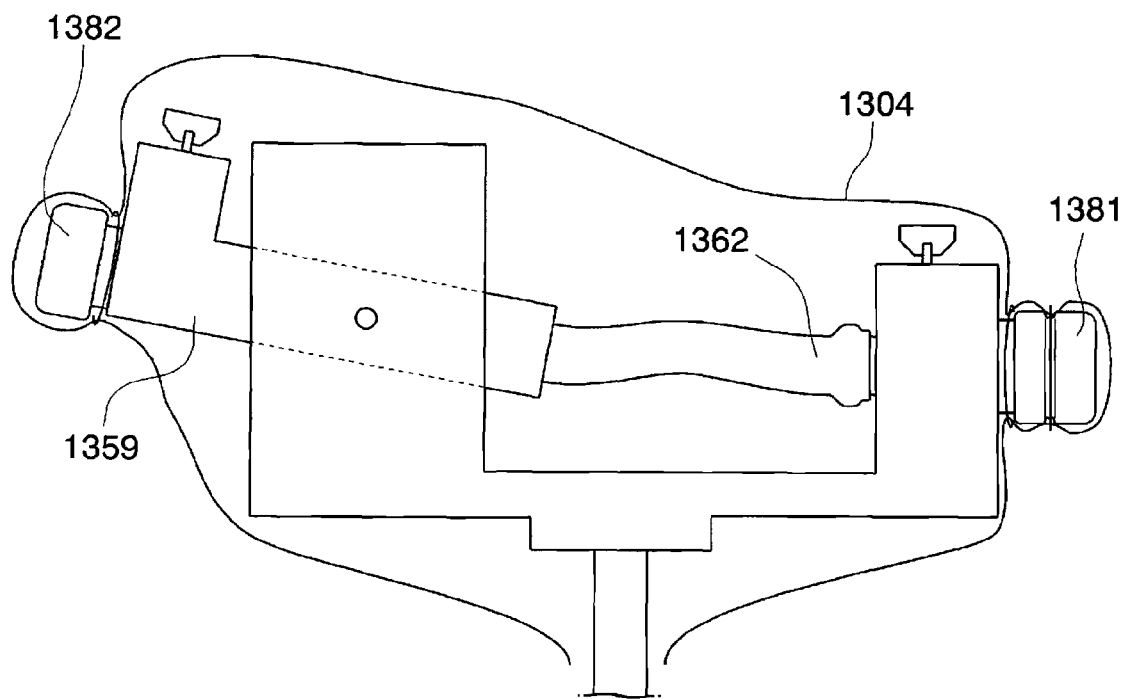
FIG. 45 shows the operation section covered by the drape.

Subsequently, the boundary part between the first cap 1381 and the connecting section 1362 is fixed by a tape or a rubber member as shown in FIG. 45. In addition, the outer periphery section of the first cap 1381 may be fixed by a tape or a rubber member etc. In addition, the boundary part between the second cap 1382 and the fixture section 1359 is fixed similarly. It is preferable that perforation facilitating separation thereof should be provided previously to the part corresponding to the drape 1304 fixed thereon.

Figure 46:
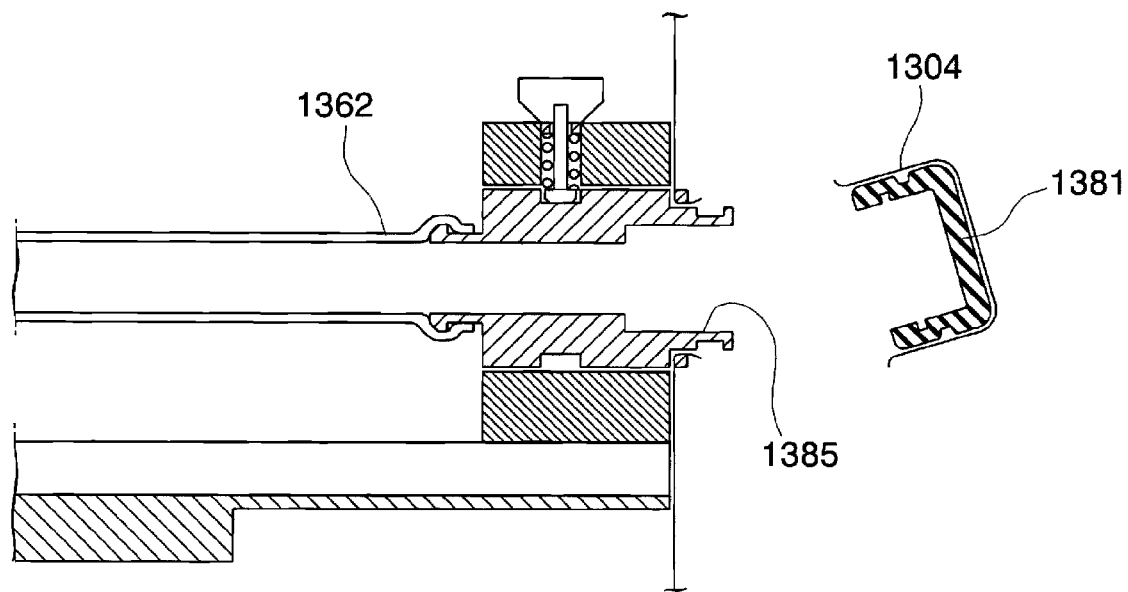
FIG. 46 shows a first cap removed from the connection section.

As shown in FIG. 46, the user upon separating the drape 1304 along the perforation and removing a part of the drape 1304 and the first cap 1381 together from the connecting section 1362 obtains an opening 1385, which maintains sterilized condition, formed on the tip of the connecting section 1362.

Figure 47:
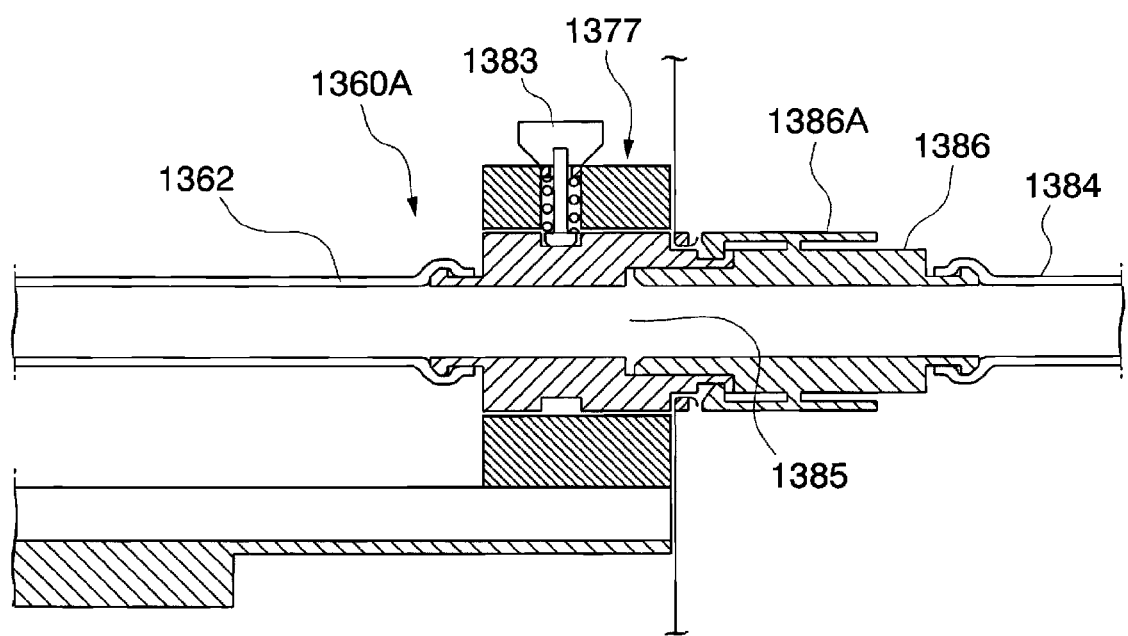
FIG. 47 shows the channel unit connected to the treatment instrument channel.

Subsequently, inserting a connecting member 1386 provided in the vicinity of the base end of the sterilized instrument channel 1384 into the opening 1385 and engaging the connecting section 1362 with the connecting member 1386 cause the channel unit 1360 to connect with the instrument channel 1384 in a sterilized manner as shown in FIG. 47. A channel for inserting a procedure instrument in a sterilized condition thereinto is formed in this manner. The channel communicates from the first arm section 302A to the mating fixed section 1363 of the channel unit 1360A. It should be noted that warp of the instrument channel 1384 during operation of the procedure instrument is prevented since the connecting member 1386 attached to the instrument channel 1384 is capable of freely rotating around the axial line.

Subsequently, a part of the drape 1304 together with the second cap 1382 are removed and the opening 1364 of the mating fixed section 1363 is released by the same operation as that conducted to the aforementioned first cap 1381 to insert the procedure instrument. Subsequently, the procedure instrument for use inserted into the opening 1364 is protruded from the tip of the first arm section 302A.

FIGS. 48 to 53 show the mating fixed section 1363 of the channel unit 1360A and the erroneous-movement-preventive section 1369 of the stick 1354A during the insertion of the procedure instrument. A procedure instrument 1305 specifically used for the medical treatment endoscope 1300 has an engagement groove 1305A formed in the circumferential direction thereof. The engagement groove 1305A formed to be shallower toward the base end thereof has a taper surface 1305B. It is preferable that the engagement groove 1305A be provided so that the tip of the procedure instrument 1305 may engage with the second piston 1375 upon inserting the tip of the procedure instrument 1305 in the vicinity of the tip relative to the second bending of the first arm section.

A first engagement section 1387 and a second engagement section 1388 provided to the connecting member 1366 are capable of engaging with the engagement protrusion 1369D of the engagement piston 1369B. The first engagement section 1387 in the vicinity of the base end has a first notch 1387A having a taper surface; and a second notch 1387B formed deeper than the first notch 1387A and proximal relative to the first notch 1387A. A step 1387C having a predetermined, for example, several millimeters of depth, is provided between the first notch 1387A and the second notch 1387B.

Figure 48:
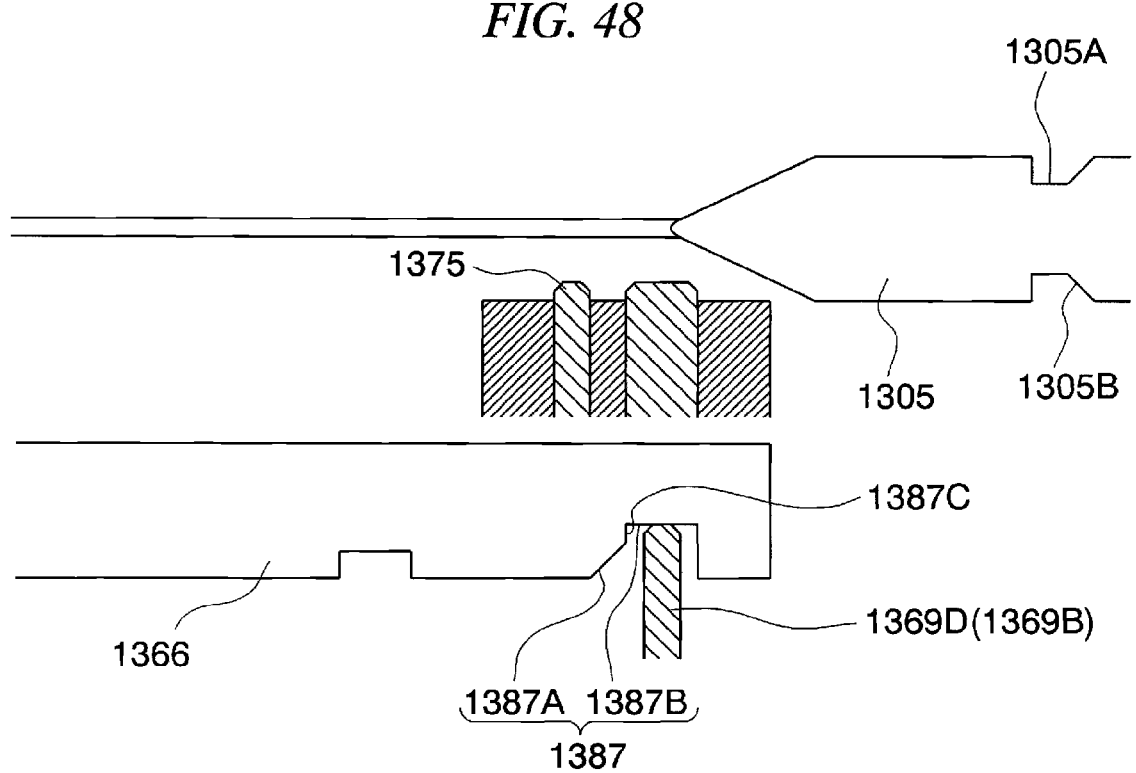
FIG. 48 shows the channel unit and an erroneous-movement-preventive section of the operation stick prior to insertion of the treatment instrument.
Figure 49:
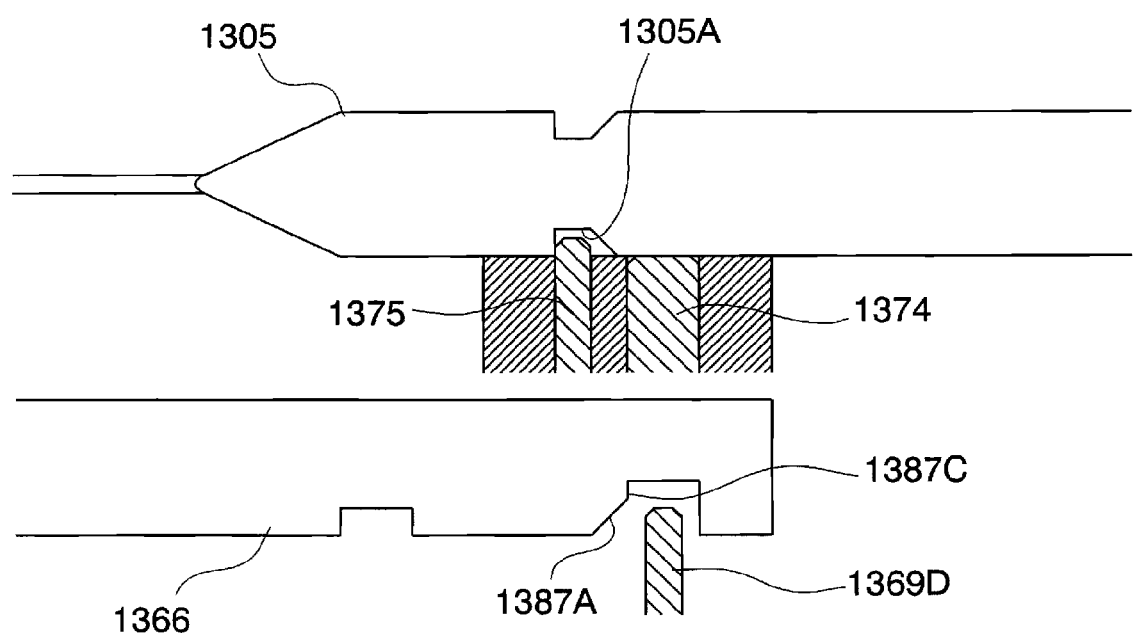
FIG. 49 shows the channel unit and the erroneous-movement-preventive section of the operation stick when the treatment instrument is inserted.

As shown in FIG. 48, the engagement protrusion 1369D of the engagement piston 1369B engages with the second notch 1387B of the first engagement section 1387 prior to the insertion of the procedure instrument 1305. The connecting member 1366 in an attempt to draw the slider section 1358 in this state proximally cannot move proximally since the engagement protrusion 1369D abuts to the step 1387C. This prevents bending of the second bending of the arm section based on erroneous maneuvering of the slider section 1358 prior to insertion of the procedure instrument 1305 into the channel unit 1360A.

It should be noted that the state of first piston 1374 making contact with the engagement piston 1369B is urged by the spring 1369C and protruded into the inner cavity of the mating fixed section 1363.

Figure 50:
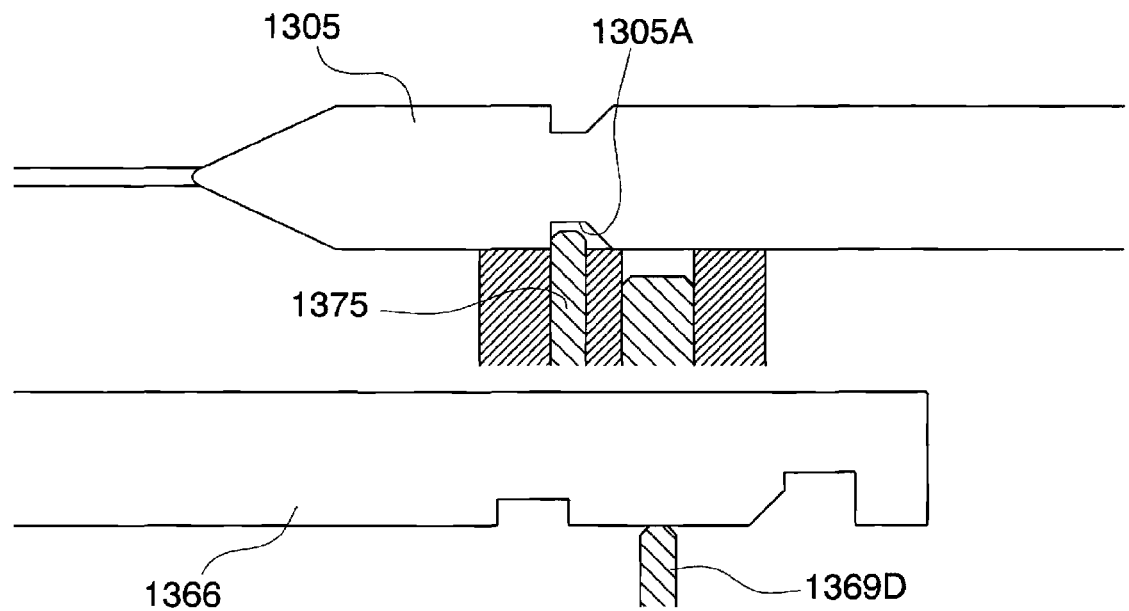
FIG. 50 shows the channel unit and the erroneous-movement-preventive section of the operation stick when a slider is drawn.

The outer periphery of the procedure instrument 1305 upon inserting the procedure instrument 1305 into the channel unit 1360A and protruding the second piston 1375 into the engagement groove 1305A pushes the first piston 1374 downward. The first piston 1374 presses down the engagement piston 1369B of the erroneous-movement-preventive section 1369. Then the upper end of the engagement protrusion 1369D moves lower than the step 1387C. Drawing the slider section 1358 in this state proximally causes the taper surface of the first notch 1387A to make contact with the engagement protrusion 1369D, thereby allowing the connecting member 1366 to move across the engagement protrusion 1369D proximally as shown in FIG. 50. That is, bending operation of the second bending 308 is possible. This state of engagement groove 1305A of the procedure instrument 1305 engaging with the second piston 1375 prevents erroneous retraction and drop-off of the slider section 1358 from the channel unit 1360A while operating the slider section 1358.

Figure 51:
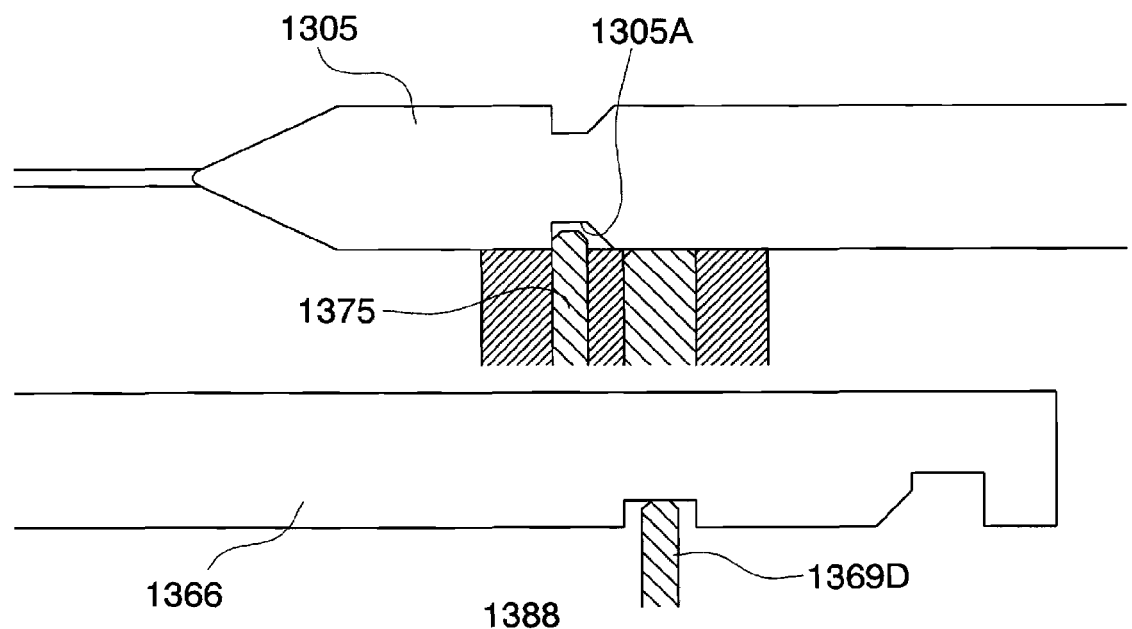
FIG. 51 shows the channel unit and the erroneous-movement-preventive section of the operation stick when the slider is fixed.

Drawing the slider section 1358 proximally and engaging the second engagement section 1388 of the connecting member 1366 with the engagement protrusion 1369D as shown in FIG. 51 cause the slider section 1358 to be supported by the engagement protrusion 1369D, thereby maintaining the bending state of second bending 308.

Figure 52:
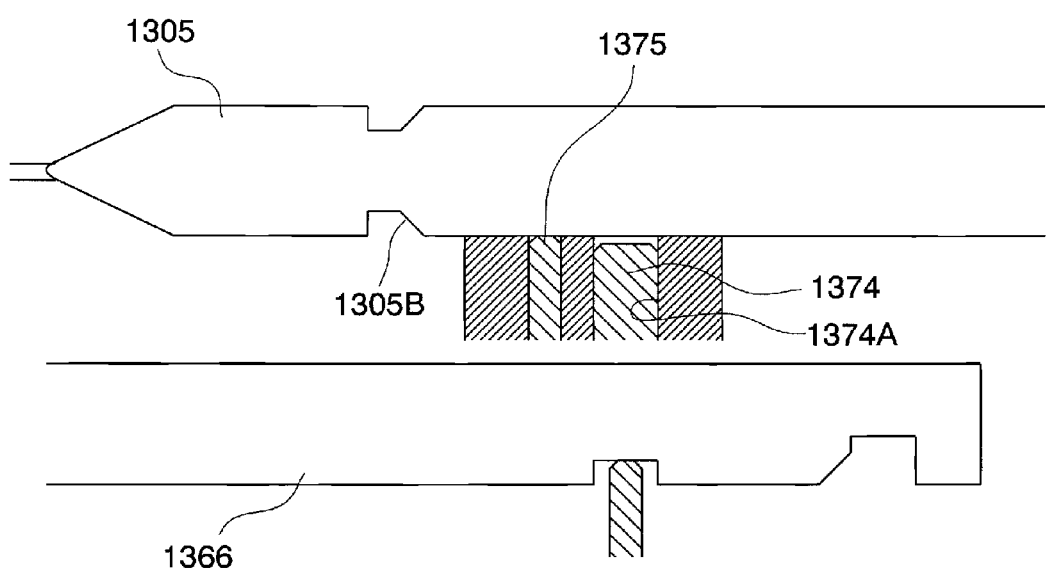
FIG. 52 shows the channel unit and the erroneous-movement-preventive section of the operation stick when the treatment instrument is further inserted.

Further advancing the procedure instrument 1305 as shown in FIG. 52 causes the taper surface 1305B to press down the second piston 1375 and the tip of the procedure instrument 1305 to protrude from the first arm section 302A, thereby manipulation is ready to be carried out. This state enables extension and retraction of the procedure instrument 1305 in the axial line direction. This state of first piston 1374 urged downwardly by a spring as shown in FIG. 52 is enclosed in the through-hole 1374A since the engagement piston 1369B is moved downwardly. Therefore, a friction force is not produced between the first piston 1374 and the procedure instrument 1305.

Subsequently, desirable manipulation is carried out by the same operation as that of the first embodiment by protruding the procedure instrument from the tip of the second arm section 302B.

Figure 53:
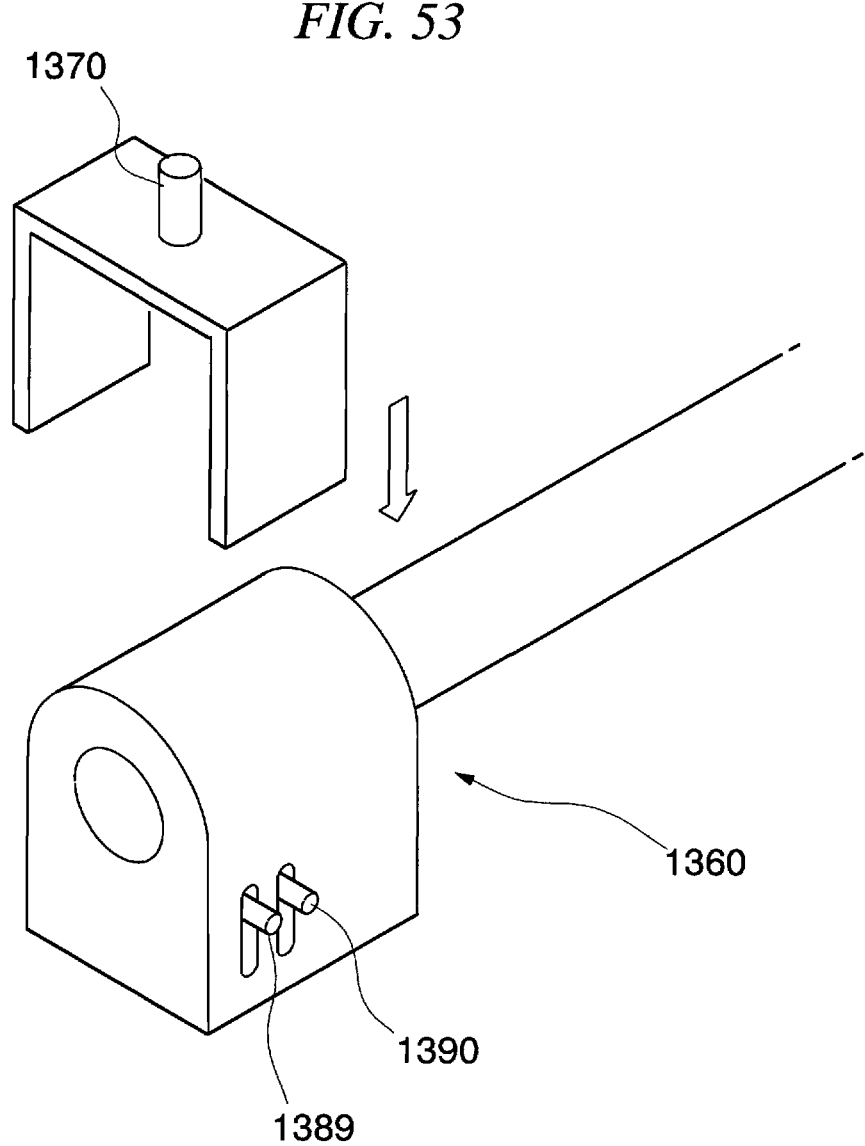
FIG. 53 shows a removal button and channel unit of the operation stick.
Figure 54:
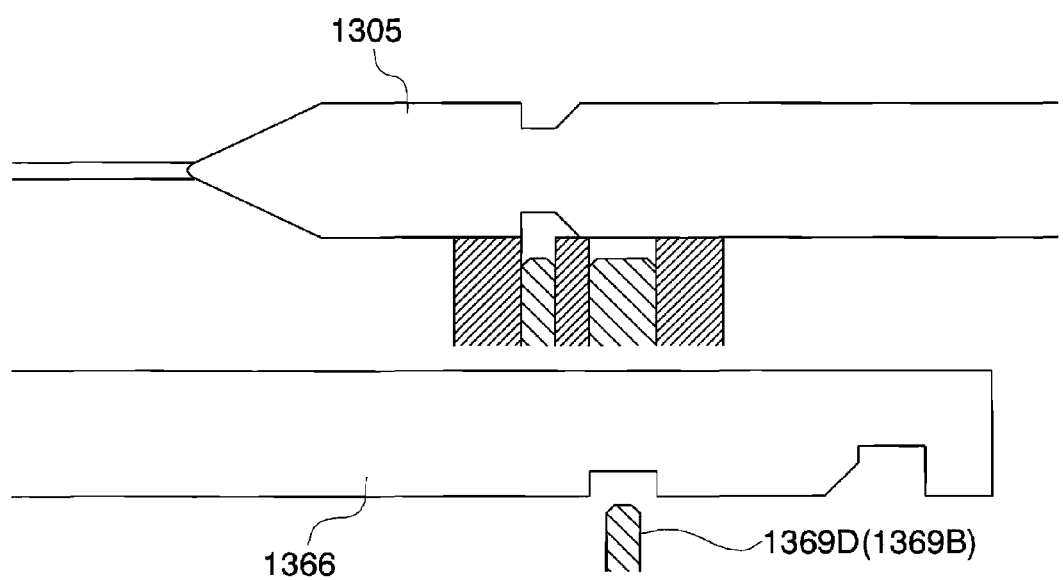
FIG. 54 shows the channel unit and the erroneous-movement-preventive section of the operation stick when the removal button is pressed.

Removal of the procedure instrument after ending the manipulation necessitates pressing the removal button 1370 (see FIG. 39). As shown in FIG. 53, pressing the removal button 1370 causes a first protrusion 1389 and a second protrusion 1390 that protrude relative to the outer periphery of the channel unit 1360 to be pushed down. Pressing down the first protrusion 1389 and the second protrusion 1390 extending from the first piston 1374 and the second piston 1375 respectively causes the first piston 1374 and the second piston 1375 to be pushed down as shown in FIG. 54. The disengagement between the second piston 1375 and the procedure instrument 1305 consequently enables removal of the procedure instrument 1305. Simultaneously, the first piston 1374 pushes down the engagement protrusion 1369D of the engagement piston 1369B and disengages the protrusion 1369D of the engagement piston 1369B from the connecting member 1366. The tension of the second-bending-operation wire causes the slider section 1358 to move ahead.

Manipulation using another procedure instrument may be maintained by insertion of the corresponding procedure instrument in accordance with the aforementioned method. Operations after ending all the manipulations will be explained as follows.

After removing the procedure instrument 1305, a lever 1386A (see FIG. 47) of the connecting member 1386 of the instrument channel 1384 is maneuvered to disengage the instrument channel 1384 from the channel unit 1360. Subsequently pulling up the fixed knob of the channel-fixing section 1377 causes the connecting section 1362 to be removed from the channel-fixing section 1377.

Subsequently pressing the release switch (see FIG. 39) 1367 causes the engagement jaws 1373 of the mating fixed section 1363 to be disengaged from the through-hole 1367A of the release switch 1367. Synchronously, the channel unit 1360A can be removed easily since the urging section 1368 pushes the channel unit 1360A proximally and the mating fixed section 1363 is exposed from the base end of the stick 1354A. The removed channel unit 1360A is discarded instantaneously, or cleaned and sterilized for reuse.

The medical treatment endoscope 1300 according to the present embodiment is detachable from the sticks 1354A and 1354B for operating the procedure instrument 1305 via the arm section and the channel unit 1360 including the channel for passing the procedure instrument therethrough. Therefore, manipulations in more sanitary conditions, that maintain the sterilized state of the channels can be conducted by rendering the channel unit 1360 a sterilized throwaway unit or by sterilization for reuse.

The number of operation units may vary desirably and correspond to the number of the arms of the arm section in contrast to the aforementioned embodiment explaining the example in which the operation section is provided with the first operation unit and the second operation unit. Also, a configuration may be free from the second-bending-wire unit and the third mating attachment section in a case where the arm section is not provided with the second bending part 308.

In addition, the position of the releasing switch is not limited to the present embodiment explaining an example attaching the release switch 1367 onto the upper surface of the fixture section 1359. An example thereof is as follows.

Figure 55:
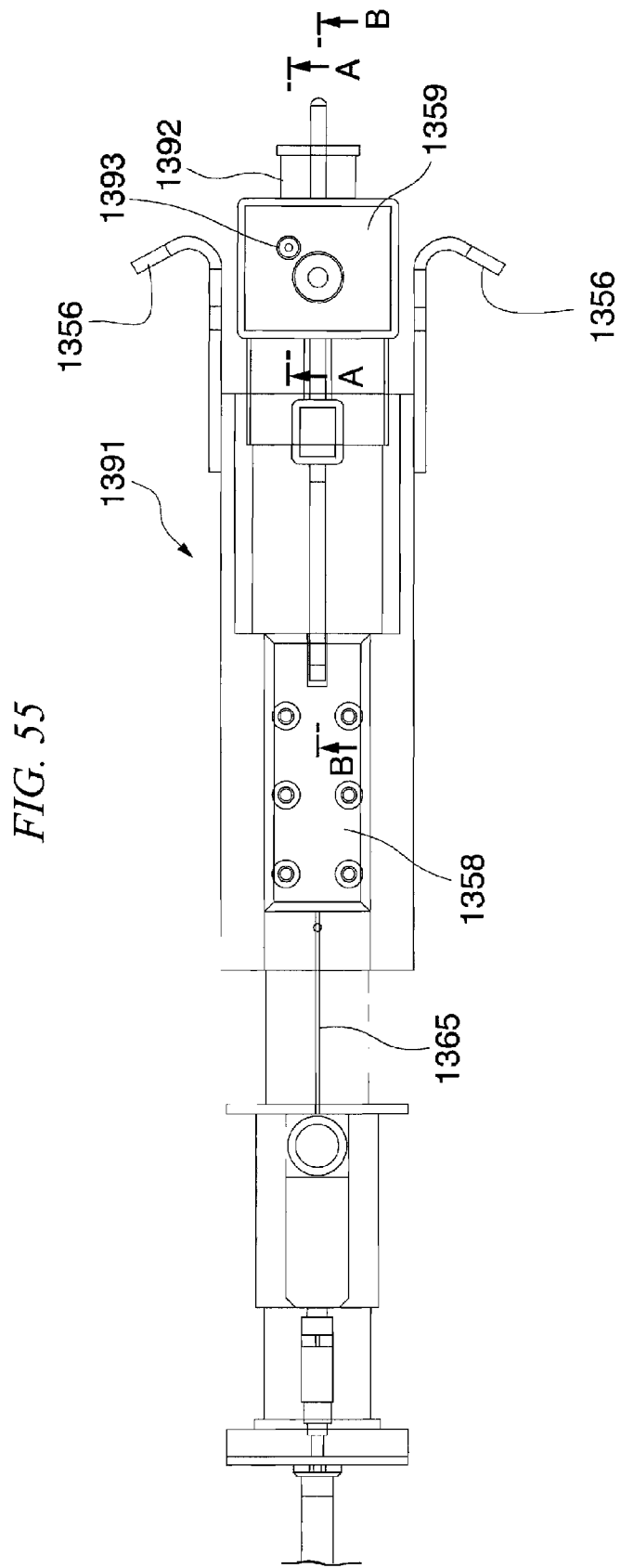
FIG. 55 is a bottom plan view showing an operation stick and a channel unit in accordance with a modified example of the medical treatment endoscope.
Figure 56:
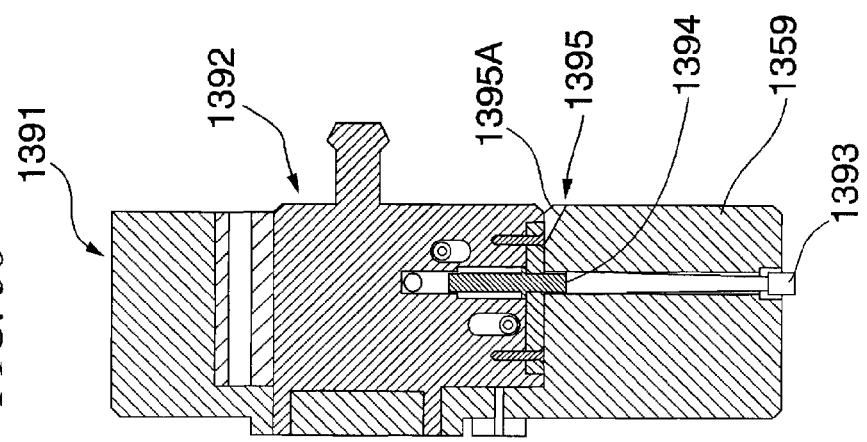
FIG. 56 is a cross-sectional view along the line A-A in FIG. 55.
Figure 57:
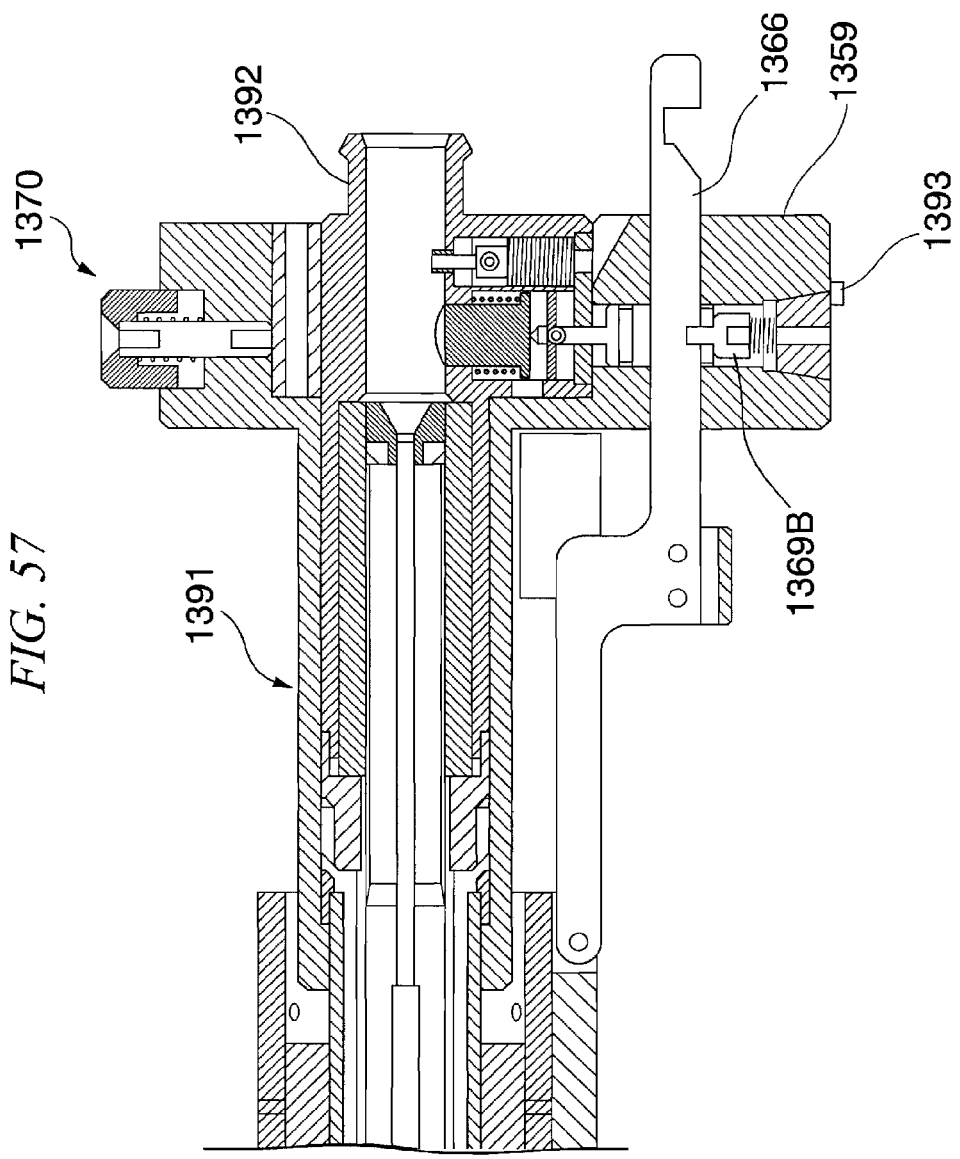
FIG. 57 is a cross-sectional view along the line B-B in FIG. 55.

FIG. 55 is a bottom plan view showing the stick 1391 and the channel unit 1392 in accordance with a modified example of the present embodiment. FIGS. 56 and 57 are cross-sectional views along the lines A-A and B-B in FIG. 55 respectively.

As shown in FIGS. 55 to 57, the release switch 1393 is separately disposed on the bottom surface of the fixture section 1359 above the axial line in the longitudinal direction of the stick 1391 having the connecting member 1366 attached thereto. In addition, an oblique surface is not formed to the tip of the engagement jaws 1394 provided to the channel unit 1392. Alternatively, forming an oblique surface on an inner wall 1395A making contact with the engagement jaws 1394 in an opening 1395, into which the channel unit 1392 is inserted, facilitates insertion of the channel unit 1392 into the stick 1391. This configuration providing smooth insertion of the channel unit 1392 into the stick 1391 can also support the both components unitarily.

Also, providing two finger-hook sections 1356 as shown in FIG. 55 permits two-hand operation to the slider section, thereby providing easy operation to a not so muscular user.

Figure 58:
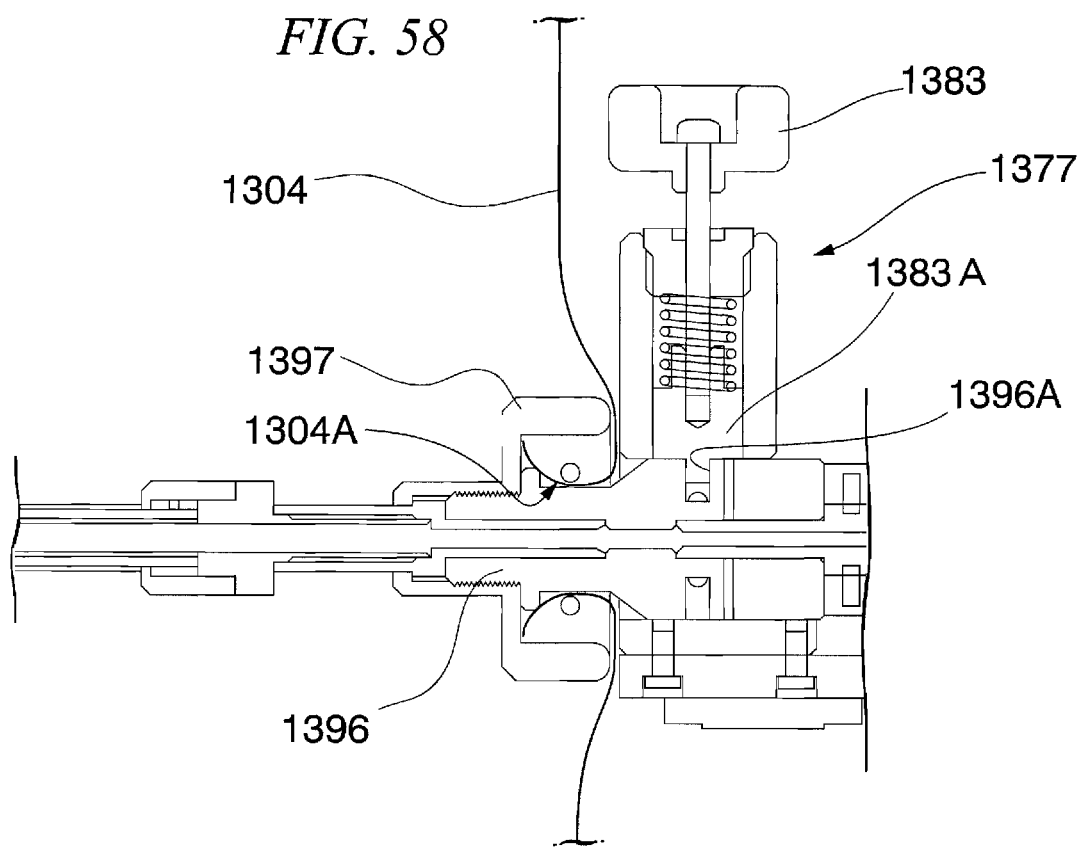
FIG. 58 shows the channel unit and an instrument channel in accordance with the modified example of the medical treatment endoscope.

In addition, another modified example as shown in FIG. 58 may be provided in which a connection section 1396 of the channel unit may be screwed into a connection member 1397 of the instrument channel formed like a cap in place of the present embodiment explaining an example engaging the connection member provided in the vicinity of the base end of the instrument channel with the connecting part of the tip of the channel unit. Accordingly, possibility of contamination can be reduced more significantly since an increased-diameter section of the connection member 1397 can cover an inner surface 1304A of the drape 1304 which will be exposed and contaminated when the drape 1304 is torn.

In addition, inserting the connection section 1396 into, in this case, the channel-fixing section 1377 causes a shaft 1383A connected to the fixed knob 1383 to engage with a groove 1396A provided on the outer periphery of the connection section 1396. This prevents the connection section 1396 from being removed from the channel-fixing section 1377.

Figure 59:
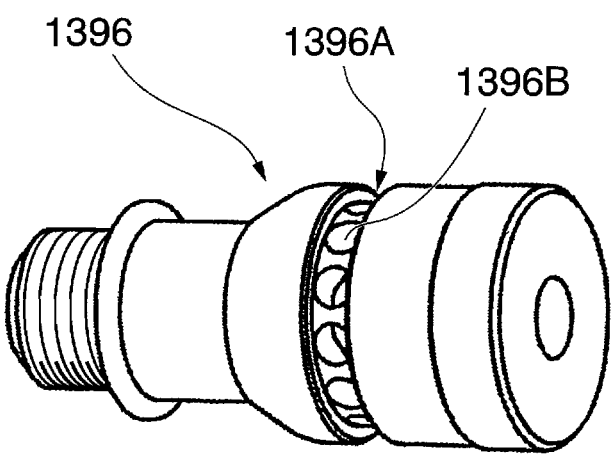
FIG. 59 is perspective view showing a connection section of the channel unit.

Rotating to remove this state of first cap 1381 based on a screw engagement method causes the connection section 1396 to rotate so as to connect to the procedure instrument channel. Accordingly, the shaft 1383A enters one of a plurality of holes 1396B provided to the groove 1396A, thereby immobilizing the connection section 1396 to be fixed to the channel-fixing section 1377 (see FIG. 59). Therefore, attaching the connection member 1397 to the connection section 1396 by using the screw engagement method is in no need of fixing the connection section 1396 manually to prevent the rotation thereof, thereby facilitating the connection of both components. It should be noted that the hole 1396B does not have to have a through hole formed therethrough as long as the hole 1396B has a recessing shape (recessed section) which is capable of engaging with the shaft 1383A. For example, the hole 1396B may have a bottom having a recessed section.

Figure 60A:
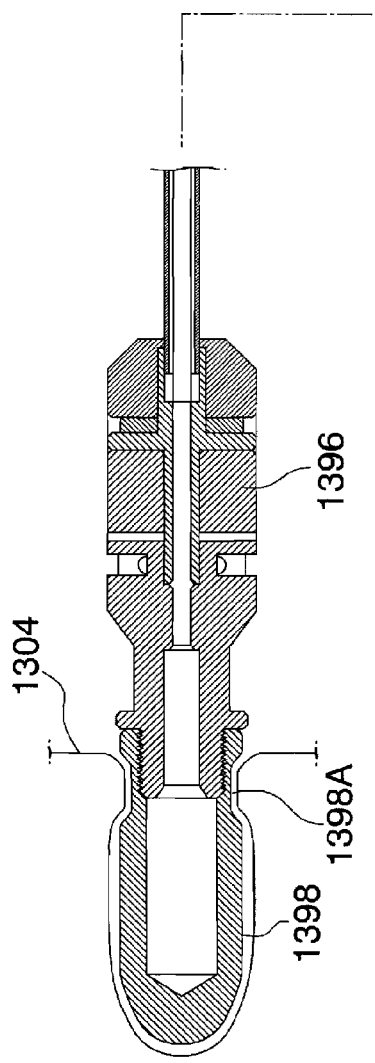
FIGS. 60A and 60B are cross-sectional views showing the channel unit in accordance with the modified example of the present invention.
Figure 60B:
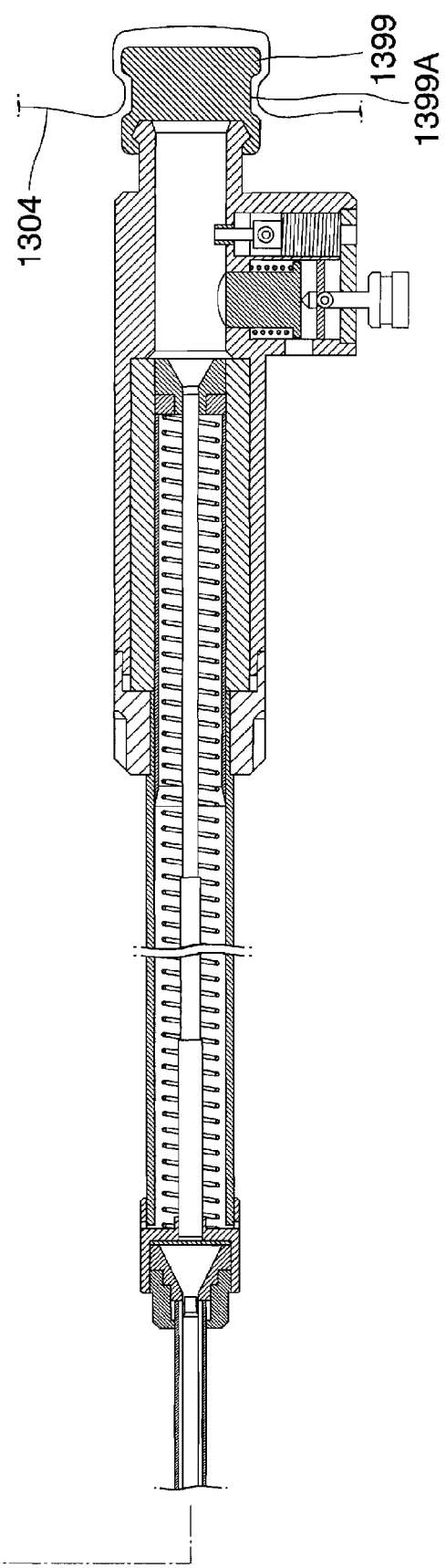

In addition, as shown in modified examples shown in FIGS. 60A and 60B, a first cap 1398 and a second cap 1399 may have fixture sections 1398A and 1399A which have a reduced diameter on a part of the outer peripheries respectively. Accordingly, the drape 1304 can be fixed by, for example, a tape, easily, and a part of the drape 1304 can be removed together with the caps 1398 and 1399.

Third Embodiment

In the medical treatment endoscope according to the present embodiment, a second piston for preventing removal of the procedure instrument 1305 is disposed in the vicinity of a tip relative to a first piston linking with an erroneous-movement-preventive section.

Structural elements that are equivalent in the following explanation will be assigned the same numeric symbols and redundant explanations thereof will be omitted.

Figure 61:
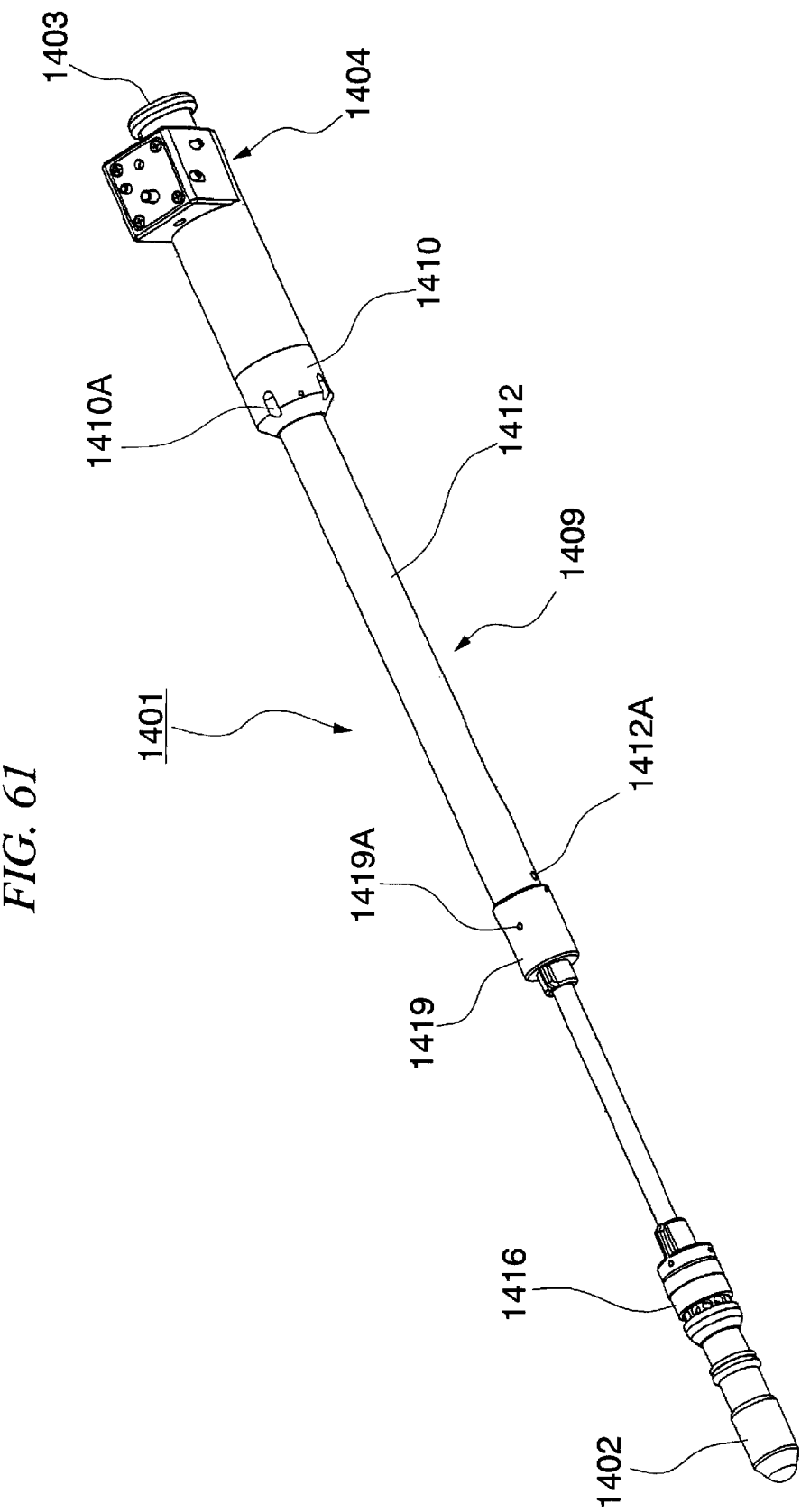
FIG. 61 is a perspective view showing the channel unit in the medical treatment endoscope according to a third embodiment of the present invention.

FIG. 61 is a perspective view showing a channel unit 1401 in the medical treatment endoscope according to the present embodiment. Aside from a few reusable types, the channel unit 1401 undertaking cleaning or sterilization is made of a stainless steel SUS 303 to resist autoclave sterilization. SUS 304 may be used in place of SUS 303. In addition, it is preferable that at least screw engagement portions of a connecting member 1424 and a mating fixture section 1404 engaging with a first cap 1402 and a second cap 1403 respectively for maintaining a sterilized state in the channel unit 1401 be made of SUS 303 or 304. Autoclaving method in this manner readily provides preferable sterilization to the screw engagement portions.

The channel unit 1401 is formed so that the connecting member 1424 in the vicinity of the tip of a metal hardware member has the most reduced diameter while the diameter increases gradually toward the proximal end so as to provide smooth insertion into an operation stick 1430, which will be explained later.

Figure 62:
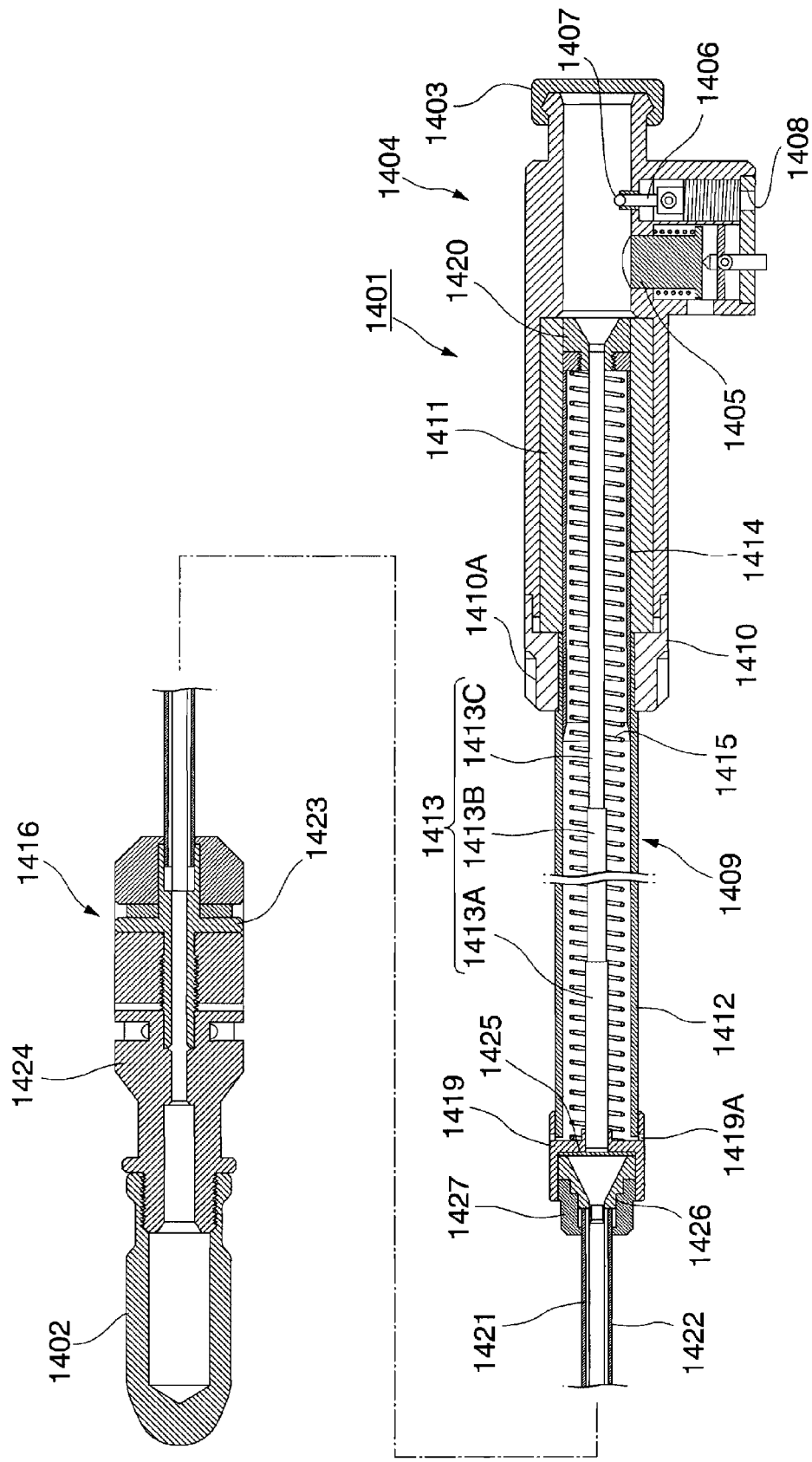
FIG. 62 is a cross-sectional view of the channel unit.

FIG. 62 is a cross-sectional view of the channel unit 1401. A first piston 1405 provided to the mating fixture section 1404 and engaging with a second-bending-link-engagement section 1431 of the operation stick 1430 regulates extension and retraction of a sliding member 1436, which will be explained later, provided to the operation stick 1430 for operating the second-bending-wire unit 1303. A second piston 1406 for preventing removal of the procedure instrument 1305 (not shown in the drawings) inserted in a channel in the channel unit 1401 is provided in the vicinity of the base end relative to the first piston 1405.

Most of the functions and movements of the second-bending-link-engagement section 1431 are the same as those of the erroneous-movement-preventive section 1369 according to the second embodiment. Different points will be explained later.

A freely rotatable ball 1407 provided to a tip of the second piston 1406 protruding into the channel reduces friction produced during extension and retraction of the procedure instrument 1305 in the channel. This results in reducing operator's burdensome operation, thereby enabling accurate extension and retraction of the procedure instrument 1305. High pressure injection of cleaning liquid, etc. into a through-hole 1408 provided on the outer periphery of the mating fixture section 1404 and communicating to a space in which the second piston 1406 makes a sliding movement allows the outer periphery of the ball 1407 to be cleaned.

The aforementioned configuration using the example having the separable operation stick and the channel unit using pistons 1405 and 1406 is applicable to a configuration using the two components in one unit.

A fixture member 1410 using screw engagement for connecting and fixing the mating fixture section 1404 to a main body 1409 is attached to a tip of the mating fixture section 1404. A plurality of groves 1410A for facilitating removal are provided to the fixture member 1410. A substantial U-shaped cross section of the inner surface of each grove 1410A, orthogonal to the axial line, formed in a curved surface free from sharp edges facilitates cleaning thereof. The bearings disposed on the inner surface of the linear bush 1411 and damaged by chemicals or in sterilization processes can be replaced easily since removing the fixture member 1410 allows a linear bush 1411 attached in the mating fixture section 1404 to be taken out.

The main body 1409 connected to the mating fixture section 1404 is provided with: an outer pipe 1412 forming the outer periphery thereof; a channel pipe 1413 inserted into the outer pipe 1412; a slide pipe 1414 attached to the base end of the channel pipe 1413; and a spring 1415 urging the slide pipe 1414 toward the base end.

The outer pipe 1412 is a cylindrical member having the tip connected to a connecting section 1416 connected to the instrument channel and the base end connected to the mating fixture section 1404 via the fixture member 1410. As shown in FIG. 61, a drain hole 1412A provided on the outer periphery of the outer pipe 1412 provides desirable circulation and drainage of the cleaning liquid injected into the channel unit 1401.

Figure 63:
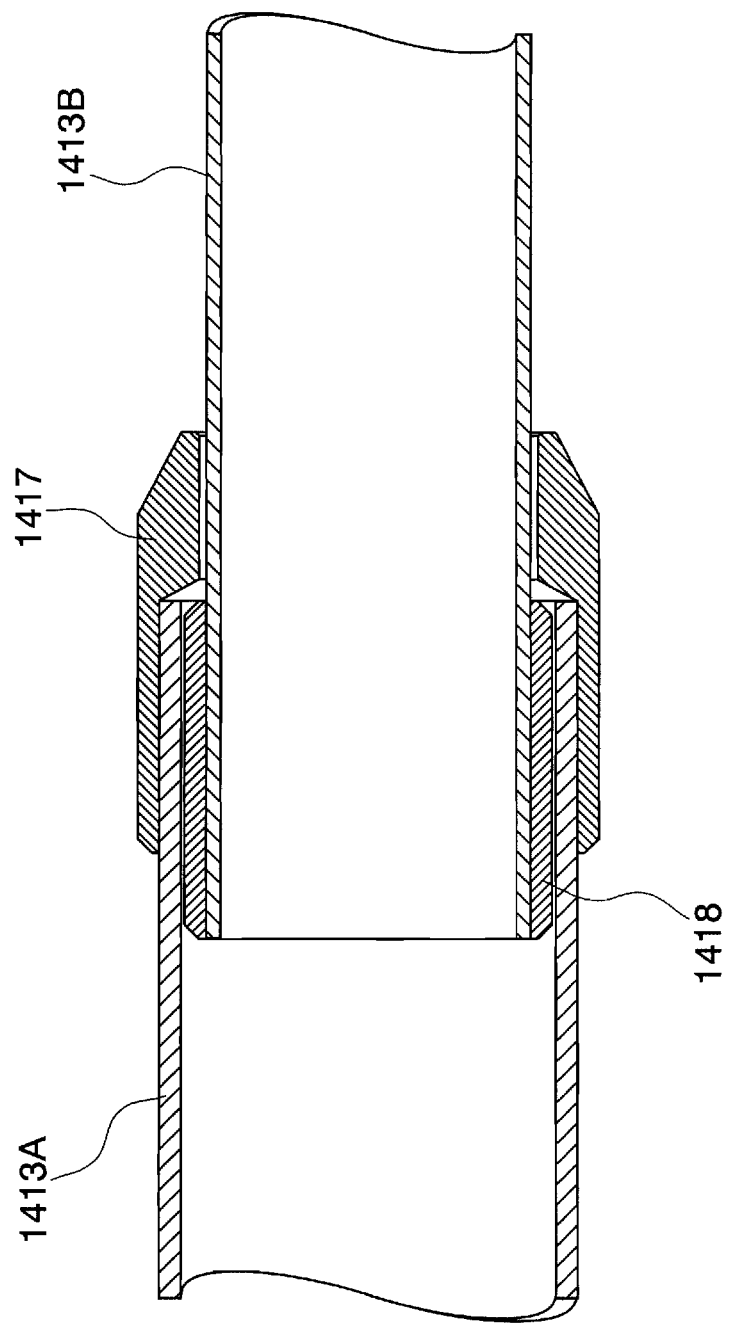
FIG. 63 is a cross-sectional view of the channel pipe of the channel unit in magnified view.

The channel pipe 1413 having a lumen serving as a channel which allows insertion of the procedure instrument 1305 therethrough has three pipes including a first pipe 1413A, a second pipe 1413B, and a third pipe 1413C. The inner diameter of the distally provided first pipe 1413A is greater than the outer diameter of the second pipe 1413B connected to the base end thereof allows the second pipe 1413B to extend into the first pipe 1413A and allows a part of the second pipe 1413B to be enclosed in the first pipe 1413A. A substantial ring-shape first stopper 1417 attached to the base end of the first pipe 1413A as shown in FIG. 63 in magnified view and making contact with a second stopper 1418 attached to the tip of the second pipe 1413B prevents removal of the second pipe 1413B from the first pipe 1413A. Significant clearances obtained between the inner periphery of the base end of the first stopper 1417 and the second pipe 1413B and between the inner periphery of the first pipe 1413A and the outer periphery of the second stopper 1418 provide smooth extension and retraction of the second pipe 1413B in the first pipe 1413A. In addition, a taper tip and a taper base end of the outer periphery of the first stopper 1417 formed to have gradually reduced outer diameters prevent the spring 1415 from hooking thereinto.

A third stopper and a fourth stopper (not shown in the drawing) having the same shape as the first stopper 1417 and the second stopper 1418 and attached to the base end of the second pipe 1413B and to the tip of the third pipe 1413C connected respectively allow the third pipe 1413C to extend into the second pipe 1413B, thereby allowing a part of the third pipe 1413C to be enclosed in the second pipe 1413B.

The third pipe 1413C slides in the outer pipe 1412 unitarily with the slide pipe 1414 since the base end of the third pipe 1413C fixed to the tip of a member 1420 has a shape allowing the procedure instrument 1305 to make contact therewith; and the member 1420 using screw engagement is fixed to the slide pipe 1414. Also, the screw engagement between the third pipe 1413C and the slide pipe 1414 permits dissembling and cleaning of the two components separately.

The tip of the first pipe 1413A is brazed and fixed to a mouthpiece 1419. Visual inspection readily permits observation of a brazed portion seeping from a hole 1419A provided to the mouthpiece 1419.

The outer diameter of the slide pipe 1414 is set to be slightly smaller than the inner diameter of the outer pipe 1412. The aforementioned member 1420 attached to a base end 1414A of the slide pipe 1414 causes the procedure instrument 1305 inserted in the channel unit 1401 to push the member 1420, thereby allowing the slide pipe 1414 and the third pipe 1413C to move distally. A taper end surface of the tip of the slide pipe 1414 having an inner diameter increasing gradually toward the tip prevents hooking of the spring 1415 onto the slide pipe 1414 while making extending and retracting movements in the outer pipe 1412.

The coil spring 1415 made of metal, etc., has a loop having three channel pipes 1413 inserted therethrough. The spring 1415 is inserted in the slide pipe 1414. The base end of the spring 1415 making contact with a part having the third pipe 1413C fixed thereto urges the slide pipe 1414 to be positioned in the mating fixture section 1404 prior to insertion of the procedure instrument 1305.

The loop diameter of the spring 1415 is set to be smaller than the inner diameter of the slide pipe 1414 slightly and greater than the outer diameter of the channel pipe 1413 significantly so that inconcentric disposition of the spring 1415 relative to the outer pipe 1412 in the outer pipe 1412 may resist interference with the first stopper 1417.

The connecting section 1416 is connected to the main body 1409 via a flexible tube 1421. The outer periphery of the tube 1421 is coated by a cylindrical blade 1422 formed by weaving metal wires. The blade 1422 curbing the extension of the tube 1421 in the axial line direction prevents the tube 1421 making extension and contraction from absorbing the extension and retraction of the procedure instrument, thereby allowing the extension and retraction of the procedure instrument to be transferred to the tip of the procedure instrument reliably.

The tip of the tube 1421 is fixed to a fitting member 1423 fixed by screw engagement to the connecting member 1424 connecting to the instrument channel. Adjusting the length of screw engagement between the fitting member 1423 and the connecting member 1424 absorbs variation in length of the tube 1421 produced while assembling the channel unit 1401, thereby facilitating manufacturing of the channel unit 1401.

The base end of the tube 1421 is fixed to the mouthpiece 1419. A vent valve 1425 provided between the tube 1421 and the channel pipe 1413 of the main body 1409 ensures airtightness in an area ahead of the channel pipe 1413. A washer 1426 presses and fixes the vent valve 1425 in the axial line direction of the channel unit 1401. A fastening member 1427 engaging with the mouthpiece 1419 by screw engagement fixes the washer 1426 and the base end of the tube 1421 onto the vent valve 1425. Accordingly, air-tightness can be maintained reliably since the vent valve 1425 upon undergoing screw engagement is free from a twisting force acting thereonto around the axial line.

Figure 64:
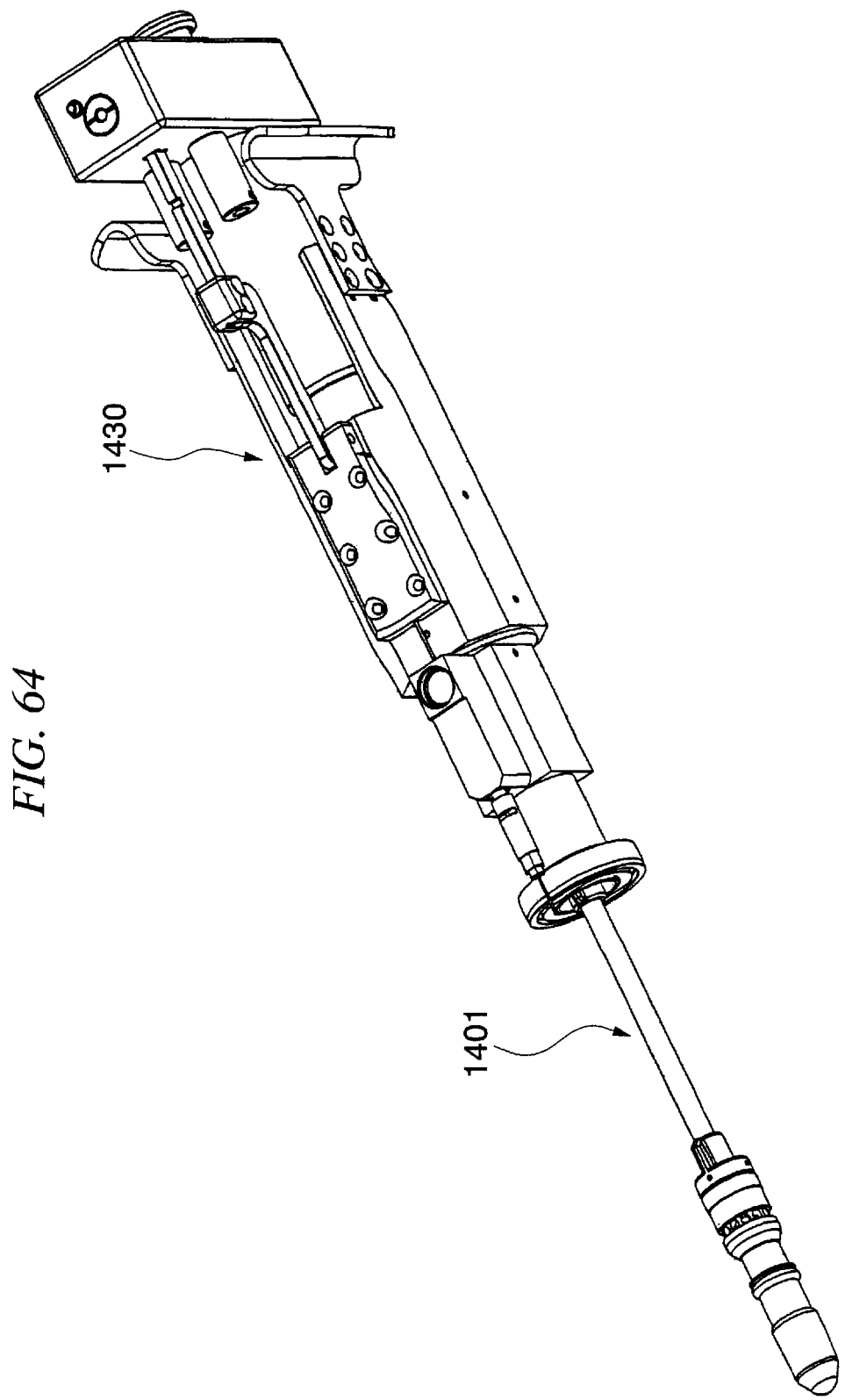
FIG. 64 is a perspective view showing an operation stick having a channel unit inserted therethrough.

FIG. 64 is a perspective view showing the operation stick 1430 having the channel unit 1401 inserted therethrough. A stainless steel SUJ2 or SUS 420J2 is used to improve the endurance of a pipe 1438 (see FIG. 65) of the operation stick 1430. It is preferable to harden the aforementioned materials to obtain 58 HRC (Rockwell Hardness C-Scale) or greater if necessary, and it is further preferable to provide anti-corrosion coating, e.g., hard chromium electroplating. This allows the first pipe 1413A to resist damage caused by the bearing disposed on the inner periphery of the linear bush 1436A attached to the sliding member 1436 which will be explained later.

In addition, the outer periphery of the operation stick 1430 is fully chamfered and formed not to have sharp edge sections which will tear a drape 1034 covering the operation section onto which the operation stick 1430 is attached. This configuration prevents an unsterilized section from being exposed when the medical treatment endoscope is operated.

Figure 65:
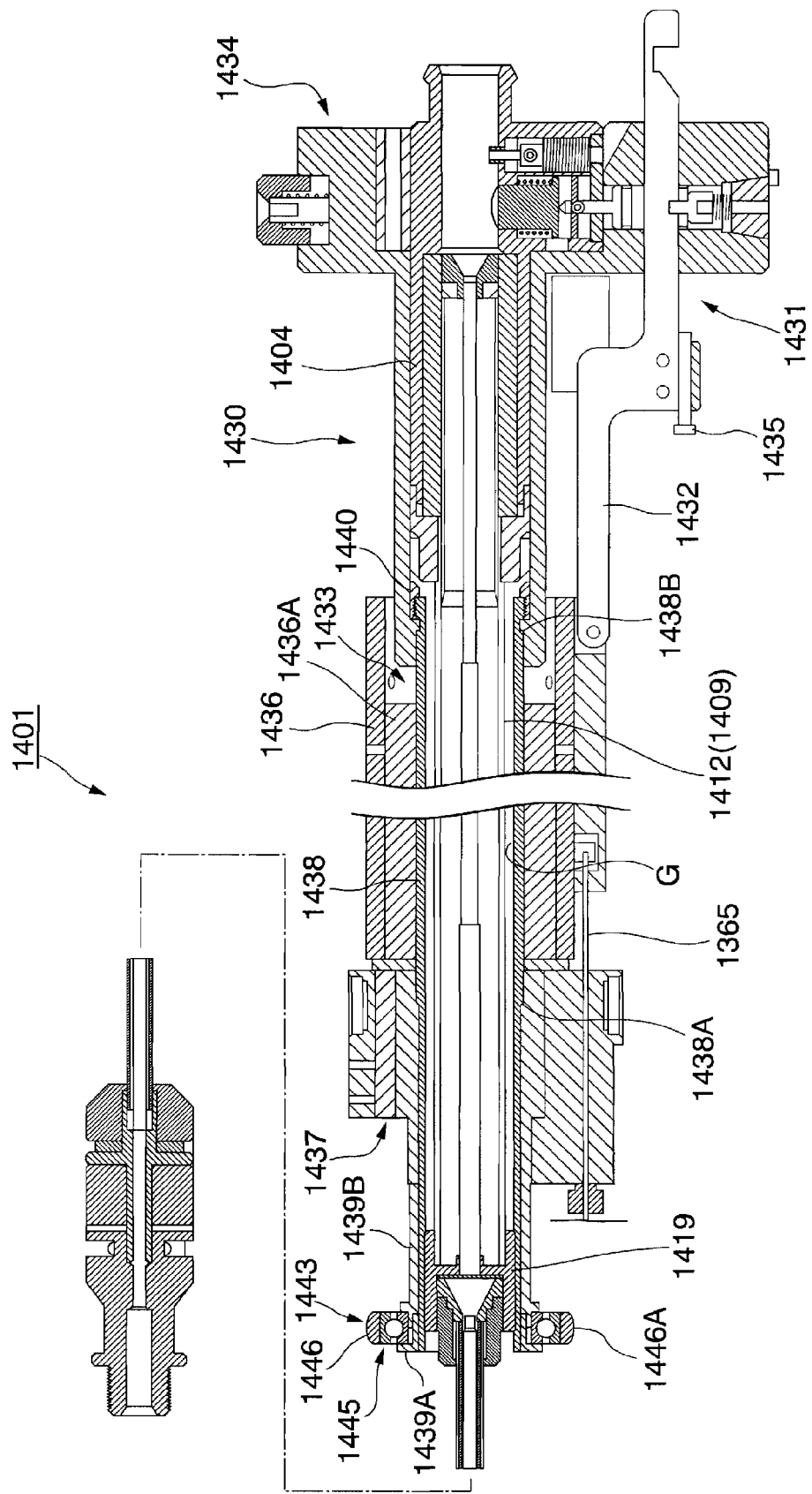
FIG. 65 is a cross-sectional view of the operation stick having the channel unit inserted therethrough.

FIG. 65 is a cross-sectional view showing the operation stick 1430 having the channel unit 1401 inserted and fixed therethrough. The outer diameter of the channel unit 1401 corresponding to the mating fixture section 1404 is substantially the same as the inner diameter of the operation stick 1430; thus, the channel unit 1401 makes substantial close contact with the operation stick 1430.

On the other hand, the outer pipe 1412 of the main body 1409, the mouthpiece 1419, and inner periphery of the operation stick 1430 defines a constant clearance G. This provides smooth insertion of the channel unit 1401 into the operation stick 1430 since the aforementioned clearance G absorbs the shift of axial lines between the main body 1409 and the mating fixture section 1404. The force applied onto the channel unit 1401 while operating the procedure instrument 1305 is transferred to the operation stick 1430 and the operation section mainly via the mating fixture section 1404 disposed in the vicinity of the linear bush 1411.

The tip of a crank-shaped connecting member 1432 of the second-bending-link-engagement section 1431 is in the vicinity of a tubular main body 1433 closely. This configuration will meet fewer interference between the operation stick 1430 and the enclosure 1379 of the operation section during operation thereof since the size of the main body 1433 including the connecting member 1432 in the vertical direction can be further reduced. In addition, the crank shape of the connecting member 1432 made of stainless steel SUS 420J2 provides resistance to the bending stress.

A stopper 1435 attached to the connecting member 1432 by screw engagement protrudes toward a fixture section 1434 having the second-bending-link-engagement section 1431 provided thereon. Drawing the sliding member 1436 proximally by a predetermined length causes the tip of the stopper 1435 to make contact with the outer periphery of the fixture section 1434, thereby preventing further proximal retraction of the sliding member 1436. This prevents rupture, etc., of the operation member 1365 for operating the second bending part 308 caused by drawing the sliding member 1436 excessively. The protrusion of the stopper 1435 in length toward the fixture section 1434 is adjustable within a predetermined range by adjusting the screw engagement in length with the connecting member 1432.

An attachment section 1437 for fixing the operation stick 1430 onto the enclosure 1379 of the operation section is attached to the main body 1433. The attachment section 1437 is attached ahead the center of the operation stick 1430 in the longitudinal direction. The operation stick 1430 attached to the enclosure 1379 (not shown in the drawing) and operated by the procedure instrument 1305 (not shown in the drawing) inserted therethrough swings vertically and horizontally around the attachment section 1437 attached ahead of the tip relative to the center of the operation stick 1430 in the longitudinal direction reduces the swinging amount of the tip of operation stick 1430, thereby preventing interference between the two operation sticks for operating the laterally disposed arm sections 302A and 302B.

Figure 66:
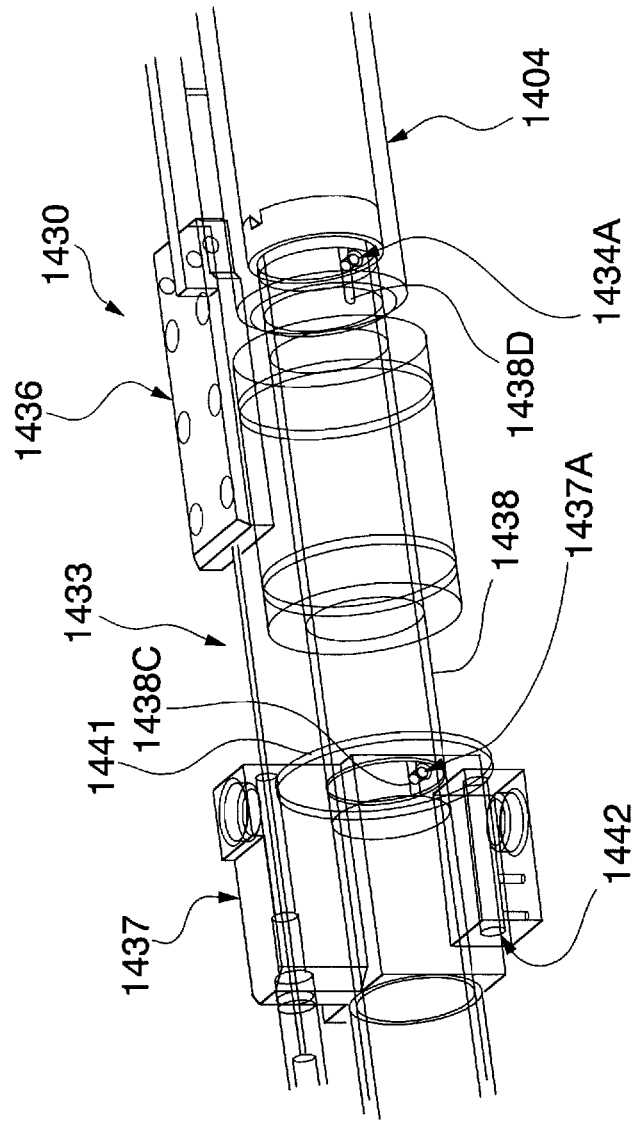
FIG. 66 is a perspective view showing a main body of the operation stick in magnified view.

FIG. 66 is a perspective view showing the main body 1433 of the operation stick 1430 in a magnified view. As shown in FIG. 66, the attachment section 1437 and the fixture section 1434 are attached from the outside of the pipe 1438 constituting a main part of the main body 1433 and fixed thereon. As shown in FIG. 65, the thickness of the tip of the pipe 1438 and the thickness of the base end of the pipe 1438 are shallow where steps 1438A and 1438B are provided respectively. The attachment section 1437 and the fixture section 1434 in the axial line direction of the pipe 1438 are fixed by inserting the pipe 1438 into a lumen from the tip and the base end of the pipe 1438 respectively while inserting the sliding member 1436 therebetween and making contact with the step 1438A and 1438B. The position of the attachment section 1437 around the axial line of the pipe 1438 and the position of the fixture section 1434 around the axial line of the pipe 1438 are maintained desirably by engaging a fixture screw 1437A protruding into the lumen of the attachment section 1437 to a groove 1438C provided to the tip of the pipe 1438 and by engaging a fixture screw 1434A protruding into the lumen of the fixture section 1434 to a groove 1438D provided to the base end of the pipe 1438 as shown in FIG. 66. The attachment section 1437 and the fixture section 1434 positioned in the axial line direction around the axial line of the pipe 1438 are fixed by: a tip member 1439A engaged with the tip of the pipe 1438 by screw engagement; a spacer 1439B pushed by the tip member 1439A; and a fitting member 1440 engaged with the base end of the pipe 1438 by screw engagement. This structure allows the attachment section 1437 and the fixture section 1434 to be fixed at constant positions around the axial line of the pipe 1438. In addition, the attachment section 1437 and the fixture section 1434 can be fixed to the pipe 1438 reliably by screw engagement while the operation member 1365 is reliably attached to the operation stick 1430.

As shown in FIG. 66, a silencing member 1441 made of collision-absorbing material, for example, rubber, etc. is attached in the vicinity of the base end of the attachment section 1437. The silencing member 1441 urged toward the base end by a plunger 1442 having substantial the same structure as that of the urging section 1368 provided to the fixture section 1434 upon making contact with the sliding member 1436 absorbs collision and prevents large sound when the second bending part 308 of the arm section is restored to a linear state and when the sliding member 1436 is extended. It should be noted that a certain extent of silencing effect can be obtained by providing one of the silencing member 1441 and the plunger 1442.

Figure 67:
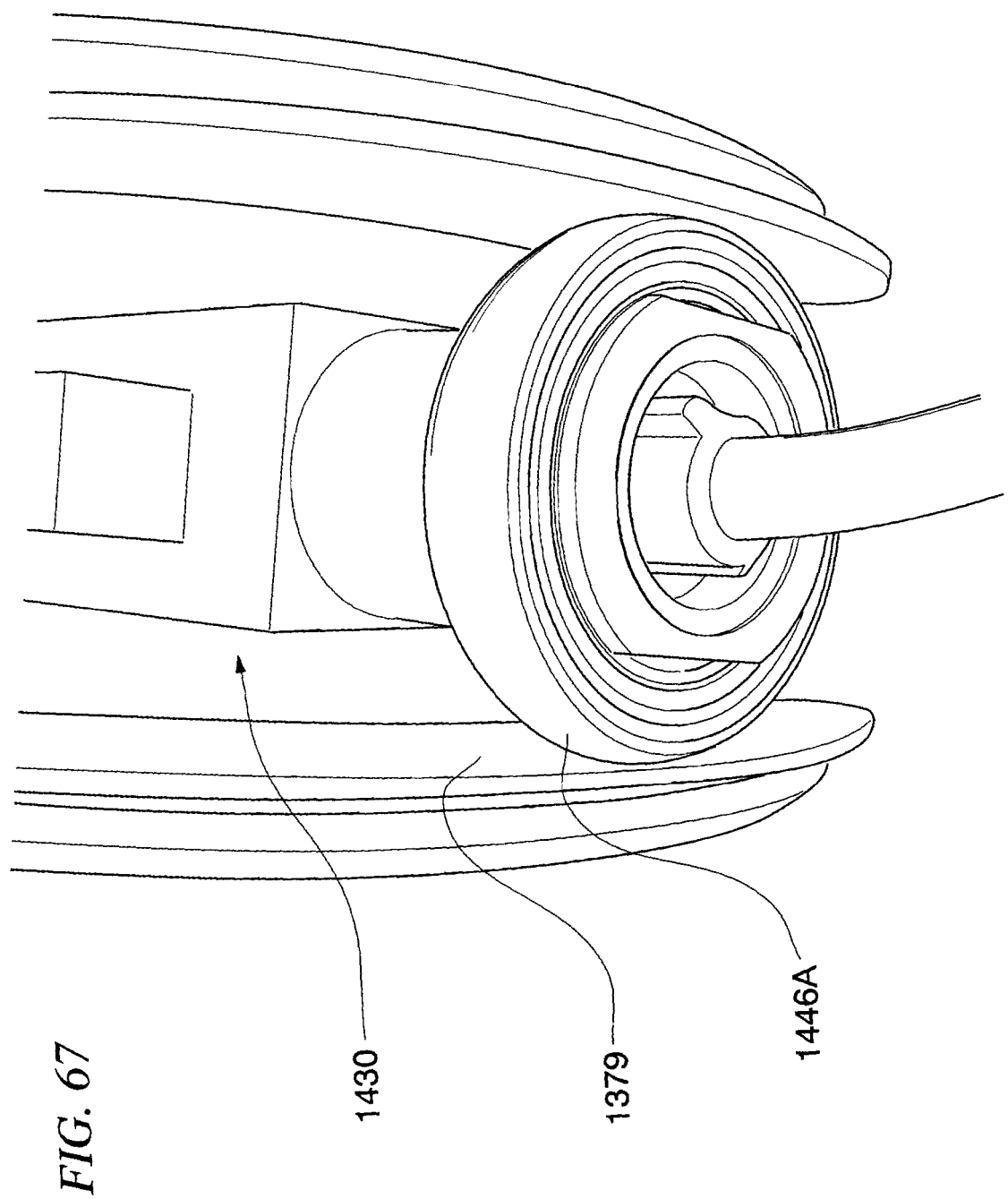
FIG. 67 shows a tip of the operation stick attached to the operation section.
Figure 68:
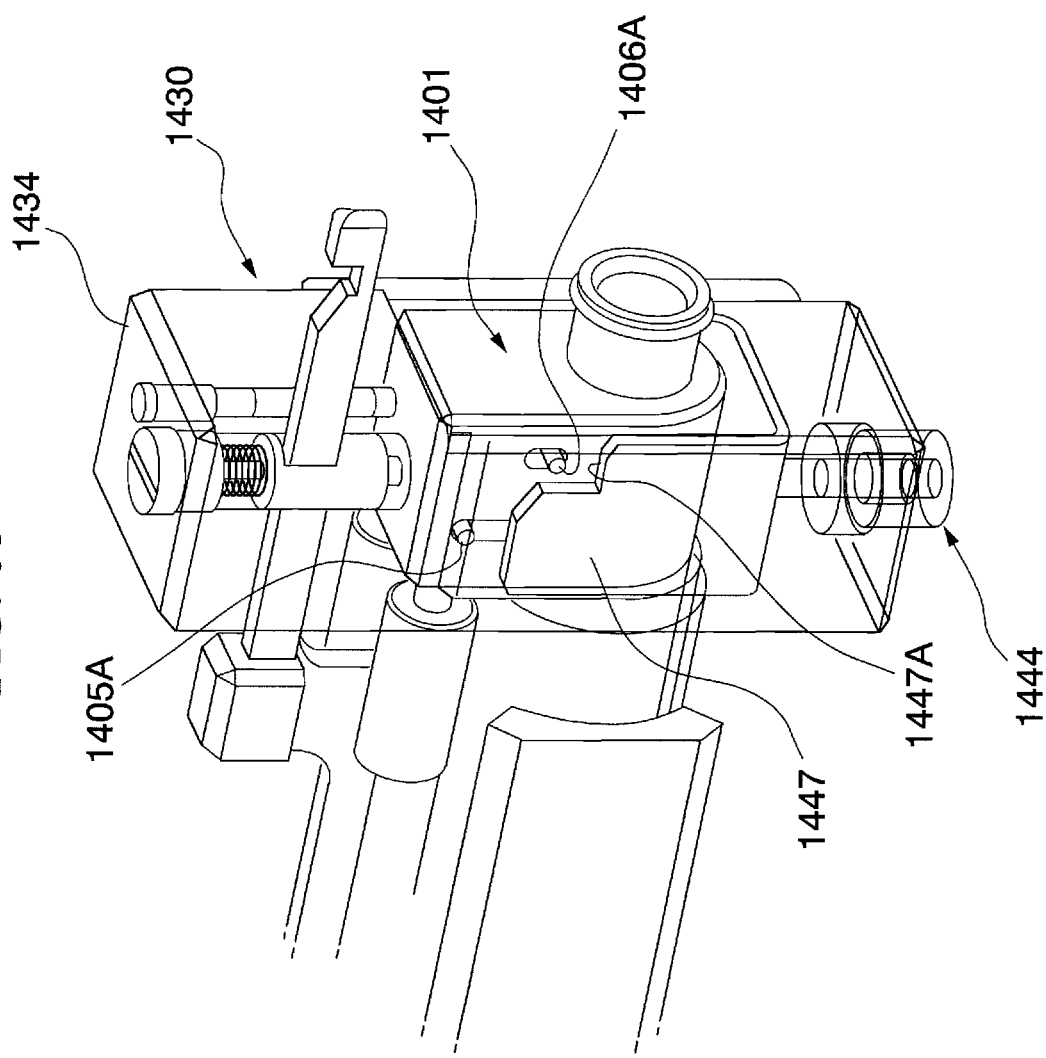
FIG. 68 shows a removal button of the operation unit.

As shown in FIG. 65, a ball bearing 1445 is attached to the tip of the tip member 1439A for fixing the spacer 1439B. A flange section 1443 is formed by a cap 1446 attached around the outer periphery of the ball bearing 1445. It is preferable that an outer periphery 1446A around the axial line of the cap 1446 is formed spherical, and it is further preferable that the outer periphery 1446A is formed on the central axis of the cap 1446 so that a sphere substantially coincides with a surface of a virtual ball having the center corresponding to a point in the middle in the axial line direction. This prevents play during operation since operating the operation stick 1430 in any direction causes the outer periphery 1446A to make point-contact with the enclosure 1379 in the operation section as shown in FIG. 67.

Pressing a first protrusion 1405A and a second protrusion 1406A substantially simultaneously cause the piston 1405 and 1406 to activate simultaneously since the first protrusion 1405A protruding from the first piston 1405 is disposed above the second protrusion 1406A protruding from the second piston 1406 in the channel unit 1401 according to the present embodiment, and since a step 1447A is provided to a U-shaped hardware 1447 connected to a removal button 1444 provided to the fixture section 1434 of the operation stick 1430.

It should be noted that adjusting the shape of the step 1447A so that the first protrusion 1405A can be pressed slightly faster than the second protrusion 1406A causes the first piston 1405 to be pushed and causes the sliding member 1436 to extend distally at first, thereby dispose the second bending part 308 of the arm section in linear state. The second piston 1406 pushed subsequently provides removable state to the procedure instrument 1305, thereby facilitating removal of the procedure instrument.

The second piston 1406 according to the present embodiment prevents falloff of the procedure instrument 1305 inserted in the channel unit 1401 in the medical treatment endoscope similarly to the aforementioned second embodiment. In addition, the sliding member 1436 for operating the second bending part 308 of the arm section can be engaged to the second-bending-link-engagement section 1431 reliably and supported there. In addition, the connecting member 1432 of the second-bending-link-engagement section 1431 engaging with an engagement piston closer to the tip to support the sliding member 1436 reduces distal protrusion of the connecting member 1432. This results in providing the more compact operation stick 1430 and facilitating the operation thereof.

It should be noted that the aforementioned preferred embodiments of the present invention do not limit the present invention. The configuration of the present invention allows for additions, omissions, substitutions and further replacements without departing from the spirit and scope of the present invention.

For example, the aforementioned embodiment explaining that the operation member 1365 for operating the second bending part 308 of the arm section is attached to the sliding member 1436 may be replaced by a configuration in which an end section of the operation member 1365 is fixed to an end section of a rotatable lever attached to the operation stick. Rotating this case of lever allows the second bending section to be operated.

Furthermore, it should be noted that the present invention is limited by the scope of claims attached hereto, and not by the aforementioned explanations.

What is claimed is:

1. A medical apparatus comprising:
    a flexible sheath;
    a procedure instrument having a treatment section provided at a distal end of the procedure instrument;
    an arm section having a first bending part capable of a bending operation and a first channel capable of inserting the treatment section therethrough and capable of protruding therefrom, the arm section being disposed to protrude from a tip of the sheath;
    an operation stick having a second channel connected to the first channel and inserting the procedure instrument therethrough, and a bending operating part connected to the arm section by an operation-transmission member; and
    an operation part provided in a proximal end side of the procedure instrument for operating the treatment section, wherein
    the procedure instrument is configured to be capable of moving between a place in which the treatment section is protruded from the arm section and a predetermined place in the arm section where a whole length of the treatment section is housed inside the arm section when the procedure instrument is inserted into the operation stick, wherein
    the operation stick further comprises:
    a falloff-preventive section for preventing the operation part of the procedure instrument from falling off the operation stick, the falloff-preventive section is arranged at a proximal end side of the operation stick and is configured to lock and stop movement of the operation part of the procedure instrument within the operation stick when the treatment section is disposed at the predetermined place in the arm section,
    the first bending part of the arm section is bent by tilting the operation stick in at least one of vertical and horizontal directions,
    wherein the falloff-preventive section comprises a piston enclosed within the operation stick.

2. The medical apparatus according to claim 1, wherein the falloff-preventive section is provided in a vicinity of a base end side of the operation stick relative to a regulation section configured to regulate movement of the bending operating part.

3. The medical apparatus according to claim 1, wherein the second channel formed by a plurality of pipes is capable of extending and contracting in the operation stick, and a base end of the second channel has a shape capable of making contact with a part of the procedure instrument, and the second channel is contracted by moving the procedure instrument inserted in the second channel toward a tip of the operation stick.

4. The medical apparatus according to claim 1, wherein when the procedure instrument is inserted in the second channel, a regulation section configured to regulate movement of the bending operating part is moved by the procedure instrument, and regulation to the bending operating part is released to enable operation of the first bending part.

5. The medical apparatus according to claim 1, wherein the bending operating part is a slider capable of sliding and attached to a main body of the operation stick.

6. The medical apparatus according to claim 1, wherein the bending operating part is a lever attached to a main body of the operation stick.

7. The medical apparatus according to claim 1, wherein the falloff-preventive section is formed to be capable of engaging with an engagement section provided on an outer periphery of the procedure instrument.

8. The medical apparatus according to claim 1, further comprising an observation section, attached to the sheath for observing an observation object.

9. The medical apparatus according to claim 1, wherein the arm section has a second bending part capable of a bending operation, the second bending part being disposed at further toward a proximal side of the arm section than the first bending part.

10. A medical apparatus comprising:
    a flexible sheath;
    a procedure instrument having a treatment section provided at a distal end of the procedure instrument;
    an arm section having a first bending part capable of a bending operation and a first channel capable of inserting the treatment section therethrough and capable of protruding therefrom, the arm section being disposed to protrude from a tip of the sheath;
    an operation stick having a bending operating part connected to the arm section by an operation-transmission member; and
    a channel unit inserted into the operation stick detachably and having a second channel connected to the first channel and inserting the procedure instrument therethrough; and
    an operation part provided in a proximal end side of the procedure instrument for operating the treatment section; wherein
    the procedure instrument is configured to be capable of moving between a place in which the treatment section is protruded from the arm section and a predetermined place in the arm section where a whole length of the treatment section is housed inside the arm section when the procedure instrument is inserted into the operation stick, wherein
    the channel unit further comprises:
    a falloff-preventive section for preventing the operation part of the procedure instrument from falling off the channel unit, the falloff-preventive section is arranged at a proximal end side of the channel unit and is configured to lock and stop movement of the operation part of the procedure instrument within the channel unit to when the treatment section is disposed at the predetermined place in the arm section,
    the first bending part of the arm section is bent by tilting the operation stick in at least one of vertical and horizontal directions,
    wherein the falloff-preventive section comprises a piston enclosed within the operation stick.

11. The medical apparatus according to claim 10, wherein the falloff-preventive section is provided in a vicinity of a base end side of the channel unit relative to a regulation section configured to regulate movement of the bending operating part.

12. The medical apparatus according to claim 10, wherein the second channel formed by a plurality of pipes is capable of extending and contracting in the channel unit, and a base end of the second channel has a shape capable of making contact with a part of the procedure instrument, and the second channel is contracted by moving the procedure instrument inserted in the second channel toward a tip of the channel unit.

13. The medical apparatus according to claim 10, wherein when the procedure instrument is inserted in the second channel, a regulation section configured to regulate movement of the bending operating part is moved by the procedure instrument, and regulation to the bending operating part is released to enable operation of the first bending part.

14. The medical apparatus according to claim 10, wherein the bending operating part is a slider capable of sliding and attached to a main body of the operation stick.

15. The medical apparatus according to claim 10, wherein the bending operating part is a lever attached to a main body of the operation stick.

16. The medical apparatus according to claim 10, wherein the falloff-preventive section is formed to be capable of engaging with an engagement section provided on an outer periphery of the procedure instrument.

17. The medical apparatus according to claim 10, further comprising an observation section, attached to the sheath for observing an observation object.

18. The medical apparatus according to claim 10, wherein the arm section has a second bending part capable of a bending operation, the second bending part being disposed at further toward a proximal side of the arm section than the first bending part.

* * * * *